United States Patent
Jesme et al.

(10) Patent No.: US 10,509,002 B2
(45) Date of Patent: Dec. 17, 2019

(54) WIRELESS SENSING DEVICES AND METHOD FOR DETECTING HYDRATION

(71) Applicant: 3M INNOVATIVE PROPERTIES COMPANY, St. Paul, MN (US)

(72) Inventors: Ronald D. Jesme, Plymouth, MN (US); Andrew P. Bonifas, Alberta (CA); Nicholas T. Gabriel, Woodbury, MN (US); Anthony J. Nowicki, Woodbury, MN (US)

(73) Assignee: 3M INNOVATIVE PROPERTIES COMPANY, St. Paul, MN (US)

( * ) Notice: Subject to any disclaimer, the term of this patent is extended or adjusted under 35 U.S.C. 154(b) by 148 days.

(21) Appl. No.: 15/521,757

(22) PCT Filed: Nov. 2, 2015

(86) PCT No.: PCT/US2015/058594
§ 371 (c)(1),
(2) Date: Apr. 25, 2017

(87) PCT Pub. No.: WO2016/073344
PCT Pub. Date: May 12, 2016

(65) Prior Publication Data
US 2017/0234818 A1    Aug. 17, 2017

Related U.S. Application Data

(60) Provisional application No. 62/077,009, filed on Nov. 7, 2014.

(51) Int. Cl.
*G01N 25/00*    (2006.01)
*G01K 1/00*    (2006.01)
(Continued)

(52) U.S. Cl.
CPC ............ *G01N 25/56* (2013.01); *A61B 5/0008* (2013.01); *A61B 5/443* (2013.01); *G01F 23/22* (2013.01);
(Continued)

(58) Field of Classification Search
USPC .................................. 374/45, 141, 102, 163
See application file for complete search history.

(56) References Cited

U.S. PATENT DOCUMENTS 5,050,604 A    9/1991    Reshef et al.
5,073,781 A    12/1991   Stickelbrocks
(Continued)

FOREIGN PATENT DOCUMENTS

CN    102721709 A    10/2012
DE    10258670       6/2004
(Continued)

OTHER PUBLICATIONS

Arnaud, "A micro thermal diffusion sensor for non-invasive skin characterization", Sensors and Actuators A, Elsevier Sequoias.A., Lausanne, CH, vol. 41, No. 1-3, Apr. 1, 1994 (Apr. 1, 1994), pp. 240-243.
(Continued)

*Primary Examiner* — Mirellys Jagan
(74) *Attorney, Agent, or Firm* — X. Christina Huang

(57) ABSTRACT

At least some aspects of the present disclosure feature an RF hydration sensor in an assembly, comprises a substrate; an antenna disposed on the substrate; an RF circuit electrically coupled to the antenna; a thermal source electrically coupled to the RF circuit for changing a thermal condition of a target area; and a sensing element thermally coupled to the thermal source for sensing a temperature of the thermal source. The
(Continued)

RF hydration sensor wirelessly receives a power from a remote transceiver and provides at least part of the power to the thermal source.

11 Claims, 21 Drawing Sheets

(51) Int. Cl.
    *G01K 7/00*     (2006.01)
    *G01N 25/56*     (2006.01)
    *A61B 5/00*     (2006.01)
    *G01N 27/18*     (2006.01)
    *H02J 50/20*     (2016.01)
    *G01F 23/22*     (2006.01)

(52) U.S. Cl.
    CPC .............. *G01N 27/18* (2013.01); *H02J 50/20* (2016.02); *A61B 2560/0214* (2013.01)

(56) References Cited

U.S. PATENT DOCUMENTS

| | | | |
|---|---|---|---|
| 6,087,930 | A | 7/2000 | Kulka et al. |
| 6,437,692 | B1 | 8/2002 | Petite et al. |
| 7,148,803 | B2 | 12/2006 | Bandy et al. |
| 7,256,695 | B2 | 8/2007 | Hamel et al. |
| 7,402,135 | B2 | 7/2008 | Leveque et al. |
| 7,463,142 | B2 | 12/2008 | Lindsay |
| 7,969,307 | B2 | 6/2011 | Petters |
| 8,307,708 | B2 | 11/2012 | Lin |
| 8,406,865 | B2 | 3/2013 | McKenna |
| 2001/0044588 | A1* | 11/2001 | Mault ................. A61B 5/0002 600/549 |
| 2003/0210146 | A1 | 11/2003 | Tseng |
| 2004/0035465 | A1* | 2/2004 | Cazden ................. E04H 4/12 137/392 |
| 2004/0059212 | A1* | 3/2004 | Abreu ................. A61B 5/01 600/373 |
| 2004/0113790 | A1 | 6/2004 | Hamel et al. |
| 2006/0253011 | A1 | 11/2006 | Edmonson et al. |
| 2007/0209434 | A1* | 9/2007 | Peters ................. G01F 23/2962 73/290 V |
| 2008/0202220 | A1 | 8/2008 | Schmidt |
| 2009/0091501 | A1 | 4/2009 | Mizoroki et al. |
| 2010/0090656 | A1 | 4/2010 | Shearer et al. |
| 2011/0106485 | A1 | 5/2011 | Popov et al. |
| 2011/0213559 | A1 | 9/2011 | Pollack et al. |
| 2011/0217205 | A1 | 9/2011 | Peeters |
| 2012/0106589 | A1 | 5/2012 | Ozawa |
| 2013/0106396 | A1 | 5/2013 | Forster |
| 2013/0256825 | A1 | 10/2013 | Humbert et al. |
| 2013/0341315 | A1 | 12/2013 | Blank et al. |
| 2014/0008355 | A1 | 1/2014 | Chaffey et al. |
| 2014/0209692 | A1 | 7/2014 | Ozaki |
| 2014/0217091 | A1 | 8/2014 | Ho et al. |
| 2015/0286913 | A1* | 10/2015 | Fastert ................. G06K 19/027 374/163 |
| 2017/0016984 | A1* | 1/2017 | Lin ................. G01S 13/584 |

FOREIGN PATENT DOCUMENTS

| | | |
|---|---|---|
| EP | 2618112 | 7/2013 |
| GB | 2308947 | 7/1997 |
| GB | 2701455 | 2/2014 |
| TW | 201315996 A | 4/2013 |
| WO | WO 2003-098175 | 1/2003 |
| WO | WO 2013-123130 | 8/2013 |
| WO | WO 2016-018585 | 2/2016 |
| WO | WO 2016-018777 | 2/2016 |
| WO | WO 2016-073327 | 5/2016 |
| WO | WO 2016-073344 | 5/2016 |
| WO | WO 2016-073408 | 5/2016 |
| WO | WO 2016-073413 | 5/2016 |

OTHER PUBLICATIONS

Axisa, "Flexible Technologies and Smart Clothing for Citizen Medicine, Home Healthcare, and Disease Prevention", IEEE Transactions on Information Technlogy in Biomedicine, vol. 9, No. 3, Sep. 2005, pp. 325-336.
Brisson, "A simple and disposable sweat collector", European Journal of Applied Physiology and Occupational Physiology, 1991, pp. 269-272.
Dittmar, Thirteen: Skin Thermal Conductivity a Reliable Index of Skin Blood Flow and Skin Hydration, Laboratory of Thermoregulation, U.A. 181 C.N.R.S., Lyon, France, Apr. 5, 1989, Clinical Dermatology, Cutaneous Investigation in Health and Disease, Noninvasive Methods and Instrumentation, pp. 323-358.
Gustafsson, Transient plane source techniques for thermal conductivity and thermal diffusivity measurements of solid materials, Rev. Sci.Instrum., vol. 62, pp. 797-804, Mar. 1991.
Havenith, "Male and female upper body sweat distribution during running measured with technical absorbents," Eur J. Appl Physiol, 2008, pp. 245-255.
Lin, "RFID-Based Thermal Convection Accelerometer", 2012 IEE Sensors (1-4577-1766-2, 978-1-4577-1766-6, 4 pages.
McColl, Monitoring moisture without disturbing the wound dressing, Wounds IK, 2009, vol. 5, No. 3, pp. 94-99.
Mehmet Safak: "Wireless Sensor and Communication Nodes with Energy Harvesting", Journal of Communication, Navigation, Sensing and Services (CONASENSE), vol. 1, No. 1, Jan. 1, 2014 (Jan. 1, 2014) , pp. 47-66.
Milos, Wireless subsurface microsensors for health monitoring of thermal protection systems on hypersonic vehicles, 2001, Proceedings of SPIE, v4335, pp. 74-82.
Patterson, "Variations in regional sweat composition in normal human males," Publication of the Physiological Society, 2000, pp. 869-876.
Rose, "System-level design of an RFID sweat electrolyte sensor patch", 2014 36th Annual International Conference of the IEEE Engineering in Medicine and Biology Society, IEEE, Aug. 26, 2014 (Aug. 26, 2014), pp. 4038-4041, XP032675498.
Tsai, "Investigation of Variability in Skin Tissue Intrinsic Thermal Conductivity Measurements", May 12, 1995, 77 pages.
Webb, "Ultrathin conformal devices for precise and continuous thermal characterization of human skin", Nature Materials, vol. 12, No. 10, Sep. 15, 2013 (Sep. 15, 2013), pp. 938-944.
International Search Report for PCT International Application No. PCT/US2015/058722, dated Feb. 16, 2016, 5 pgs.
International Search Report for PCT International Application No. PCT/US2015/058728, dated Feb. 18, 2016, 4 pgs.
International Search Report for PCT International Application No. PCT/US2015/058545, dated May 11, 2016, 7 pgs.
International Search Report for PCT International Application No. PCT/US2015/058594, dated Feb. 12, 2016, 5 pgs.

\* cited by examiner

WIRELESS SENSING DEVICES AND METHOD FOR DETECTING HYDRATION

CROSS REFERENCE TO RELATED APPLICATIONS

This application is a national stage filing under 35 U.S.C. 371 of PCT/US2015/058594, filed Nov. 2, 2015, which claims priority to Application No. 62/077009, filed Nov. 7, 2014, the disclosure of which is incorporated by reference in its/their entirety herein.

TECHNICAL FIELD

The present disclosure relates to wireless sensing devices and systems. At least part of the present disclosure relates to wireless sensing devices having excitation components. At least part of the present disclosure relates to wearable wireless sensors for measuring one or more thermal properties.

SUMMARY

In one embodiment, an RF hydration sensor in an assembly, comprises a substrate; an antenna disposed on the substrate; an RF circuit electrically coupled to the antenna, the RF circuit comprising a processor; a thermal source electrically coupled to the RF circuit for changing a thermal condition of a target area; and a sensing element thermally coupled to the thermal source for sensing a temperature of the thermal source, such that when the thermal source is thermally coupled to the target area, the RF hydration sensor wirelessly receives a first power having a first form from a transceiver, the RF circuit transforms the first power to a second power having a second form different from the first form and delivers the second power to the thermal source, the sensing element senses a time variation of the thermal source temperature, and the processor determines a hydration indicator indicating hydration level based on the sensed time variation of the thermal source temperature.

In one embodiment, an RF sensor for measuring a liquid level, comprises a substrate; an antenna disposed on the substrate; an RF circuit electrically coupled to the antenna, the RF circuit comprising a processor; an absorption element comprising an absorption material, a thermal source electrically coupled to the RF circuit and thermally coupled to the absorption element; and a sensing element thermally coupled to the thermal source for sensing a temperature of the thermal source, such that after the absorption element is used to absorb liquid, the RF sensor wirelessly receives a first power having a first form from a transceiver, the RF circuit transforms the first power to a second power having a second form different from the first form and delivers the second power to the thermal source, the sensing element senses a time variation of the thermal source temperature, and the processor determines an indicator indicating liquid level based on the sensed time variation of the thermal source temperature.

In one embodiment, a method of determining hydration level using one or more processors and a sensor having a thermal source disposed proximate to an object, comprises the step of: wirelessly activating the thermal source; generating a series of sensing signals by the sensor; determining, by the one or more processors, a thermal property of the object based on at least some of the series of sensing signals; and generating, by the one or more processors, a hydration indicator indicative of hydration level of the object based on the determined thermal property and a reference data.

In one embodiment, an RF hydration sensing system comprises an RF sensor tag, comprising a substrate; an antenna disposed on the substrate; an RF circuit electrically coupled to the antenna; a thermal source electrically coupled to the RF circuit for changing a thermal condition of a target area; and a sensing element thermally coupled to the thermal source for sensing a temperature of the thermal source, such that when the thermal source is thermally coupled to a target area, the RF sensor tag wirelessly receives a first power having a first form from a transceiver, the RF circuit transforms the first power to a second power having a second form and delivers the second power to the thermal source, the sensing element senses a time variation of the thermal source temperature, and the RF sensor tag wirelessly transmits the sensed time variation of the thermal source temperature; an RF reader configured to wirelessly transmit an interrogation power the RF sensor tag and receive the sensed time variation of the thermal source temperature; a processor electronically coupled to the RF reader and configured to determine a hydration indicator indicative of hydration level based on the sensed time variation of the thermal source temperature.

BRIEF DESCRIPTION OF DRAWINGS

The accompanying drawings are incorporated in and constitute a part of this specification and, together with the description, explain the advantages and principles of the invention. In the drawings.

Figure 1A:
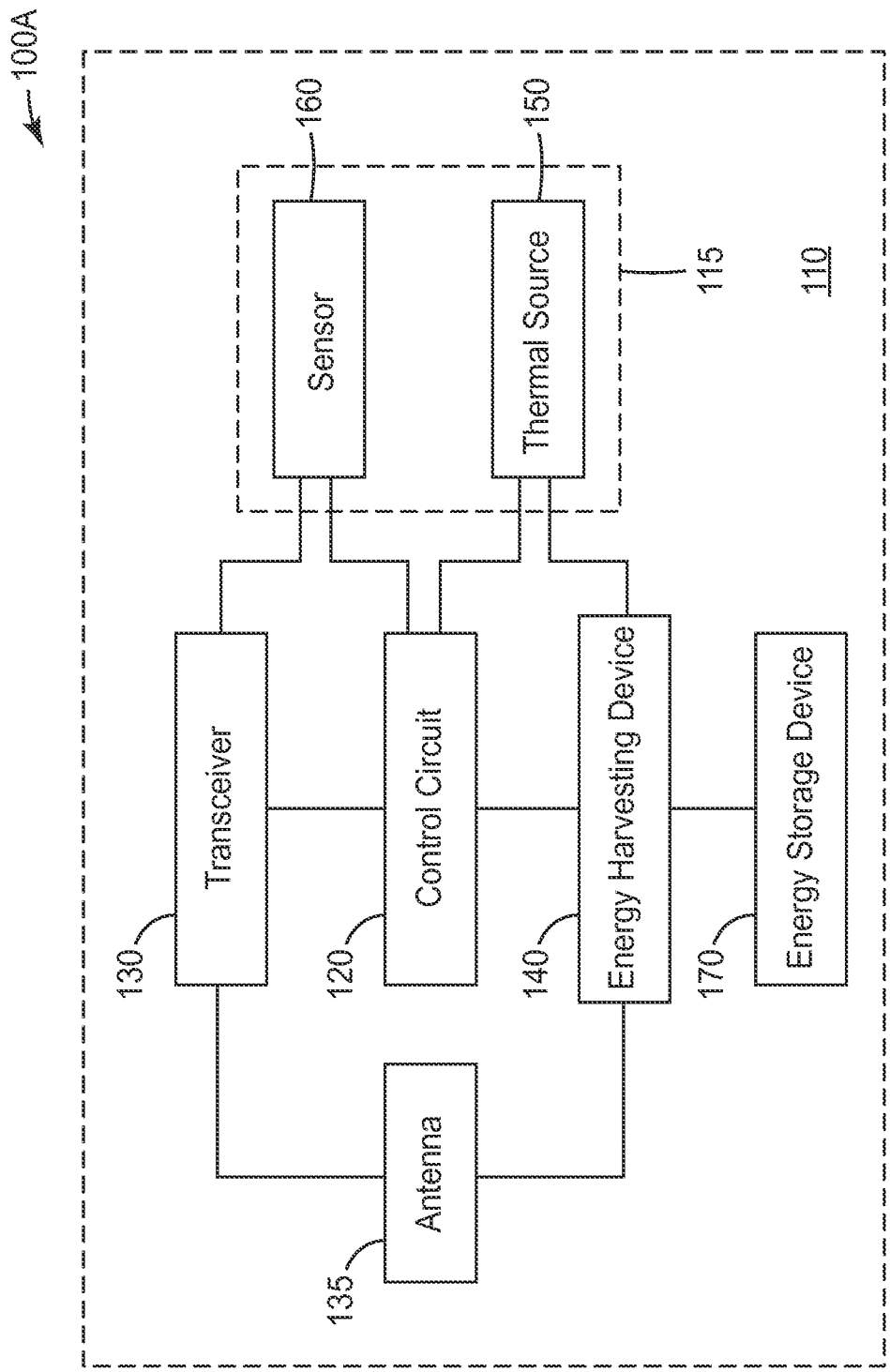
FIG. 1A illustrates a block diagram of one embodiment of a wireless sensing device.

In the drawings, like reference numerals indicate like elements. While the above-identified drawing, which may not be drawn to scale, sets forth various embodiments of the present disclosure, other embodiments are also contemplated, as noted in the Detailed Description. In all cases, this disclosure describes the presently disclosed disclosure by way of representation of exemplary embodiments and not by express limitations. It should be understood that numerous other modifications and embodiments can be devised by those skilled in the art, which fall within the scope and spirit of this disclosure.

DETAILED DESCRIPTION

Unless otherwise indicated, all numbers expressing feature sizes, amounts, and physical properties used in the specification and claims are to be understood as being modified in all instances by the term "about." Accordingly, unless indicated to the contrary, the numerical parameters set forth in the foregoing specification and attached claims are approximations that can vary depending upon the desired properties sought to be obtained by those skilled in the art utilizing the teachings disclosed herein. The use of numerical ranges by endpoints includes all numbers within that range (e.g. 1 to 5 includes 1, 1.5, 2, 2.75, 3, 3.80, 4, and 5) and any range within that range.

As used in this specification and the appended claims, the singular forms "a," "an," and "the" encompass embodiments having plural referents, unless the content clearly dictates otherwise. As used in this specification and the appended claims, the term "or" is generally employed in its sense including "and/or" unless the content clearly dictates otherwise.

Spatially related terms, including but not limited to, "lower," "upper," "beneath," "below," "above," and "on top," if used herein, are utilized for ease of description to describe spatial relationships of an element(s) to another. Such spatially related terms encompass different orientations of the device in use or operation in addition to the particular orientations depicted in the figures and described herein. For example, if an object depicted in the figures is turned over or flipped over, portions previously described as below or beneath other elements would then be above those other elements.

As used herein, when an element, component or layer for example is described as forming a "coincident interface" with, or being "on" "connected to," "coupled with" or "in contact with" another element, component or layer, it can be directly on, directly connected to, directly coupled with, in direct contact with, or intervening elements, components or layers may be on, connected, coupled or in contact with the particular element, component or layer, for example. When an element, component or layer for example is referred to as being "directly on," "directly connected to," "directly coupled with," or "directly in contact with" another element, there are no intervening elements, components or layers for example. As used herein, "electronically coupled" and "electrically coupled" are used interchangeably.

As used herein, layers, components, or elements may be described as being adjacent one another. Layers, components, or elements can be adjacent one another by being in direct contact, by being connected through one or more other components, or by being held next to one another or attached to one another. Layers, components, or elements that are in direct contact may be described as being immediately adjacent.

Some aspects of the present disclosure are directed to the development of sensors built upon radio frequency (RF) technology, which is an attractive approach based on the ability for wireless data and power transfer. As used herein, RF is used to refer to a broad class of wireless communication interface that can provide communications and power, including far field communication and near field communication (NFC), which may utilize a specific communication protocol. Sensors based on RF technology enable beneficial system attributes, such as wireless readout, passive (battery-free) sensor operation, unique sensor identification, compatibility with the human body, and onboard micro-processing capabilities. In addition, the growing prevalence of NFC enabled smart devices, such as smart phones, tablets, and smart watches, allows readout of RF based sensors without the need for a specialized reader. NFC includes but is not limited to the set of standard protocols defined by the NFC Forum industry association.

At least some aspects of the present disclosure feature wireless sensing devices for measuring thermal properties that can transmit sensor signals via a wireless interface. A wireless interface includes far field communications and NFC. In some embodiments, the wireless sensing device use NFC as communication interface. At least some aspects of the present disclosure feature wireless sensing devices having a thermal spreader, also referred to as thermal region or heat spreading layer, where the thermal spreader is formed by solid or liquid materials that have relatively high thermal conductivity in comparison to the thermal conductivity of gas, and a thermal source and a sensor disposed in the thermal spreader to allow measurement of one or more thermal properties. In some cases, the wireless sensing device includes an energy harvesting device to receive and convert power and supply power to at least some of the other components of the wireless sensing devices.

In some embodiments, a wireless sensing device has a single antenna with two or more sensors and excitation devices, where each sensor is coupled to an RF device having a unique identifier and each sensor is coupled to an excitation device. In such embodiments, the wireless sensing device can provide sensor signals from the spatially dispersed sensors to a computing device to determine physical properties based on spatial information and sensor signals.

In some embodiments, a wireless sensing device has thermally isolated regions, where each region includes a thermal sensor and optional thermal source, the measurement of the thermal sensors can be used to determine thermal properties of an object of interest. In one embodiment, the wireless sensing device has one thermal region A comprising materials with high thermal conductivity and a region B that is thermally isolated from the region A, where the region A is in thermal contact with an object of interest. In such embodiment, the thermal property of the object can be determined based on differential sensor signals from sensor A disposed proximate to region A and sensor B disposed proximate to region B.

At least some aspects of the present disclosure are directed to a wireless sensing system having an RF reader and a wireless sensing device of any configuration described herein. In some embodiments, the wireless sensing system includes multiple sensors that are spatially separated and receives sensing signals from these sensors. In some cases of such embodiments, the wireless sensing system can establish an array or a map of sensing signals and thereby evaluate physical properties of a material or object at various parts corresponding to sensor positions. In some other embodiments, the wireless sensing system receives sensing signals that are temporally separated, from a wireless sensing device to measure a physical property of an object. In some cases of such embodiments, the wireless sensing system can establish a profile of sensing signal changes over time and thereby determine physical property of the object based on the profile. For example, the wireless sensing system can establish a temperature-time profile with one or more thermal sensors and determine water content within the material or object and further evaluate a hydration or moisture level of the material or object.

Thermal properties of a material or an object include, for example, thermal conductivity, thermal conductance, specific heat capacity, heat capacity, thermal diffusivity, or the like. Thermal conductivity is intrinsic temperature difference in response to an applied heat flux through a material, with typical units of power per length-temperature, such as watts per meter-Kelvin. Thermal conductance takes into account cross-sectional area of heat flux and material thickness, with typical units of power per temperature, such as watts per Kelvin. Specific heat capacity is intrinsic temperature rise in response to heat energy, with typical units of energy per mass-temperature, such as joules per kilogram-Kelvin. Heat capacity takes into account mass of material, with typical units of energy per temperature, such as joules per Kelvin. Thermal diffusivity is the ratio of thermal conductivity to the product of mass density and specific heat capacity and indicates how quickly a material would reach a temperature similar to its surrounding environment, with typical units of area per time, such as square meters per second.

A material or an object can be a composite, where thermal properties of a composite refer to effective or average thermal properties for the composite. Some composites have a dispersed phase in a dispersion medium, which are generally known as solutions, as colloids, or as suspensions depending on the length scale involved. The composite can be one-phase or mixed-phase, containing one or more of solids, liquids, or gases.

In some embodiments, thermal properties of composites whose dispersion medium is not a gas (i.e., non-aerosol composites) are measured and/or calculated. The non-aerosol composites include, for example, foams (i.e., gas dispersed in solid or liquid), emulsions (i.e., liquid dispersed in liquid or in solid), or sols (i.e., solid dispersed in liquid or in solid). The non-aerosol composites may also include, for example, a heterogeneous mixture of solids, liquids, or gases that are dispersed in a solid or liquid matrix. For example, the effective thermal conductivity of an acrylate adhesive having dispersed particles of aluminum oxide is based on the thermal conductivity of each material, the mixing fraction, and other properties such as particle shape.

FIG. 1A illustrates a block diagram of one embodiment of a wireless sensing device 100A, which can be used to measure a thermal property of an object. As described herein, a wireless sensing device is typically in an assembly. In the embodiment illustrated, the wireless sensing device 100A includes a substrate 110, a control circuit 120 disposed on the substrate 110, a transceiver 130 electronically coupled to the control circuit, an antenna 135 electronically coupled to the transceiver and disposed on the substrate 110, an optional energy harvesting device 140 disposed on the substrate, an optional thermal source 150 and a sensor 160. In some cases, the energy harvesting device 140 is electronically coupled to the antenna 135. The antenna 135 is configured to transmit signals when an RF reader interrogates the wireless sensing device 100A, for example.

In some configurations, the wireless sensing device 100A has an optional thermal spreader 115, which includes solid, liquid, or composite material and has a desired or known thermal property. In some cases, the thermal conductivity of the thermal spreader 115 is higher than the thermal conductivity of the substrate 110. In some other cases, the substrate is the thermal spreader that is configured to be in thermal contact with the object when the wireless sensing device is in use for measuring the thermal property of the object. For example, the thermal spreader 115 includes a polymer film or an adhesive layer. In some implementations, the thermal spreader 115 has a thermal conductivity greater than or equal to 0.1 watts per meter-Kelvin. The thermal spreader 115 may include metallic fillers, such as aluminum, or ceramic fillers, such as boron nitride. In some cases, fillers used in the thermal spreader are to obtain a desired thermal conductivity. In some embodiments, the wireless sensing device 100A may improve accuracy of measurement results by providing generally uniform thermal flux through the thermal spreader 115. In some cases, the wireless sensing device 100A may use the thermal property of the thermal spreader 115 in determining the thermal property of the object.

Thermal flux or heat flux is the transfer of thermal energy through a medium by conduction (phonons), convection (fluid flow), or radiation (photons). The thermal flux of primary interest is that the thermal flux moves to and from a thermal source by conduction, and where the thermal flux is spread to or from a surface of a region or substrate.

The substrate 110 can be flexible or rigid. In some embodiments, the substrate 110 is stretchable. In some embodiments, the substrate 110 includes polyurethane. In some embodiments, the substrate 110 is a polymeric film. Suitable polymer films include elastomeric polyurethane, co-polyester, or polyether block amide films.

The control circuit 120 can include one or more electronic components that are electronically connected. The control circuit 120 can include passive electronic components, for example, such as resistors, capacitors, inductors, transformers, diodes, and the like. The control circuit 120 can include active electronic components such as transistors, voltage or current sources, amplifiers, microprocessors, oscillators, analog-to-digital converters, digital-to-analog converters, phase-locked loops, and the like. In some cases, the control circuit 120 may be formed into an integrated circuit or include an integrated circuit. A microprocessor may be a state machine with relatively simple digital logic to move among two or more states in a pre-defined manner, or a microcontroller comprised of an instruction set, digital processing blocks, memory, firmware, and peripherals such as clocks, memory controllers, and data converters. In some cases, the control circuit 120 comprises a microprocessor and a memory storing a unique identifier. In some embodiments, the control circuit 120, the transceiver 130, and the antenna 135 are components of a radio frequency identification (RFID) tag.

RFID tags on flexible and/or stretchable substrates are described in more details in U.S. Patent Application No. 62/031,581, entitled "RFID Tag on Stretchable Substrate" and filed on Jul. 31, 2014, and U.S. Patent Application No. 62/031,603, entitled "RFID Tag on Flexible Substrate" and filed on Jul. 31, 2014, the entirety of which are incorporated herein by reference.

In some cases, the thermal source 150 is disposed proximate the thermal spreader 115 to generate thermal flux in the thermal spreader 115. The thermal source 150 is electronically coupled to the energy harvesting device 140 and generates thermal flux in the thermal spreader 115. In some embodiments, the sensor 160 is disposed in the thermal spreader 115 and electronically coupled to the control circuit 120. The sensor 160 is configured to generate a sensor signal indicating a temperature and provide the sensor signal to the control circuit 120. In some cases, the thermal source 150 and the sensor 160 are components of an integrated circuit. In some implementations, the thermal source 150 and the sensor 160 are a same resistive element.

The thermal source 150, also referred to as heating element, may generate heat by Joule heating, for example, by passing current through any electrical component that has a non-zero electrical resistance. For example, the thermal source 150 can be a resistor electronically connected to a source of current, or indirectly such as a metallic or magnetic material coupled to a changing magnetic field to produce electrical current by magnetic induction.

In some cases, the thermal source 150 can be a thermoelectric device operating based on the Peltier effect, such as a thermoelectric heater or cooler containing one or more junctions of p-type and n-type thermoelectric materials, typically wired electronically in series. Depending on the polarity of the electrical current, one portion of the thermoelectric device will increase in temperature and another portion will decrease in temperature, so the thermoelectric device may be used for heating and/or cooling. Such thermoelectric thermal sources may also have thermal contributions from Joule heating due to the non-zero electrical resistance of the elements.

In some cases, the thermal source 150 can be based on optical absorption, from an intentional source or from an ambient source of optical energy. In some other cases, the thermal source can include a parasitic element or otherwise unintentional source of heating or cooling. In some cases, the thermal source 150 is a dedicated component in the wireless sensing device 100A. In some other cases, the thermal source 150 includes one or more electronic components that are in operation in the wireless sensing device. For example, the thermal source 150 may include a transceiver element that generates additional heating during operation. As another example, the thermal source 150 includes a microprocessor element that generates heat during operation.

In some embodiments, the thermal source 150 is disposed proximate to the thermal spreader 115. In some cases, the thermal spreader 115 has a known thermal property, which can be used to determine one or more thermal properties of the object. In some implementations, the thermal source includes a high conductivity component. In some embodiments, the thermal source 150 and/or thermal spreader 115 is in thermal contact with the object or material of interest. Thermal contact is defined at an interface of two materials, where non-infinite thermal contact conductance results in a temperature difference across the interface when heat flux moves across the interface. The interface generally consists of a mixed-phase region similar to some of the composite materials described. In some embodiments, the interface may comprise solid regions with some roughness or within the solid regions, where fluid regions within that roughness. Fluid regions can include liquid, gas, or a mixture. In some embodiments, the interface may have solid or liquid regions with gas regions in one or more voids or at a surface. Maintaining good thermal contact or thermal coupling typically involves limiting the fraction of fluid regions especially those containing gas. Thermal interface materials are typically used for this purpose, such as elastomeric pads, adhesive tapes, greases, or the like. Effective contact thermal conductance is the inverse of temperature difference across a contact interface area for a given heat flux, having typical units of watts per square meter per Kelvin. Effective contact thermal conductance may be additionally scaled by an effective thickness of the contact region to obtain an effective contact thermal conductivity, having typical units of watts per meter per Kelvin.

In some embodiments, the sensor 160, also referred to as sensing element, may be a thermal sensor that has measurable changes in electrical property, optical property, acoustic property, or the like, in response to temperature changes. In some cases, electrical thermal sensors can have a response to temperature changes in electrical voltage, current, or resistance. A resistive thermal sensor has its electrical resistance dependent on temperature; typical metals are resistive thermal devices where resistance increases with temperature in a relatively linear relationship. A thermistor typically has a resistance that depends on electrical current and non-linear resistance changes in response to temperature changes. In some implementations, electrical thermal sensors may operate based on the Seebeck effect to convert a temperature difference into an electrical voltage, such as a thermocouple or thermopile.

An optical temperature sensor includes an optical transducer that receives electromagnetic radiation from objects out of thermal equilibrium with their environment, where the transducer temperature changes as it absorbs and emits radiation, for example, bolometers, microbolometers, pyroelectric detectors, or the like. These sensors combine optical and electrical aspects, where incident and reflected radiation is measured and converted to an electrical response when the transducer is heated or cooled by the radiation.

An acoustic temperature sensor relies on the temperature-induced change in propagation of mechanical waves through a bulk material or along the surface of a material. A sensor to measure temperature can comprise multilayer structures that deform in response to temperature based on differing thermal expansion properties of the layers. The deformation can be transduced electronically, such as a deformed beam that completes an electromechanical switch, or transduced as a visible indicator by means of a dial or other element.

In some cases, the energy harvesting device 140 comprises a bridge rectifier, a rectifier, a diode or transistor rectifier, and may include a voltage or current regulator. In some implementations, non-rectified electrical power may be provided to the thermal source (e.g., resistor), while the remainder of the electronic circuitry typically operates on rectified power. An energy harvesting device can receive power from an intentional radiation source or from an unintentional or ambient source. Intentional radiation sources may include, for example, an RF reader. For example, depending on the configuration of its electronics, antennas, and frequency ranges of operation, an RF reader can produce a near-field electrical or magnetic field that stores energy for coupling into one or more target devices, or it can produce a far-field radiation pattern of traveling electromagnetic waves, or a combination thereof. In some cases, the magnetic field may couple to the antenna 135 and the energy harvesting device 140 to induce an electrical current in the wireless sensing device from the magnetic field.

The energy harvesting device 140 may also be coupled to an unintentional or ambient source, for example, such as an optical source, inertial vibration source, or temperature gradient source, or the like. An optical source can be, for example sunlight, artificial lighting, or the like. In such examples, the energy harvesting device 140 can include photovoltaic cells to convert optical energy to electrical energy. An inertial or vibration source of energy can be, for example, a motor, a moving transportation vehicle (e.g., automobile, train, airplane, etc.), wind, or the like. It can also be a biological source such as a human in motion. In such examples, the energy harvesting device can include a piezoelectric device that converts mechanical energy to electrical energy. The energy harvesting device 140 can obtain electrical energy from a temperature gradient. For example, the energy harvesting device can include a thermoelectric device operating based on Seebeck effect that converts the temperature gradient and heat flow resulting from the skin of a mammal or from the outside of a pipe containing a process fluid into electrical energy.

In some embodiments, the thermal source 150 is regulated. The thermal source 150 can be regulated by the processing components of the control circuit 120, by interaction with an external device through the transceiver 130, the energy harvesting device 140, or by a combination thereof. In some cases, the control circuit 120 regulates the thermal source 150. In some cases, the control circuit 120 regulates the thermal source 150 based on sensor signals.

In some embodiments, the power delivered to the thermal source 150 can be modulated by a controller within the control circuit 120, for example, by changing the amount of electrical power delivered to the thermal source 150. In some embodiments, the control circuit 120 regulates the electrical power in order to maintain constant temperature or maintain a desired rate of change in temperature in response to the sensing signal indicative of temperature provided by the sensor 160, which is a closed-loop control based on temperature. In some embodiments, the control circuit 120 regulates the electrical power into the thermal source in order to maintain constant power or a desired rate of change in power supplied to the thermal source 150, which is a closed-loop control based on power. In some other embodiments, the thermal source 150 receives a known but uncontrolled current, voltage, or power, and the known value is used in later computation step(s) to account for variation in power which is an open-loop control. In yet some other embodiments, an open-loop type of control may be implemented with contingent constraints, such as a maximum or minimum value of a sensing signal obtained from sensor 160 and used by the control circuit 120 to adjust the thermal source 150 if the sensing signal is outside the maximum or minimum value.

In some embodiments, the thermal source 150 can be regulated by performing the measurement during a time period when a dominant parasitic/unintended heating element is operating. Such regulation can be done directly through an intentional increase in the operating load of the parasitic/unintended heating element. For example, the controller can instruct a transceiver to turn on and process otherwise nonsensical data in order to generate additional heat. In such example, the power supplied to the transceiver can be monitored by the controller, with the processing load adjusted to maintain a constant power or desired rate of change in power.

In some embodiments, the wireless sensing device 100A may include an optional energy storage device 170 that is disposed on the substrate and electronically coupled to the energy harvesting device 140. Energy storage devices 170 may include capacitors or supercapacitors. The energy storage device 170 may store energy harvested from the energy harvesting device 140 for a short or long term period of time. Energy stored in the energy storage device 170 may be used to provide power to designated components of the wireless sensing device 100A including, but not limited to, the control circuit 120, thermal source 150, and sensor 160. When external energy is not available to the energy harvesting device 140, the wireless sensing device 100A can continue to operate on power stored in the energy storage device 170. Also, energy stored in the energy storage device 170 can be used to augment the power available from the energy harvesting device 140, enabling higher power availability than the power available from the energy storage device 170 or the energy harvesting device 140 alone.

In some embodiments, the energy harvesting device 140 provides power to the thermal source 150, and possibly other components of the wireless sensing device 100A, such as the sensor 160, the control circuit 120, and the transceiver 130. In some cases, the sensor 160 is configured to generate a first sensor signal before the thermal source 150 is activated by the energy harvesting device 140 and a second sensor signal after the thermal source 150 is activated by the energy harvesting device 140. In such cases, the control circuit can determine a thermal property of the object based on the first and second sensor signals. In some cases, the sensor 160 is configured to generate a first sensor signal approximately concurrent with the activation of the thermal source 150 by the energy harvesting device 140, and a second sensor signal after the thermal source 150 is activated by the energy harvesting device 140.

The transceiver 130 can include a transmitter element and/or a receiver element. A transmitter element includes one or more electromagnetic or electroacoustic transducers, and electronic components to filter, amplify, and modulate one or more signals. A receiver element comprises one or more electromagnetic or electroacoustic transducers that can be shared with those of the transmitter element via a switching means or can be separate from those of the transmitter element, and electronics to filter, amplify and demodulate one or more signals from the received energy. An electromagnetic transducer can be an antenna, which can be designed to radiate electromagnetic fields from input electrical signals and absorb electromagnetic fields into electrical signals, or can be designed to couple with stored energy in electromagnetic near fields, or a combination of both radiation and near-field coupling. An electromagnetic transducer can also be a light-emitting diode or other optical source, or a photodiode or other optical detector. An electroacoustic transducer can be a loudspeaker or other acoustic source, or a microphone or other acoustic detector. Electromagnetic and/or electroacoustic transducers can be combined into a single element that is capable of bidirectional transduction from electrical signals to electromagnetic or acoustic energy, and from electromagnetic or acoustic energy to electrical signals.

As an example, the transceiver 130 can be included in an integrated circuit device, for example, NTAG213 from NXP Semiconductors (Eindhoven, the Netherlands). As another example, the transceiver 130 can be an infrared transceiver element with a light-emitting diode, a photo diode, and accompanying electronics to implement optical communications via an infrared protocol, for example, RPM841-H16 IrDA Infrared Communication Module from Rohm Semiconductor (Kyoto, Japan).

The antenna 135 can be a coil antenna designed for near-field coupling with an RF reader. In some cases, the antenna 135 has a spiral form. In some implementations, the antenna 135 comprises a plurality of substantially concentric electrically conductive loops. In some configurations, the antenna has a length between first and second ends, the length being less than about 2 meters. In some cases, the antenna 135 performs modulation and demodulation according to the standards, ISO 14443A, ISO 15693, or other standard or proprietary communication protocols. The coil antenna can have an inductance based on its geometry that produces a resonance with the capacitance of the electronically connected components, generally referred to as RF components, for enhanced induced voltage for a given magnetic field strength near the frequency of the RF reader. In some embodiments, the coil antenna may have an inductance based on its geometry that produces a first resonance with a first capacitance of the RF components and a second resonance with a second capacitance of the RF components, wherein the second resonance is more closely matched with the frequency of the RF reader, coupling more energy into the wireless sensing device 100A due to the increased induced voltage for a given reader magnetic field strength when resonance frequency more closely matched with the RF reader frequency. In some implementations, the RF components, which include components of the transceiver 130 and/or control circuit 120, may be configured to contain a tunable or switchable capacitance to produce the at least two values of capacitance (i.e., the first capacitance, the second capacitance), or may contain circuitry for controlling an external variable capacitance, or may contain circuitry to allow one or more external capacitance elements to be switched in or out of the circuit.

Figure 1B:
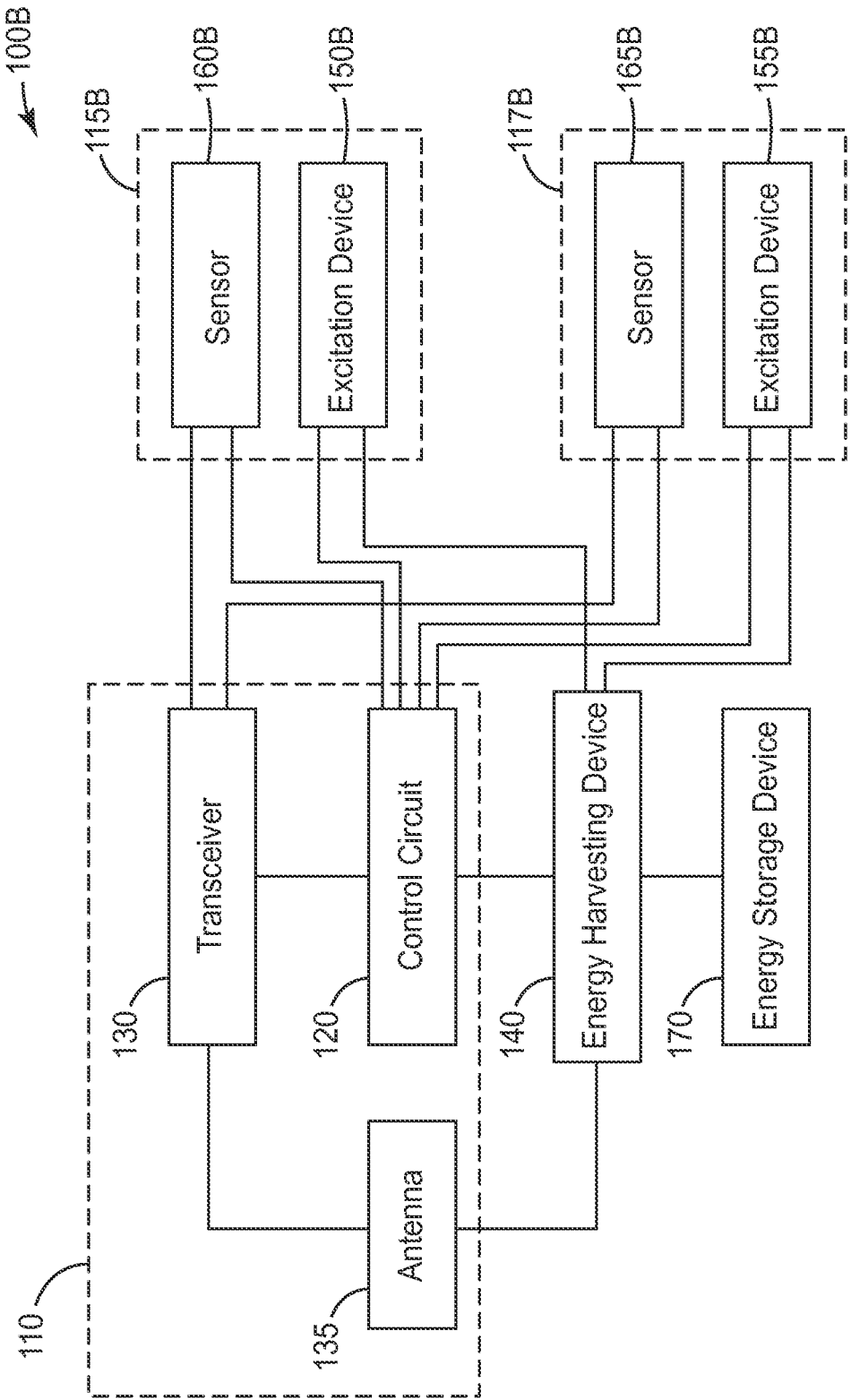
FIG. 1B illustrates a block diagram of another embodiment of a wireless sensing device.

FIG. 1B illustrates a block diagram of another embodiment of a wireless sensing device 100B, which can be used to measure physical property of an object. In the embodiment illustrated, the wireless sensing device 100B includes a substrate 110, a control circuit 120, a transceiver 130 electronically coupled to the control circuit, an antenna 135 electronically coupled to the transceiver and disposed on the substrate 110, an optional energy harvesting device 140 disposed on the substrate, a first excitation device 150B, a first sensor 160B, a second excitation device 155B, and a second sensor 165B. In some cases, the energy harvesting device 140 is electronically coupled to the antenna 135. In some embodiments, the wireless sensing device 100B includes an optional energy storage device 170. In some cases, the energy storage device 170 is electronically coupled to the energy harvesting device 140. In some embodiments, the wireless sensing device 100B includes a battery (not illustrated in FIG. 1B). Components with same labels can have same or similar configurations, compositions, functionality and/or relationships as the corresponding components in FIG. 1A.

The first excitation device 150B and the second excitation device 155B can include one or more of thermal excitation device, light excitation device, sound excitation device, vibrator, voltage source, current source, electromagnet, or the like. An excitation device can generate an excitation signal and/or excitation signals during a period of time. The excitation signal can include, for example, a light signal, a voltage signal, a vibration signal, a sound signal, heating or cooling signal, an electromagnetic signal, a current signal, or the like. The excitation devices (150B, 155B) can initiate an excitation signal to change a condition, and the sensor (160B, 165B) can sense the physical characteristics of the object that varies in response to the changed condition and then determine one or more physical characteristics of the object. As one example illustrated in FIG. 1A, the excitation device can be a thermal source in thermal contact with the object, and the sensor is selected to measure temperature changes of the object. As another example, the excitation device can be a vibration motor in contact with the object, and the sensor can be an accelerometer.

In some cases, the excitation device (150B and/or 155B) can generate optical energy, for example, such as light source, or the like; and the corresponding sensor can include optical sensor, for example, such as photodiode, photovoltaic sensor, or the like. In some cases, the excitation device can include a motion source, for example, such as vibration motor, piezoelectric actuator, or the like; and the corresponding sensor can include a motion sensor, for example, such as piezoelectric sensor, accelerometer, or the like. In some other cases, the excitation device can include an acoustic source, for example, such as microphone, piezoelectric transducer, or the like; and the corresponding sensor can include an acoustic sensor, such as microphone, accelerometer, or the like. In yet some other cases, the excitation device can include an electrical source, for example, such as voltage source, current source, or the like; the corresponding sensor can include an electrical sensor, for example, such as voltage sensor, current sensor, phase sensor, resistance sensor, or the like. In some implementations, the wireless sensing device can include more than one type of excitation devices, for example, both an optical source and a motion source, and/or more than one type of sensors, for example, both an optical sensor and a motion sensor.

In some embodiments, the wireless sensing device 100B can include two or more sensors spatially separated to measure physical properties at different parts of the object. The sensor data can be used to, for example, increase accuracy of measurement results, measure flow rate, detect anomalies in the object, or evaluate other properties of the object. In some cases, the excitation device 150B and/or 155B can be regulated by the control circuit 120. In some cases, the excitation device 150B and/or 155B can be regulated by the control circuit 120 based on sensor signal.

In some configurations, the wireless sensing device 100B has an optional sensing region 115B and/or sensing region 117B, which comprises materials suitable for a specific energy transfer. For example, the sensing region 115B and/or 117B includes a polymer film or an adhesive layer suitable for thermal energy transfer. As another example, the sensing region 115B and/or 117B includes a reflective film suitable for directing light to the object.

In one embodiment, the excitation device 150B and 155B are thermal sources. The sensing regions 115B and 117B are thermally isolated from each other. The first thermal source 150B is disposed in the first sensing region 115B and is electronically coupled to the energy harvesting device 140. The first sensor 160B is disposed in the first sensing region 115B and electronically coupled to the control circuit 120. The first sensor 160B is configured to generate a first sensor signal associated with temperature. The second thermal source 155B is disposed in the second sensing region and electronically coupled to the energy harvesting device 140. The second sensor 165B is disposed in the second sensing region 117B and electronically coupled to the control circuit 120. The second sensor 165B is configured to generate a second sensor signal associated with temperature. The control circuit 120 is configured to determine a thermal property of the object based on the first and second sensor signals. In some cases, the sensing region 117B is in thermal contact with the object and the sensor 160B in a thermal isolated region 115B can provide baseline information to improve the measurement accuracy of the wireless sensing device 100B.

In one embodiment, a thermal insulator is disposed between the sensing regions 115B and 117B. The thermal insulator can include, for example, foam, air gap, or the like. Foam may include, for example, any solid material having voids, such as a polymer material with open-cell or closed-cell voids, or a nonwoven polymer material. Thermal insulation is also provided by geometry, for example by the ratio of separation distance between regions to the cross-sectional area of the span between regions; a larger temperature difference is required to transfer a given amount of heat when that ratio is larger.

In some cases, the first sensing region 115B and/or the second sensing region 117B is on the substrate 110. In some other cases, the first sensing region 115B and/or the second sensing region 117B is not on the substrate 110. In one embodiment illustrated in FIG. 1B, the control circuit 120 receives sensing data from both sensors 160B and 165B. In some cases, the control circuit 120 includes a microprocessor to determine the physical property of the object based on the data collected by both sensors 160B and 165B. In some other cases, the control circuit 120 transmits the sensor data via the transceiver 130 for further processing.

Figure 1C:
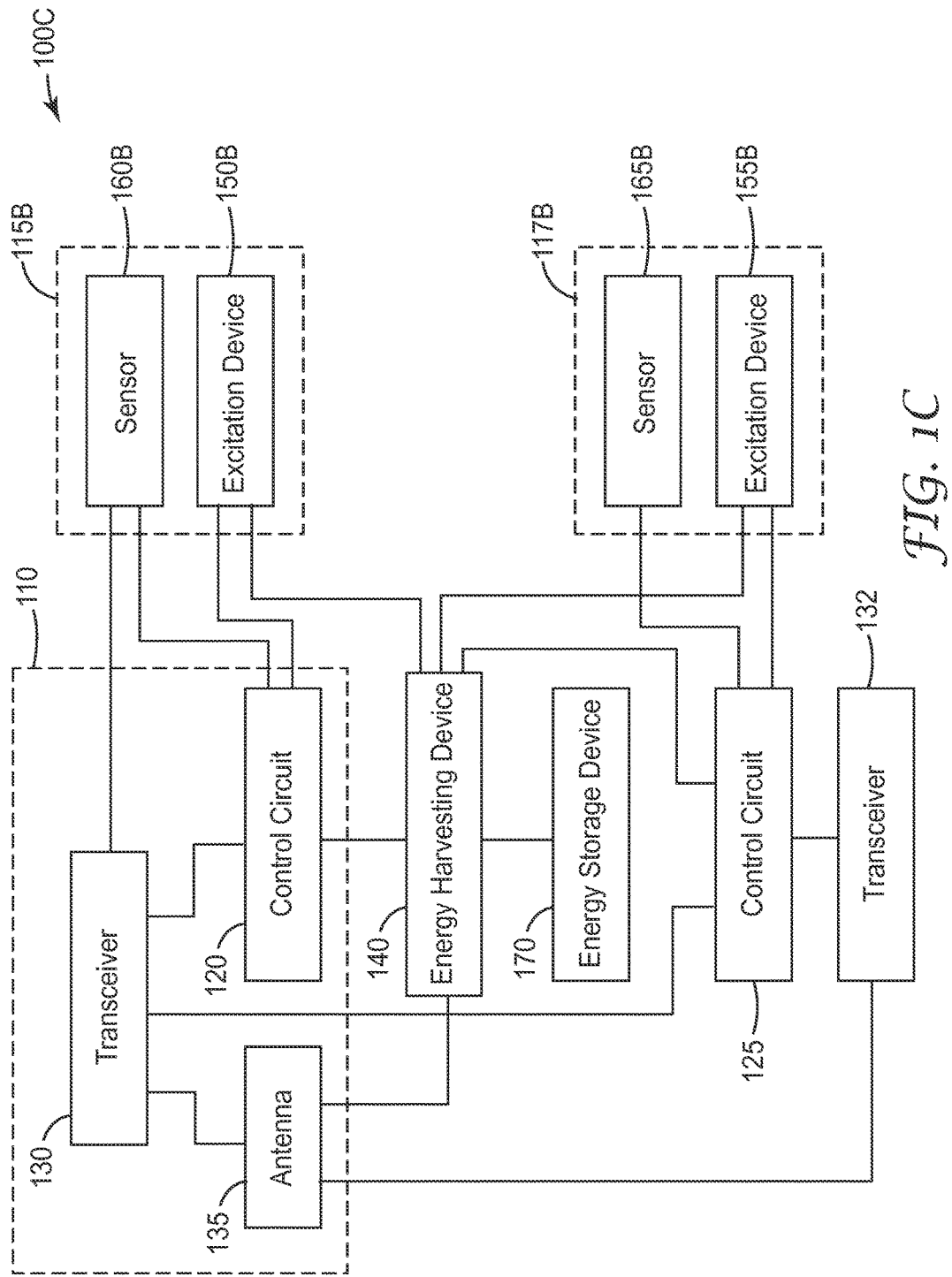
FIG. 1C illustrates a block diagram of yet another example of wireless sensing device.

FIG. 1C illustrates a block diagram of yet another example of wireless sensing device 100C, which can be used to measure one or more physical properties of an object. In the embodiment illustrated, the wireless sensing device 100C includes a substrate 110, a first control circuit 120, a first transceiver 130 electronically coupled to the first control circuit 120, a second control circuit 125, a second transceiver 132 electronically coupled to the second control circuit 125, an antenna 135 electronically coupled to the transceiver 130 and/or 135 and disposed on the substrate 110, an optional energy harvesting device 140 disposed on the substrate, a first excitation device 150B, a first sensor 160B, a second excitation device 155B, and a second sensor 165B. In some cases, the energy harvesting device 140 is electronically coupled to the antenna 135. In some cases, the wireless sensing device 100C includes a second antenna connected to the second transceiver 132 while the antenna 135 is connected to the first transceiver 130. Components with same labels can have same or similar configurations, compositions, functionality and/or relationships as the corresponding components in FIGS. 1A and 1B.

One or more components in any one of wireless sensing devices described herein, for example, control circuit, transceiver, thermal source, excitation device, sensor, energy harvesting device, and energy storage device can be made into an integrated circuit encapsulated within a electronic package. In some implementations, the wireless sensing devices described herein are passive sensing devices that do not include active power components (e.g., battery). In some other implementations, the wireless sensing devices described herein are active sensing devices that include active power components. In some cases, the embodiments of wireless sensing device described herein are built into a single electronic package. In some cases, these wireless sensing devices can be built into a NFC or RFID (radio frequency identification) tag as an addressable sensor.

The embodiments illustrated in FIGS. 1B and 1C having two or more sensors, may have a number of benefits, such as tag size reduction, simplification of manufacturing, multiple sensing circuits having access to the same power/magnetic field levels or a predefined ratio power/magnetic field levels, construction of one device having multiple sensors enabling differential sensing architecture and/or enabling spatial mapping/sensing. In the embodiment illustrated in FIG. 1C, the utilization of a single antenna 135 for multiple sensing circuits can eliminate magnetic coupling detuning of two closely spaced antenna elements. While FIGS. 1B and 1C illustrated two sensors and/or excitation devices in the wireless sensing device, a person skilled in the art should readily design a wireless sensing device having more than two sensors and/or excitation devices.

Figure 2A:
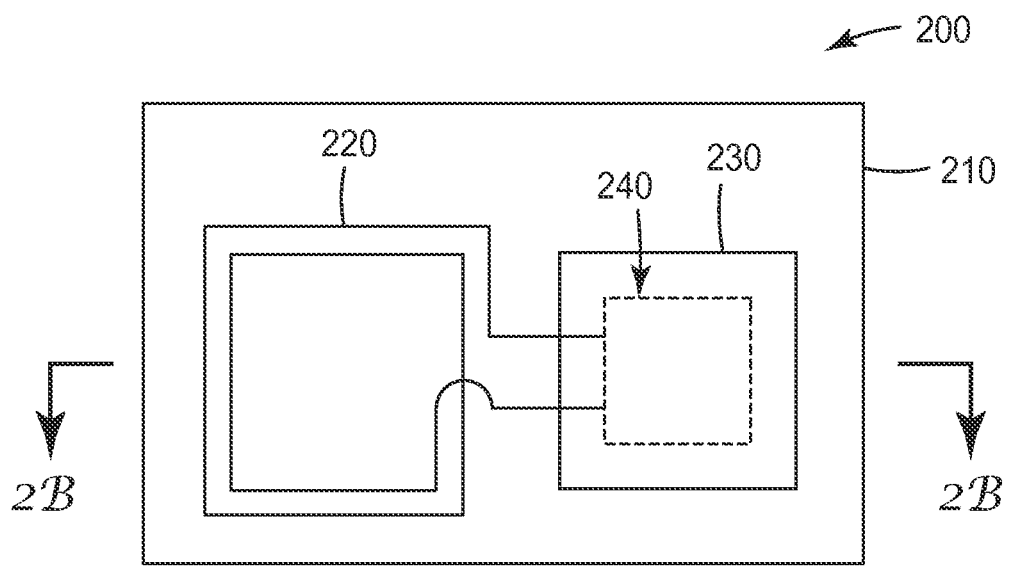
FIG. 2A is a simplified schematic of one embodiment of an RF sensor tag.
Figure 2B:
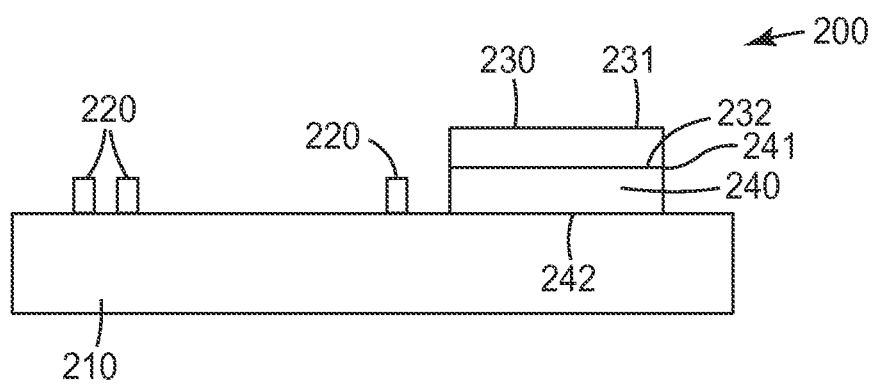
FIG. 2B is a cross sectional view of the wireless sensing device illustrated in FIG. 2A at arrow 2B.

FIG. 2A is a simplified schematic of one embodiment of an RF sensor tag 200; FIG. 2B is a cross sectional view of the wireless sensing device 200 at arrow 2B. The RF sensor tag 200 includes a substrate 210, an antenna 220 disposed on the substrate 210, an optional thermal spreader 230, and a sensing circuit 240 electronically coupled to the antenna 220. The sensing circuit 240 is disposed in the thermal spreader 230. In some embodiments, the sensing circuit 240 can include a transceiver, a memory storing a unique identifier, a sensing element, and a heating element for heating a target area. In some other embodiments, the sensing circuit 240 includes an energy harvesting device. In some cases, only part of the sensing circuit 240 is disposed in the thermal spreader 230. In some cases, the sensing element is thermally coupled to the heating element for sensing a temperature of the heating element, such that when the heating element is thermally coupled to a target area, the RF sensor tag 200 wirelessly receives a first power having a first form from a transceiver, the sensing circuit 240 transforms the first power to a second power having a second form different from the first form and delivers the second power to the heating element, the sensing element senses a time variation of the heating element temperature, and the RF sensor tag 200 wirelessly transmits to the transceiver a thermal characteristic of the target area based on the sensed time variation of the heating element temperature. In some cases, the first form could be a circulating alternating current and alternating voltage induced by an alternating magnetic field. In some cases, the second form could be a rectified version of the alternating voltage and current. In some embodiments, filtering of a rectified voltage and current by a capacitor or other means can produce approximately direct current and voltage as the second form. The second form can alternatively be an alternating current and voltage transformed by the sensing circuit to a different magnitude, frequency, and/or phase from the first form.

In some cases, the substrate 210 is flexible and/or stretchable. In some cases, the RF sensor tag 200 includes an integrated circuit (IC) comprising at least part of the sensing circuit 240. In such cases, the antenna has a length between first and second ends and the IC is electrically connected to the first and second ends of the antenna. In some cases, the IC includes the memory, the wireless transceiver and the heating element. In some other cases, the IC includes the memory, the wireless transceiver and the sensing element. In yet other cases, the IC includes the memory, the wireless transceiver, the heating element, and the sensing element.

In some embodiments, the thermal spreader 230 is disposed on a major surface of the IC and adapted to substantially uniformly distribute heat from the heating element across the target area, where the major surface of the IC is a major top surface 242 and a major bottom surface of the IC 241. In some cases, the thermal spreader has a top surface 232 in contact with the bottom surface of the IC and an opposing bottom surface 231 for thermally contacting the target area, the bottom surface 241 of the IC and the top surface 232 of the heat spreader 230 substantially overlapping one another. In some cases, an area of the bottom surface 231 of the thermal spreader 230 is greater than an area of the top surface 232 of the thermal spreader 230. In some other cases, an area of the bottom surface 231 of the thermal spreader 230 is smaller than an area of the top surface 232 of the thermal spreader 230.

In some cases, the heating element is also the temperature sensing element. In some implementations, the first form of power is an AC form and the second form is a DC form. In some cases, the second form comprises a rectified representation of the first form. In some cases, the sensing circuit 240 controls a magnitude of the second power.

In some embodiments, the RF sensor tag wirelessly receives an unknown first power having a first form from a wireless transceiver, and wherein the electronic circuit transforms the unknown first power to a known second power having a second form different from the first form. In some cases, the sensing element senses a time variation of the heating element temperature by generating a signal that has a known relationship to the heating element temperature. In some cases, the sensing element senses a time variation of the heating element temperature by generating a signal that is substantially proportional to the heating element temperature. In some implementations, when the sensing circuit transforms the first power to the second power, the sensing circuit is adapted to reduce a magnitude of the second power if the second power is greater than a maximum threshold value. In some cases, the sensing circuit is adapted to change the magnitude of the second power by changing a resonant frequency of the RF sensor tag. In some embodiments, the thermal characteristic of the target area wirelessly transmitted to the transceiver includes a thermal conductivity of the target area, a thermal diffusivity of the target area, and/or a heat capacity of the target area.

In some embodiments, the RF sensor tag 200 is adapted to wirelessly communicate with a remote transceiver emitting power at a first radio frequency, where the sensing circuit 240 is adapted to detune a resonant frequency of the RF sensor tag 200 away from the first radio frequency to control a magnitude of the first power received by the RF sensor tag from the remote transceiver. In some cases, the RF sensor tag 200 is adapted to wirelessly communicate with a remote transceiver emitting power at a first radio frequency, where the sensing circuit 240 is adapted to tune a resonant frequency of the RF sensor tag away from the first radio frequency and tune the detuned resonant frequency back to the first radio frequency. In some cases, the RF sensor tag 200 is adapted to wirelessly communicate with a remote transceiver emitting power at a first radio frequency, such that if a resonant frequency of the RF sensor tag 200 drifts away from the first radio frequency, the sensing circuit 240 is adapted to tune the drifted resonant frequency of the RF sensor tag 200 back to the first radio frequency.

Generally, maximum power transfer from the remote transceiver to the RFID tag occurs when the resonant frequency of the RFID tag is the same as the frequency at which power is emitted from the remote transceiver. In some cases, when the RFID tag is in close proximity to the remote transceiver, more power may be transferred to the RFID tag than is needed by the RFID tag. In this case, the RFID tag may sense the availability of excess power and react by detuning the RFID tag resonate frequency from the frequency at which power is emitted from the remote transceiver, thus reducing the power available to the RFID tag by reducing the efficiency by which power is transferred from the remote transceiver to the RFID tag. Detuning causes the resonate frequency of the RFID tag to be different than the frequency at which power is emitted from the remote transceiver, with the detuned resonate frequency of the tag being at a frequency that is greater or less than the frequency of the frequency at which power is emitted from the remote transceiver. In this example, the resonate frequency of the RFID tag is dependent on a tuning capacitance of the RFID tag that resonates with the inductance of a loop antenna of the RFID tag. As such, the resonate frequency of the RFID tag can be modified by modifying the value of this capacitance. This capacitance can be modified by electronically coupling additional capacitance in parallel with a base value of this capacitance, or electronically disconnecting parallel capacitance from this base value of capacitance. In an alternative configuration, this base value of capacitance could be modified by coupling a varactor diode in parallel with this base value of capacitance and modifying the capacitance of the varactor diode by modifying a DC bias present across the varactor diode.

Another means of detuning the RFID tag to reduce the efficiency by which power is transferred from the remote transceiver to the RFID tag is to reduce the Q factor of the RFID tag, for example by reducing the Q factor of the RFID tag antenna. The Q (or quality factor) of the RFID tag antenna is the ratio of energy stored in the antenna to the energy dissipated by antenna, where the energy can be stored as a magnetic field and dissipated as heat due to the electrical resistance of the antenna. While many parameters contribute to the efficiency of power transfer from a remote transceiver to a RFID tag, the Q factor of the RFID tag antenna can in some cases have a direct influence on the efficiency of power transfer. The Q factor of the RFID tag antenna can be reduced by coupling an additional electrical resistance in series with the RFID tag antenna or by coupling an electrical resistance in parallel with the RFID tag antenna. This resistance can be controlled by a controller circuit. In some cases, when the RFID tag is in close proximity to the remote transceiver, more power may be transferred to the RFID tag than is needed by the RFID tag. In this case, the RFID tag may sense the availability of excess power and react by reducing the efficiency of power transfer from the remote transceiver to the RFID tag by reducing the Q factor of the RFID tag by reducing the Q factor of the RFID tag antenna by modifying a resistance that is coupled to the RFID tag antenna. An electronically controlled resistance that is coupled to the RFID tag antenna could be implemented with a field effect transistor, varactor diode, transistor switch, or any analog or digital means of controlling a resistance.

Figure 2C:
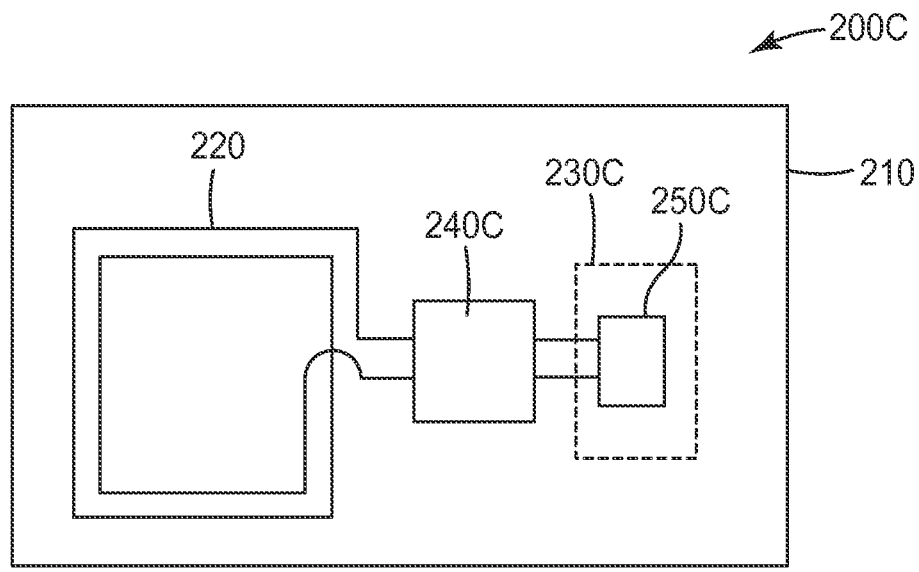
FIG. 2C is a simplified schematic of one embodiment of a wireless sensing device.

FIG. 2C is a simplified schematic of one embodiment of a wireless sensing device 200C. The wireless sensing device 200C includes a substrate 210, an antenna 220 disposed on the substrate 210, a control circuit 240C, a thermal spreader 230C, and a sensing circuit 250C electronically coupled to the control circuit 240C. The sensing circuit 250C is disposed in the thermal spreader 230C. In some embodiments, the sensing circuit 250C can include a sensor and a thermal source. In some cases, the control circuit 240C regulates the thermal source in the sensing circuit 250C.

Figure 2D:
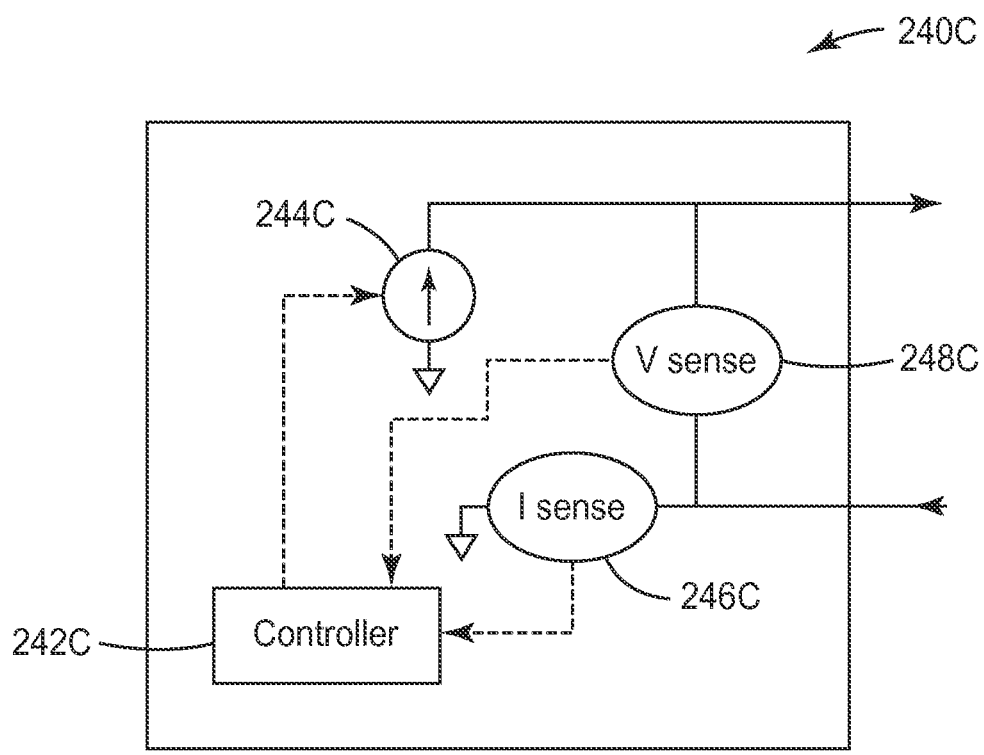
FIG. 2D is a simplified schematic of one embodiment of a power measurement circuit.

In one example illustrated in FIG. 2D, the control circuit 240C comprises a power measurement circuit to facilitate regulating the thermal source. The power measure circuit includes a controller 242C, a power source 244C, a voltage sensor 248C connected to the thermal source, a current sensor 246C connected to the thermal source. The power delivered to the thermal source is calculated by multiplying the sensed current by the sensed voltage. If this calculated power is above or below the desired power level, the power delivered by the power source to the thermal source is accordingly modified by the controller.

Figure 3A:
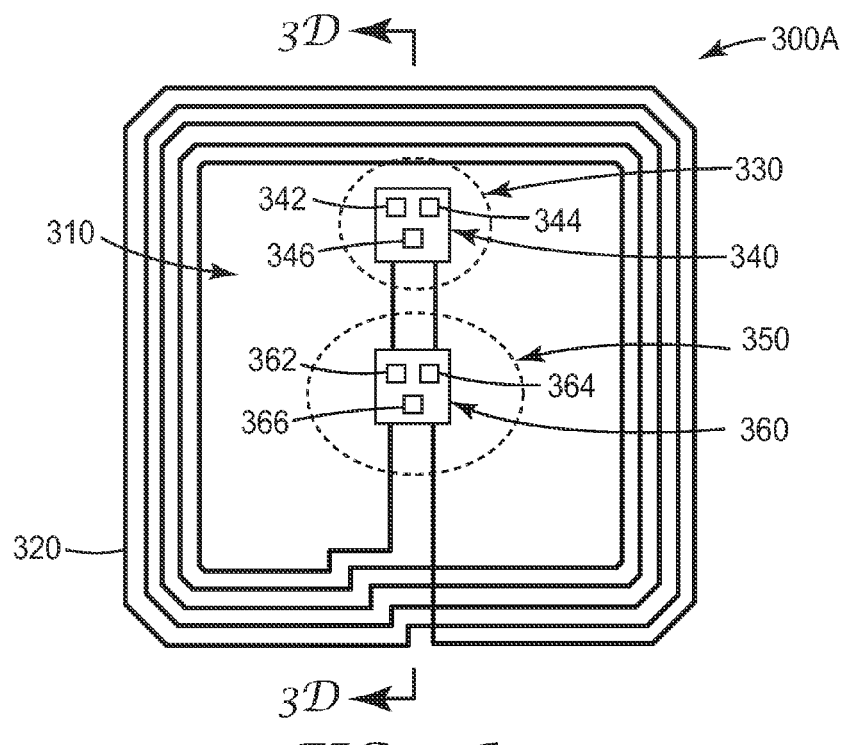
FIGS. 3A-3C illustrate simplified schematics of some embodiments of wireless sensing device with multiple sensors.
Figure 3B:
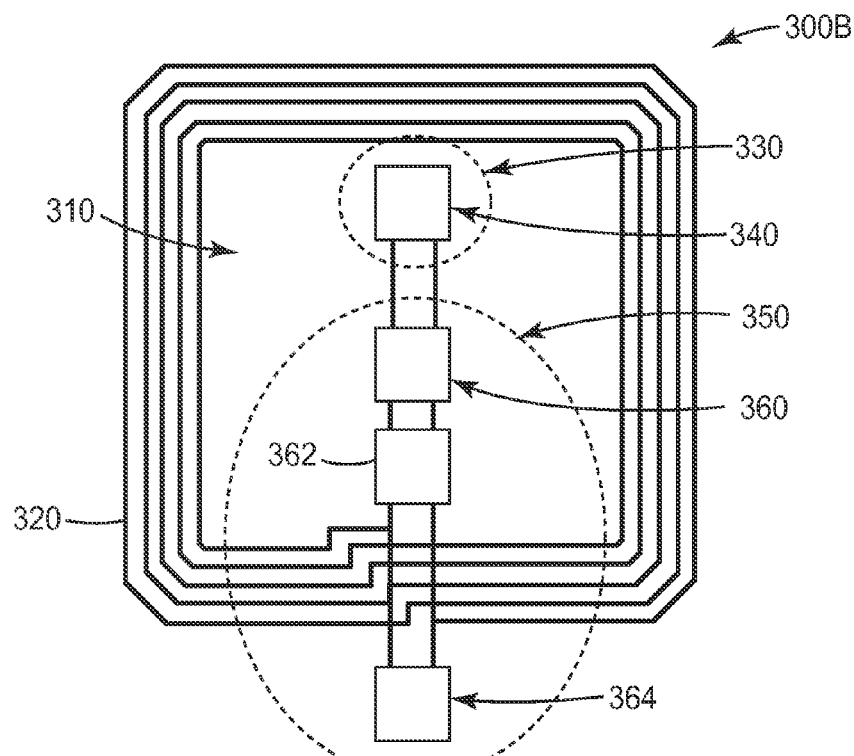
Figure 3C:
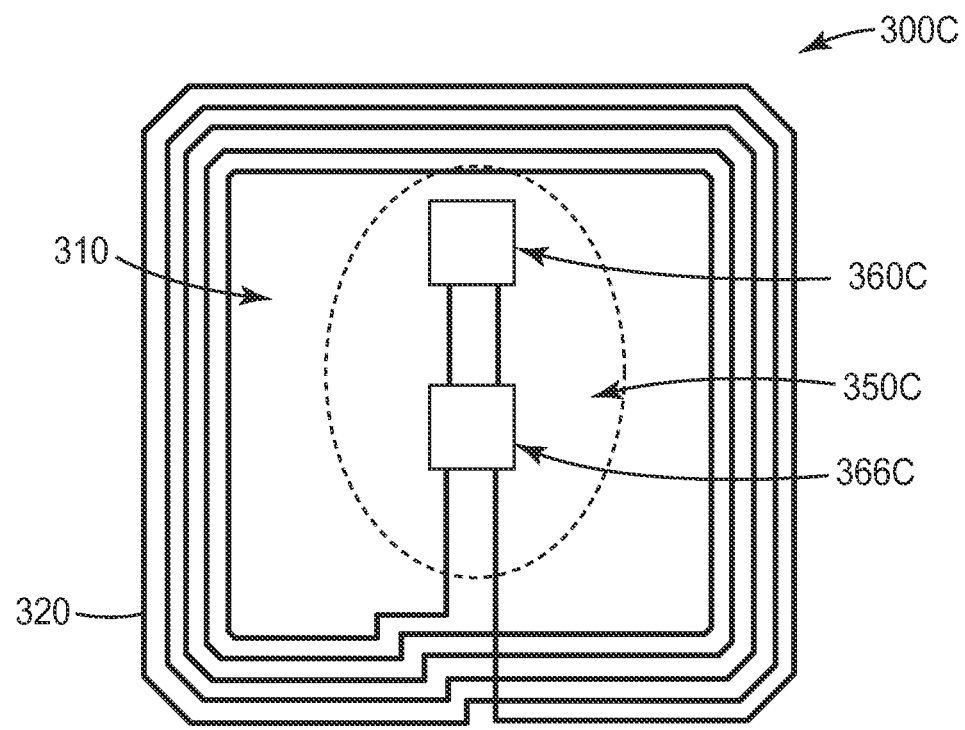
Figure 3D:
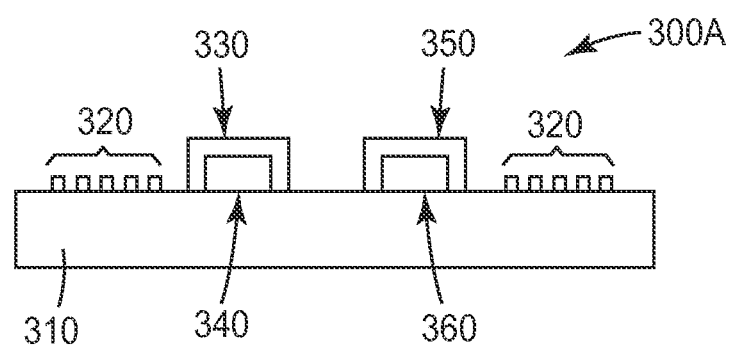
FIG. 3D is a cross-sectional view of the wireless sensing device illustrated in FIG. 3A.

FIGS. 3A-3C illustrate simplified schematics of some embodiments of wireless sensing device with multiple sensors; and FIG. 3D is a cross-sectional view of the wireless sensing device illustrated in FIG. 3A. The RF sensor tag 300A, or referred to as wireless sensing device, as illustrated in FIG. 3A, includes a substrate 310, an antenna 320, an optional first thermal spreader 330, a first sensing circuit 340 and electronically coupled to the antenna 320, an optional second thermal spreader 350, and a second sensing circuit 360 electronically coupled to the antenna 320. The first thermal region 330 and the second thermal region 350 are thermally isolated from each other. The first and/or second sensing circuit (340, 360) can include one or more components of transceiver, control circuit, energy harvesting device, energy storage device, thermal source, and sensor. In one embodiment, the sensing circuit 340 provides a reference sensing signal, while the sensing circuit 360 is in thermal contact with the object of interest and provides sensing signals indicating temperature. In some cases, the induced heating will lead to a larger temperature rise on the thermally isolated region 330 than on the thermal region 350 that is in thermal contact with the object, allowing differential measurement that accounts for the variation in input power to the thermal source. For example, in the case of an a wireless sensing device comprising an RFID tag for use with an RF reader, the input power available may vary with RF reader magnetic field parameters, RFID tag resonance frequency relative to the RF reader frequency, variation in parameters with environmental factors, or other factors.

In some cases, the first sensing circuit 340 includes a first IC 342 disposed on the substrate and the second sensing circuit 360 includes a second IC 362, where each IC is electrically coupled to the antenna 320. In some implementations, the first sensing circuit 340 includes a first heating element 344 and the second sensing circuit 360 includes a second heating element 364, where each heating element heats a respective first and second target area and is electrically coupled to the respective first and second ICs (342, 362). In some cases, each of the first and second target areas has a thermal characteristic, where the thermal characteristic of the first target area is known and the thermal characteristic of the second target area is unknown. In some cases, the first target area is disposed on the substrate 310 and thermally coupled to the first heating element 344, where the first heating element and the first target area are thermally isolated from the second heating element and adapted to be thermally isolated from the second target area.

In some embodiments, the first sensing circuit 340 includes a first temperature sensing element 346 and the second sensing circuit 360 includes a second temperature sensing element 366, where each sensing element (346, 366) is thermally coupled to the respective first and second heating elements (344, 364) for sensing a temperature of the corresponding heating element (344, 364).

In some embodiments, when the second heating element 364 is thermally coupled to the second target area, the RF sensor tag 300A wirelessly receives an input power having an input form from a transceiver, the first and second ICs (342, 362) transform the input power to respective first and second powers having respective first and second forms different from the input form and deliver the first and second powers to the corresponding heating element (344, 364). In some cases, the first and second sensing elements (346, 366) sense a time variation of the corresponding heating element temperature, and the RF sensor tag 300A wirelessly transmits to the transceiver a thermal characteristic of the second target area based on comparing the time variation of the first and second heating elements temperatures. In some cases, the RF sensor tag 300A includes an IC comprising the first and second ICs (342, 362).

In some cases, the first power and the second power has a known ratio to each other. For example, the magnitude of the first power is equal to the magnitude of the second power. As another example, the magnitude of the first power is one third of the magnitude of the second power. In some cases, the first power and/or the second power has a known ratio to the input power. For example, the magnitude of the first power is one third of the magnitude of the input power. In some embodiments, the input power is in AC form. In some cases, the first form and/or the second form is an AC form. In some other cases, the first form and/or the second form is a DC form.

In the example illustrated in FIG. 3B, the wireless sensing device 300B includes a substrate 310, an antenna 320 disposed on the substrate 310, a first thermal spreader 330, a first sensing circuit 340 disposed in the first thermal spreader 330 and electronically coupled to the antenna 320, a second thermal spreader 350, and a second sensing circuit 360, a third sensing circuit 362, and a fourth sensing circuit 364 disposed in the second thermal spreader 350. The first thermal spreader 330 and the second thermal spreader 350 are thermally isolated. The sensing circuits 360, 362, and 364 are spatially separated. The sensing circuits (340, 360, 362, and 364) can include one or more components of transceiver, control circuit, thermal source, energy harvesting device, energy storage device, and sensor. In one embodiment, the sensing circuit 340 provides a reference sensing signal, while the sensing circuits 360, 362, and 364 are in thermal contact with the object of interest and provides sensing signals indicating temperatures of various parts of the object. In some cases, the sensing circuits 360, 362, and 364 can be placed at any desired location or arbitrary location on a surface or in three-dimensional space.

In the example illustrated in FIG. 3C, the wireless sensing device 300C includes a substrate 310, an antenna 320 disposed on the substrate 310, a first sensing circuit 360C and a second sensing circuit 366C. In some embodiments, the wireless sensing device 300C includes a sensing region 350.

The first and/or second sensing circuit (360C, 366C) can include one or more components of transceiver, control circuit, energy harvesting device, energy storage device, thermal source, and sensor. In some embodiments, the first sensing circuit 360C and the second sensing circuit 366C have a known relative placement. In some cases, the first sensing circuit 360C includes a thermal source and a sensor, while the second sensing circuit 366C includes a sensor but not a thermal source. In such cases, the second sensing circuit 366C can provide a measurement indicating a response to the thermal source activation in the first sensing circuit 360C, in either time domain or frequency domain.

Figure 4A:
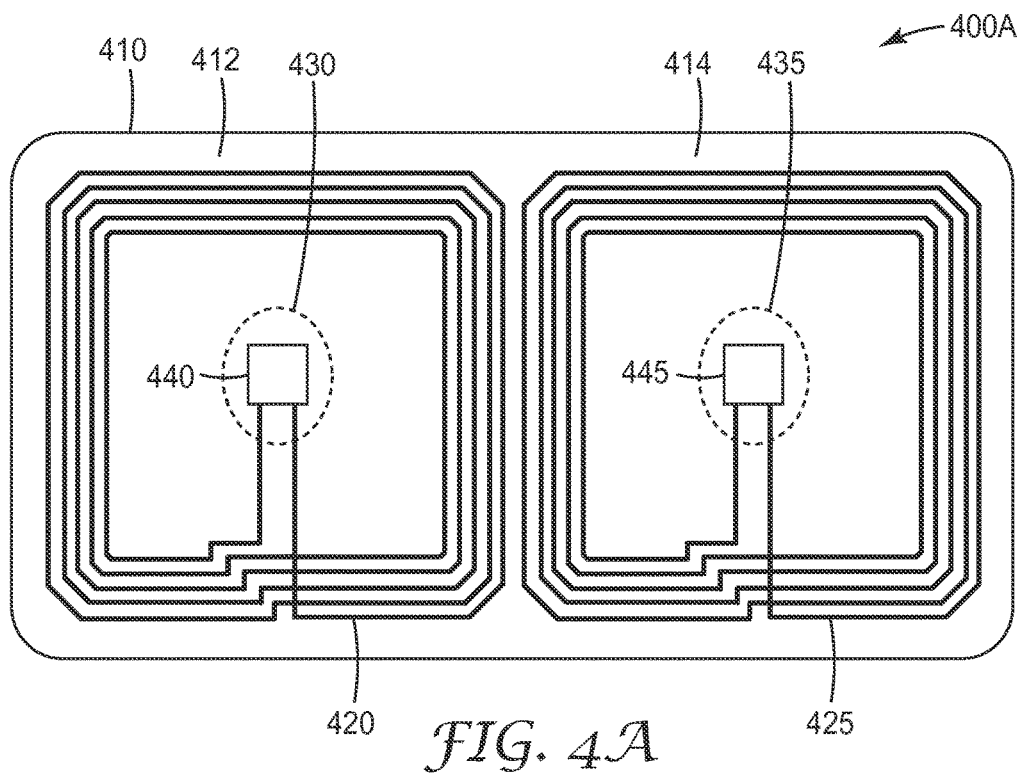
FIGS. 4A and 4B illustrate simplified schematics of some embodiments of a wireless sensing device with multiple sensors and/or multiple RF devices.

FIG. 4A illustrates a simplified schematic of one embodiment of a wireless sensing device with multiple sensors and/or multiple RF devices. The RFID tag 400A, as illustrated in FIG. 4A, includes a substrate 410, a first RF device 412, and a second RF device 414, where both RF devices 412 and 414 are disposed on the substrate 410. The first RF device 412 includes a first antenna 420 and a first circuit 440 electronically coupled to the first antenna 420. In some cases, the first circuit 440 is disposed in an optional first sensing region 430. Similarly, the second RF device 414 includes a second antenna 425 and a second circuit 445 electronically coupled to the second antenna 425. In some cases, the second circuit 445 is disposed in an optional second sensing region 435. The first and/or second circuit (440, 445) can include one or more components of transceiver, control circuit, energy harvesting device, energy storage device, excitation device, and sensor. In one embodiment, the first and second circuits (440 and 445) provide the sensor data of differential or spatial phenomena, where the spatial distribution of the sensors can be controlled via the configuration of the RFID tag 400. The embodiment illustrated in FIG. 4A shows two antennas disposed on a same planar surface. In some cases, two or more antennas coupled with sensing circuits can be disposed on different surfaces, or in a manner that one antenna overlaps with another antenna.

Figure 8A:
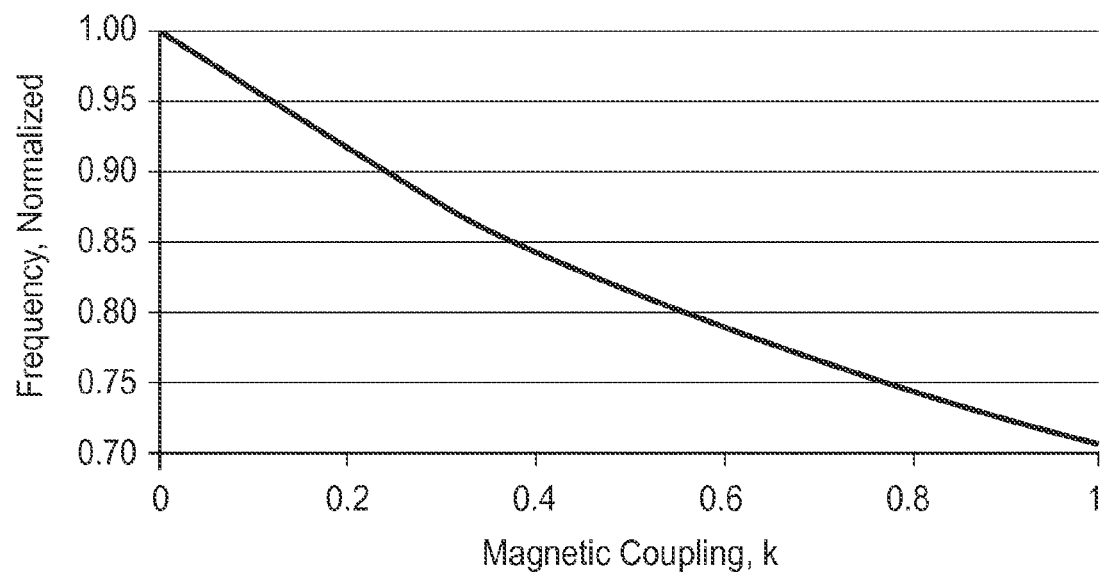
FIG. 8A illustrates a graph of an example of magnetic coupling v. frequency.

In the example illustrated in FIG. 4A, the wireless sensing device incorporates two resonant circuits, which can change the resonating frequency. For example, for two loop antennas with one or more turns of a conductor, in a planar coil configuration, in proximity to one another, the magnetic coupling k, of the two distinct loop antennas can cause resonance to occur at a lower frequency, as illustrated in FIG. 8A. When designing a wireless sensing device containing two resonant circuits, the magnetic coupling can be controlled by the relative orientation between the two circuits. Because the coupling can be controlled, the electronic components can be chosen such that the resultant resonant frequency is within a desired frequency range. For example, for a single resonant circuit of load capacitance of 50 pF, and a desired resultant resonant frequency of 13.56 MHz, Table 1 shows the shift in resonating frequency and inductance change based upon magnetic coupling (k).

TABLE 1

| Capacitance (pF) | Desired Frequency (MHz) | Magnetic Coupling, k | Single Circuit Frequency (MHz) | Inductance of Each Antenna (uH) |
|---|---|---|---|---|
| 50 | 13.56 | 0 | 13.56 | 2.76 |
| 50 | 13.56 | 0.3 | 15.46 | 2.12 |
| 50 | 13.56 | 0.5 | 16.61 | 1.84 |
| 50 | 13.56 | 0.7 | 17.68 | 1.62 |

In some embodiments, the first and second antennas (420, 425) are magnetically coupled to one another. In some cases, the RFID tag 400A is intended to have a pre-determined resonant frequency, each one of the first and second RF devices (412, 414) in the absence of the other one is designed to have a resonant frequency different from the pre-determined frequency resulting in the RFID tag 400A having the pre-determined resonant frequency. In some cases, a magnitude of a magnetic coupling factor of the magnetically coupled first and second antennas (420, 425) is at least 0.1. In some cases, a magnitude of a magnetic coupling factor of the magnetically coupled first and second antennas (420, 425) is between 0.1 and 0.9. In some cases, the resonant frequency of each distinct RF device (412, 414) is different from the tag resonant frequency by at least 5%. In some cases, the RF devices (412, 414) have a same resonant frequency. In one embodiment, the first and second RF devices (412, 414) are configured to wirelessly communicate different first and second information from respective first and second circuits (440, 445) to a same remote transceiver. In one configuration, at least one IC (440 or 445) in the plurality of ICs electrically coupled to only one antenna in the plurality of antennas.

In one embodiment, the first and second circuits (440, 445) are integrated circuits (ICs). In some cases, the first and second antennas (420, 425) are electrically coupled to respective first and second integrated circuits (ICs) (440, 445) disposed on the substrate.

In some cases, the first and second antennas (420, 425) are electrically coupled to a same integrated circuits (IC) disposed on the substrate. In some cases, each of the ICs (440, 445) have a distinct identification number.

In some configurations, the first and second antennas (420, 425) are vertically offset relative to one another in a direction perpendicular to the substrate. In some cases, each of the first and second antennas (420, 425) is substantially overlapping the other of the first and second antennas. In some embodiments, the first and second antennas (420, 425) are substantially identical.

Figure 4B:
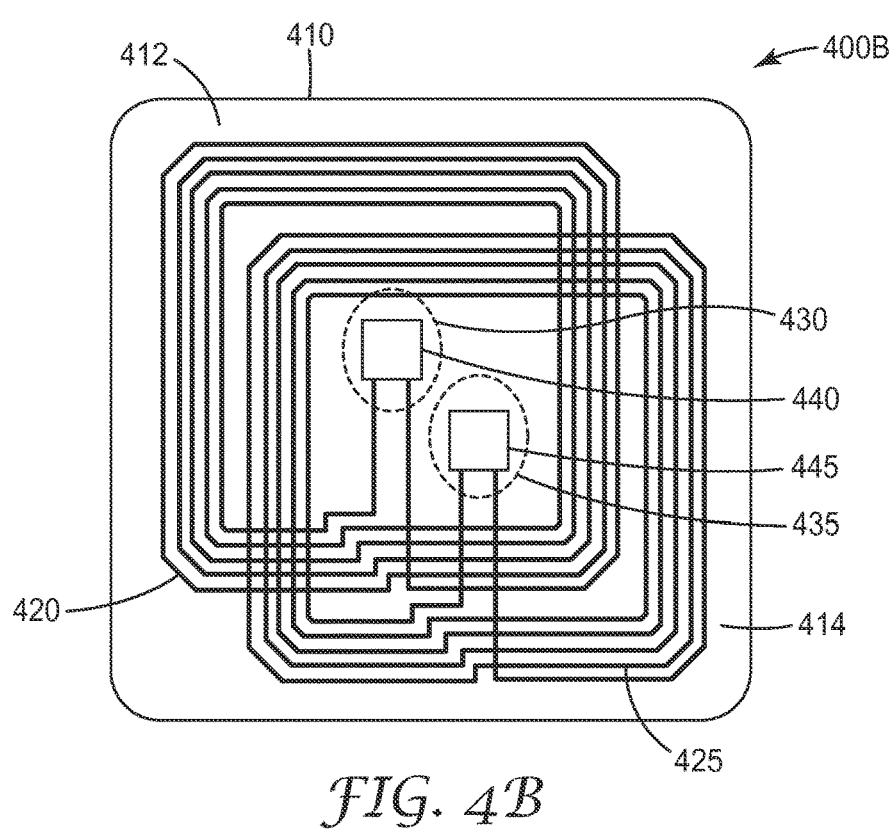

In the example illustrated in FIG. 4B, in plane view, the first and second antennas (420, 425) overlap one another. In some configurations, the substrate 410 has a top surface area enclosed by an outermost perimeter of the substrate, and in plane view, the first and second antennas (420, 425) extend over a majority of the top surface area of the substrate.

Figure 5:
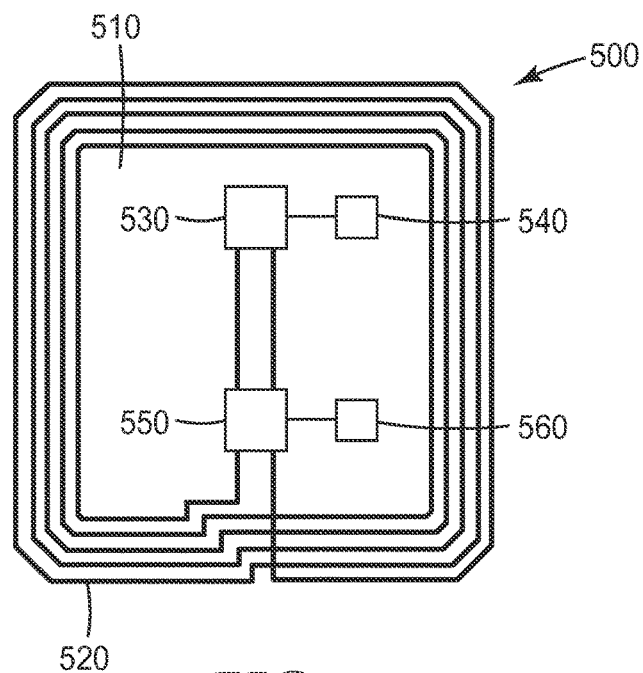
FIG. 5 illustrates a simplified schematic of one embodiment of a wireless sensing device with multiple sensors and a single antenna.

FIG. 5 illustrates a simplified schematic of one embodiment of a wireless sensing device with multiple sensors and a single antenna. The wireless sensing device 500 includes a substrate 510, an antenna 520, a first control circuit 530 electronically coupled to the antenna 520, a first sensing circuit 540 electronically coupled to the first control circuit 530, a second control circuit 550 coupled to the antenna 520, and a second sensing circuit 560 electronically coupled to the second control circuit 550.

The first and/or second control circuit (530, 550) can include one or more components of transceiver, microprocessor, a memory storing a unique identifier, an energy harvesting device, an energy storage device. The first and/or second sensing circuit (540, 560) can include one or more components of excitation devices and sensors. In the embodiment of the sensing circuit including an excitation device, the sensor in the sensing circuit generates sensing signals before and/or after the excitation device is activated. In some embodiments, the first and second sensing circuits (540 and 560) provide sensing signals in response to the sensor data of differential or spatial phenomena, where the spatial distribution of the sensors can be controlled via the configuration the wireless sensing device 500.

Figure 6A:
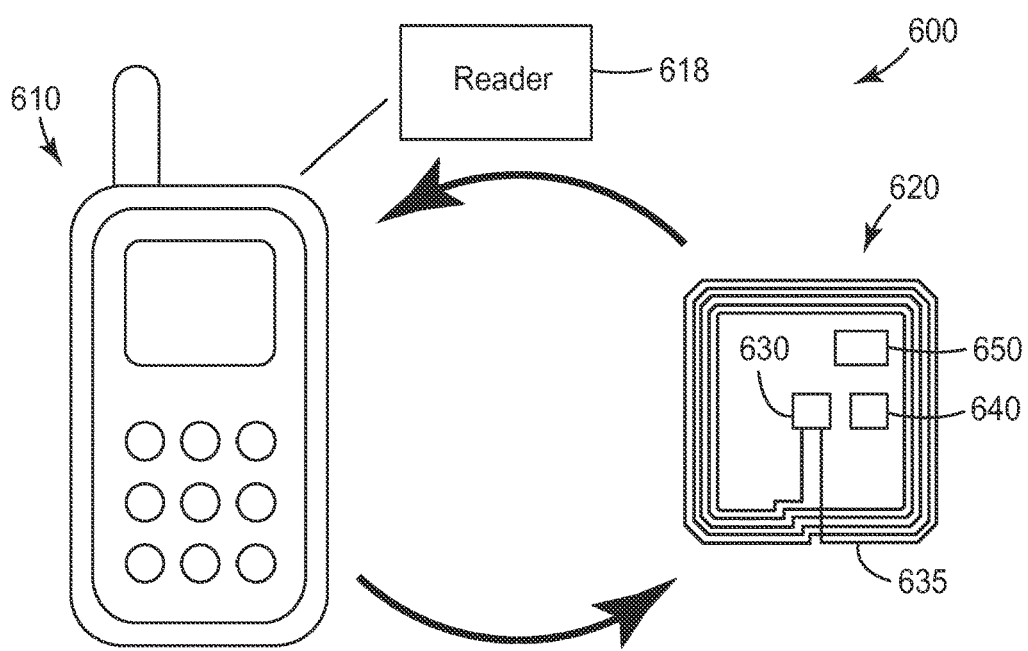
FIG. 6A illustrates one embodiment of a mobile sensing system.

FIG. 6A illustrates one embodiment of a mobile sensing system 600. The mobile sensing system 600 includes a mobile device 610 and one or more wireless sensing devices 620. The wireless sensing device 620 can use any one or combination of the wireless sensing device configurations described in the present disclosure. In the embodiment illustrated, the wireless sensing device 620 includes an antenna 635, an energy harvesting device 630, an excitation device 640, and a sensor 650. In some cases, the energy harvesting device 630 is electronically coupled to the excitation device 640 to provide power to the excitation device 640. In some embodiments, the wireless sensing device 620 is configured to measure a thermal property of the object and transmit a data signal associated with temperature when the wireless sensing device is interrogated. For example, the wireless sensing device 620 is in thermal contact with an object of interest. As another example, the wireless sensing device 620 is a wearable electronic device that will be in close proximity with human skin when it is worn. A reader 618 is connected to or integrated with the mobile device 610, which is configured to interrogate the wireless sensing device and receive the data signal. The processor (not illustrated in FIG. 6A) in the mobile device 610 is electronically coupled to the reader. The processor is configured to determine the thermal property of the object based on the data signal.

In some embodiments, the excitation device can be regulated by power modulation from the energy harvesting device 630 or an intentional radiation source. In some cases, the wireless sensing device 620 is a radio frequency (RF) sensing device and the reader 618 is an RF reader. In some implementations, the RF reader can alter the duty cycle and/or amplitude of its electromagnetic field output to selectively change the amount of power applied to the wireless sensing device 620. As another example, the mobile device 610 may provide a light source to the wireless sensing device 620. In such example, a mobile device LED can alter the duty cycle or amplitude of light output directed to the wireless sensing device 620. Such modulation can be done based on sensing information or power information or both communicated back to the reader 618 or mobile device 610. Alternatively, such modulation can be done based on measurements of the impedance by an RF reader. In some cases, various parameters of measured impedance such as resonance frequency, resonance quality factor, and maximum value of the impedance magnitude can be used to infer the amount of power being transferred into the wireless sensing device 620; this inference could be important due to variables such as coupling between reader and circuit based on geometry, alignment, and relative orientation, and on changes of the resonance parameters due to environmental factors.

In the example of FIG. 6A, mobile device 610 is illustrated as a mobile phone. However, in other examples, mobile device 610 may be a tablet computer, a personal digital assistant (PDA), a laptop computer, a media player, an e-book reader, a wearable computing device (e.g., a watch, eyewear, a glove), or any other type of mobile or non-mobile computing device suitable for performing the techniques described herein.

Figure 6B:
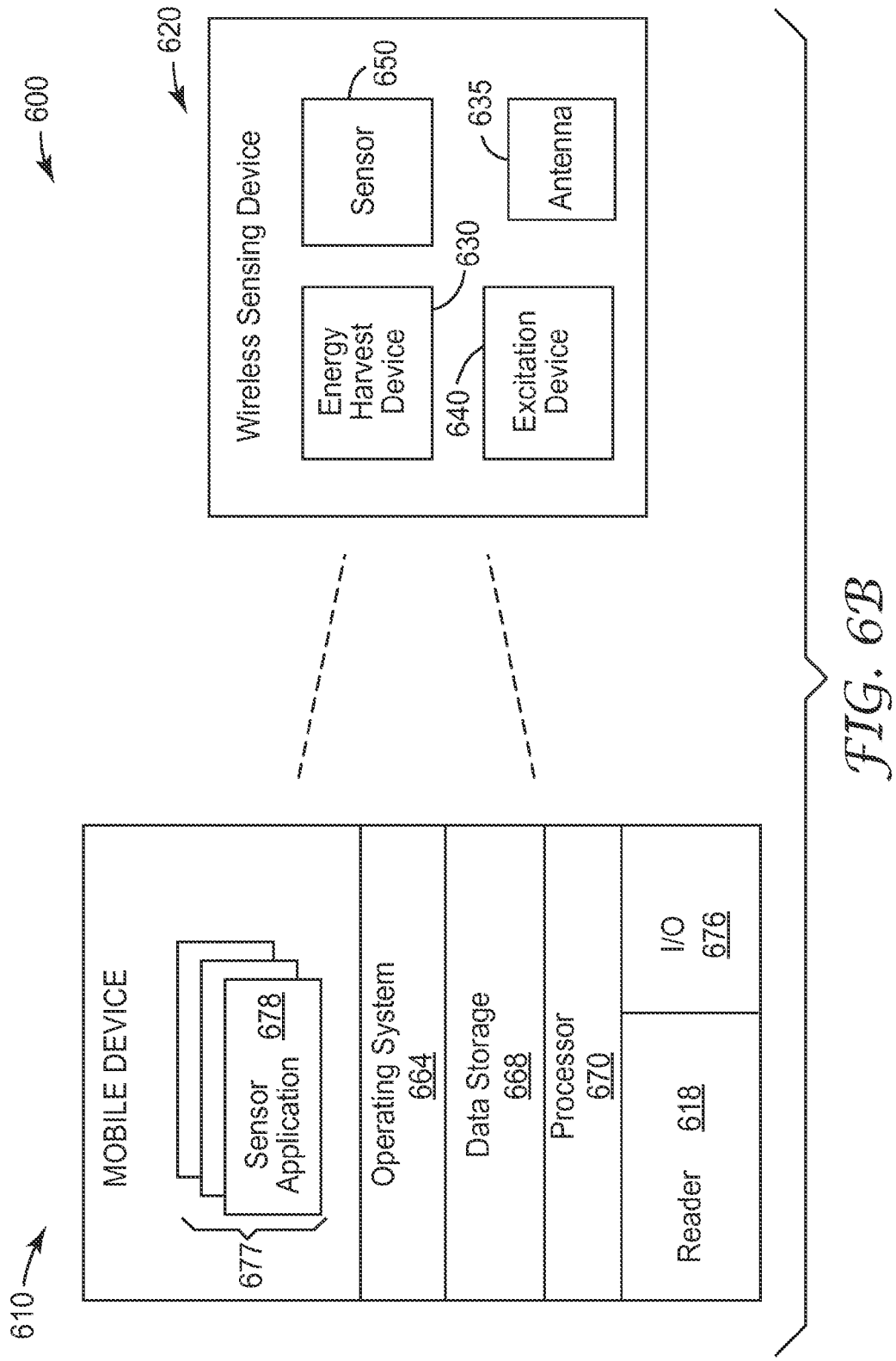
FIG. 6B illustrates a block diagram illustrating an example of a mobile sensing system including a mobile device and a wireless sensing device.

FIG. 6B illustrates a block diagram illustrating an example of a mobile sensing system including a mobile device 610 and a wireless sensing device 620 that operates in accordance with the techniques described herein. For purposes of example, the mobile device of FIG. 6B will be described with respect to mobile device 610 of FIG. 6A, and components for the wireless sensing device 620 with same labels can have same or similar configurations, compositions, functionality and/or relationships as the corresponding components in FIG. 6A.

In this example, mobile device 610 includes various hardware components that provide core functionality for operation of the device. For example, mobile device 610 includes one or more programmable processors 670 configured to operate according to executable instructions (i.e., program code), typically stored in a computer-readable medium or data storage 668 such as static, random-access memory (SRAM) device or Flash memory device. I/O 676 may include one or more devices, such as a keyboard, camera button, power button, volume button, home button, back button, menu button, or presentation device. Mobile device 610 may include additional discrete digital logic or analog circuitry not shown in FIG. 6B.

In general, operating system 664 executes on processor 670 and provides an operating environment for one or more user applications 677 (commonly referred to "apps"), including sensor application 678. User applications 677 may, for example, comprise executable program code stored in computer-readable storage device (e.g., data storage 668) for execution by processor 670. As other examples, user applications 677 may comprise firmware or, in some examples, may be implemented in discrete logic.

In operation, mobile device 610 receives data from the wireless sensing device 620. For example, reader 618 may interrogate the wireless sensing device 620 and receive sensing signals and provide the sensing signals to the processor 670. In general, mobile device 610 stores the sensor data in data storage 668 for access and processing by sensor application 678 and/or other user applications 677.

Thermal properties of an object or a material can be determined based on data collected by thermal sensors, for example, in a sensing system illustrated in FIG. 6A, or a sensing device illustrated in FIG. 1A. For example, the thermal conductivity, thermal diffusivity, and heat capacity of a material in thermal contact with a thermal source can be determined by knowing the input power and the temperature profile as a function of time along with calibration information including an analysis framework and parameters related to geometry, other material properties, and the like. The effective thermal properties of composite material can similarly be determined.

Figure 8B:
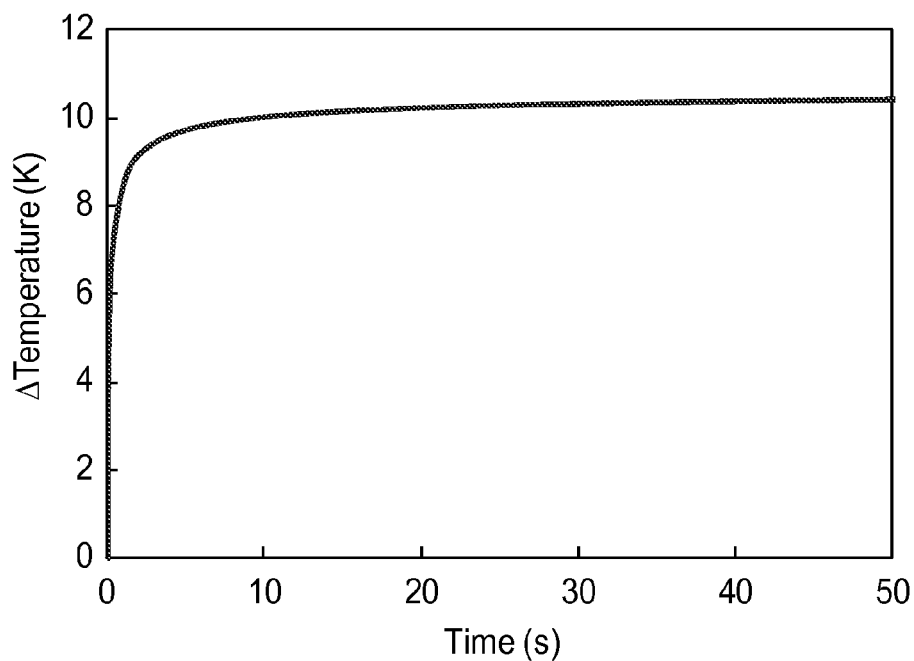
FIG. 8B illustrates an example of temperature-time profile.

One method to calculate the thermal conductivity and thermal diffusivity of material in thermal contact with a thermal source is by using the transient plane source (TPS) analysis. This method is commonly employed when the thermal source can be represented as a plane source. The experiment consists of applying power to a thermal source and measuring the power and temperature-time profile. An example measured temperature-time profile is shown in FIG. 8B. The transient heating of a square plane has been shown to follow Equation (1):

$$\Delta T(\tau) = \frac{P_o}{4a * \text{sqrt}(\pi) * k} H(\tau), \quad (1)$$

where $\Delta T(\tau)$ is the average temperature rise of the heater, $P_o$ is the applied power, $2a$ is the length of one side of the square thermal source, k is the isotropic thermal conductivity of material in thermal contact of the heater, $H(\tau)$ is the dimentionless specific time constant, and $\tau$ is defined in Equation (2):

$$\tau = \left(\frac{\alpha t}{a^2}\right)^{1/2}, \quad (2)$$

where α is thermal diffusivity of the material is thermal contact with the heater and t is time. The H(τ) is the dimentionless specific time constant and can be calculated as Equation (3):

$$H(\tau) = \int_0^\tau d\upsilon \left\{ \text{erf}(\upsilon^{-1}) - \pi^{-\frac{1}{2}}\upsilon[1 - \exp(-\upsilon^{-2})] \right\}^2 \quad (3)$$

The thermal conductivity can be determined from Equation (4):

$$k = \frac{P_o}{4a * \text{sqrt}(\pi) * \Delta T_{ss}} H(\tau = \infty), \quad (4)$$

where $\Delta T_{ss}$ is the steady state temperature change. According to FIG. 8B, the steady state temperature change is the 10.59° C. With a=0.0025 m, a constant applied power of 0.01 W, and H(τ=∞) the thermal conductivity of the surrounding material is calculated to be 0.044 W/mK.

The thermal diffusivity can be calculated from the full temperature-time response through an iterative method to fit Equation (1) to the data set in FIG. 8B with a least-squares fitting method (other methods can be used). With this method, the thermal diffusivity was determined to be 20×10$^{-6}$ m²/s.

The heat capacity ($C_p$) of the surrounding material can be calculated if the surrounding material's density is known according to Equation (5)

$$C_p = \frac{k}{\rho \alpha}, \quad (5)$$

For example, if the density of the surrounding material is 1200 g/m³, then the heat capacity is 1.83 J/gK of the surrounding material. More information on thermal property measurements can be found, for example, in a journal article by Gustafsson S. E., *Transient plane source techniques for thermal conductivity and thermal diffusivity measurements of solid materials*, Rev. Sci. Instrum., Volume 62, pp. 797-804, 1991, which is incorporated by reference in its entirety.

Figure 6C:
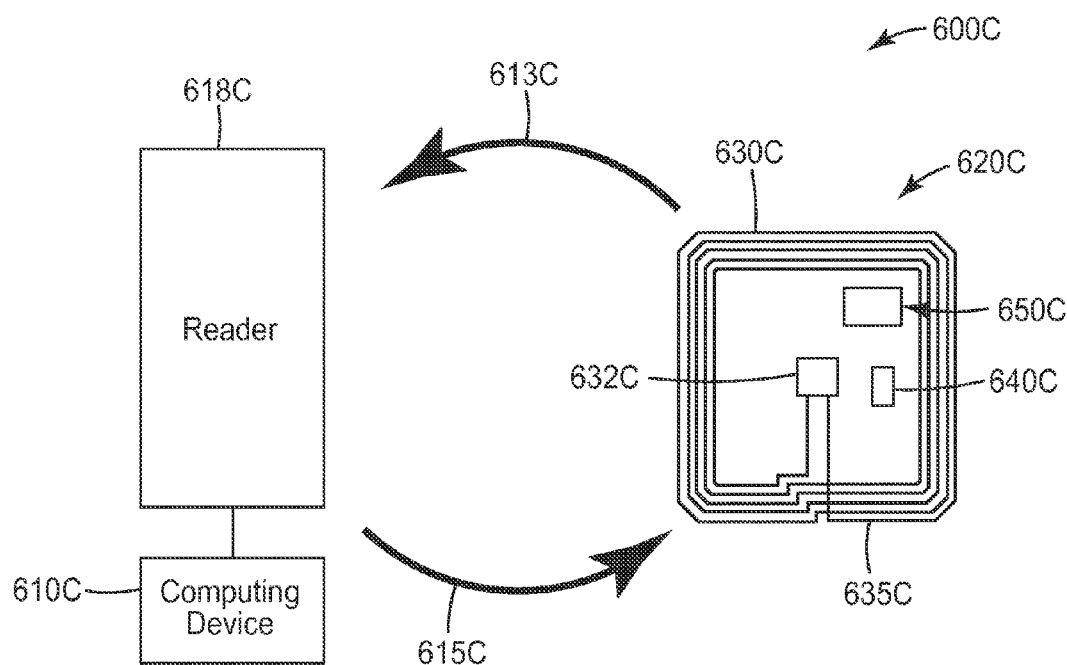
FIG. 6C illustrates one embodiment of a wireless sensing system.

FIG. 6C illustrates one embodiment of a wireless sensing system 600C. The wireless sensing system 600C includes a reader 618C and one or more wireless sensing devices 620C (i.e., one sensing device illustrated), which can measure a physical property of an object. In some cases, the wireless sensing system 600C includes a computing device 610C, where the reader 618C is connected to or integrated with the computing device 610C. The computing device 610C can include one or more processors, microprocessors, computers, servers, and other peripheral devices. The wireless sensing device can use any one or combination of the wireless sensing device configurations described in the present disclosure. In the embodiment illustrated, the wireless sensing device 620C includes a wireless device 630C including a wireless transceiver 632C and an antenna 635C electronically coupled to the wireless transceiver 632C, an excitation device 640C, and a sensor 650C electronically coupled to the wireless transceiver 632C. In some cases, the antenna 635C is electronically coupled to the excitation device 640C to provide power to the excitation device 640C. In some other cases, the reader 618C transmits an activation signal 615C to the wireless sensing device 620C to activate the excitation device 640C. In some embodiments, the sensor 650C generates a sensing signal associated with the physical property of the object, and the wireless transceiver 632C is configured to transmit a data signal 613C associated with the sensing signal via the antenna 635C. The reader 618C is configured to receive the data signal 613C. In some embodiments, the computing device 610C is configured to determine the physical property of the object based on the data signal 613C. In some implementations, the reader 618C is further configured to adjust the activation signal 615C based on the data signal 613C.

As an example, the wireless sensing device 620C includes a thermal source 640C and a thermal sensor 650C, where the thermal source 640C and thermal sensor 650C are in thermal contact with the object of interest. In some cases, the wireless sensing device 620C can use a temperature dependent resistor as both the thermal source 640C and the thermal sensor 650C. When power is delivered to this resistor, it produces thermal energy, and a measure of resistance of this same resistor can be used to measure temperature. It can be beneficial to deliver a relatively large amount of power to this resistor when using it to produce a thermal excitation. Relatively little power can be delivered to the resistor when measuring the resistance of this resistor to minimize heating during temperature measurements.

Figure 8C:
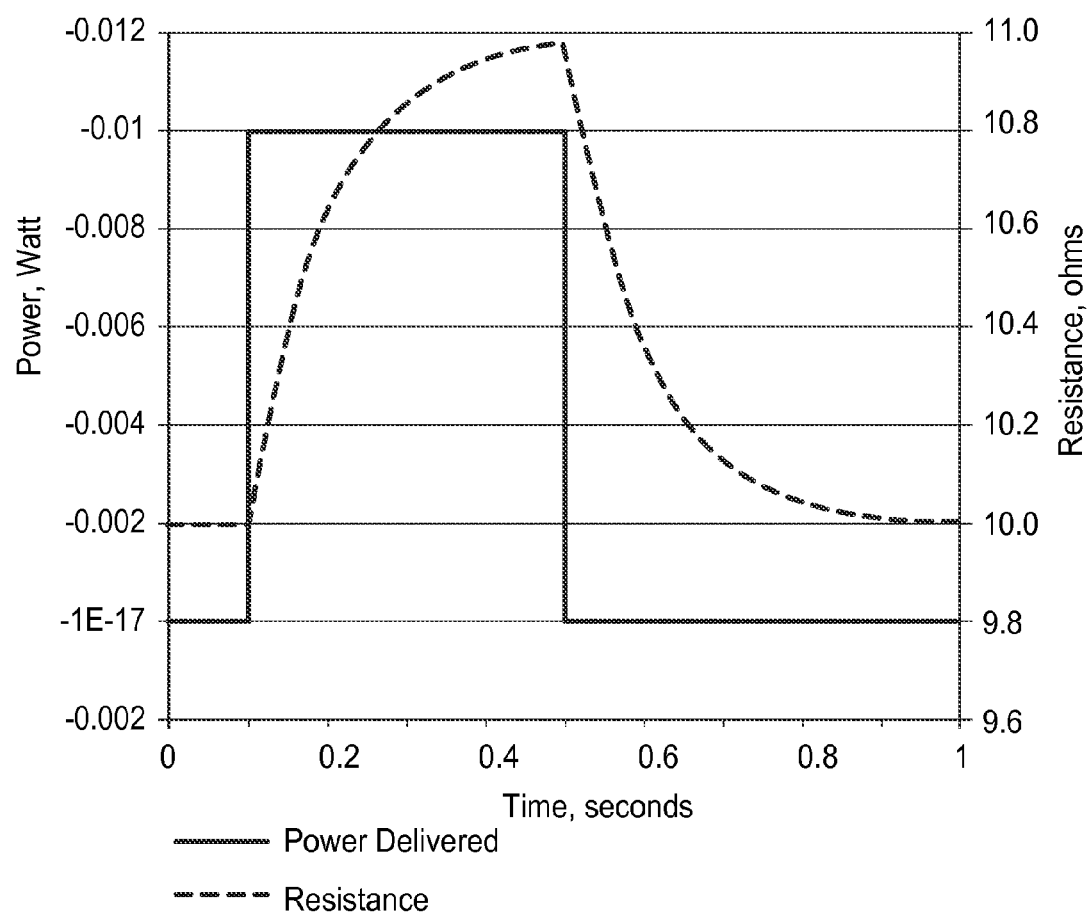
FIG. 8C is a concept example that indicates the usefulness of controlling the power delivered to a thermal source.

Controlling the power delivered to this resistor can be useful to determine thermal properties of the object to which the wireless sensing device is attached. FIG. 8C is a concept example that indicates the usefulness of controlling the power delivered to a thermal source. This example includes three sequential time intervals: time interval 1 from 0 to 0.1 s, time interval 2 from 0.1 to 0.5 s, and time interval 3 from 0.5 to 1.0 s. During time intervals 1 and 3, the power delivered to the resistor is relatively small, but adequate to measure the resistance to determine temperature. During time interval 2, the power delivered to the resistor is relatively large, i.e., 10 mW. During time interval 2 the resistance of the resistor can be seen to increase from 10 ohms to nearly 11 ohms. During time interval 3 the resistance of the resistor can be seen to decrease from nearly 11 ohms down to slightly above 10 ohms. Thermal properties such as conductance, capacity and diffusivity can be determined from these types of curves, such as using the TPS analysis described.

In some embodiments, the reader 618C and/or a control circuit in the wireless sensing device 620C controls the magnitude of the excitation (i.e. power supply to the excitation device) over time. In some cases, the reader 618C and/or a control circuit in the wireless sensing device 620C controls the excitation in response to the measured sensor signal changes over time. For example, if the change in the sensor signal is not adequate, the reader 618C and/or a control circuit in the wireless sensing device 620C may increase the magnitude or duration of the excitation; and if the change in the sensor signal is large, the reader 618C and/or a control circuit in the wireless sensing device 620C may reduce the magnitude or duration of the excitation, for example, to ensure that the response remains within the dynamic range of the sensing system. In some cases, the reader 618C and/or a control circuit in the wireless sensing device 620C controls the excitation by providing a constant power with known value or a known power-time profile.

Figure 6D:
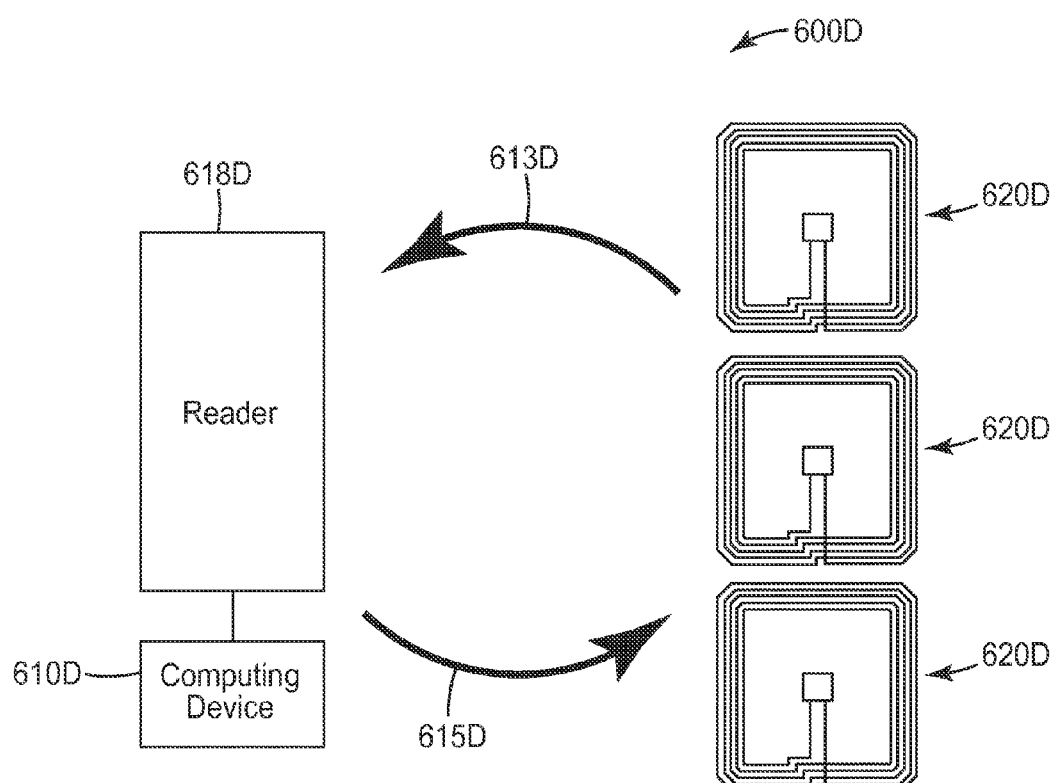
FIG. 6D illustrates one embodiment of a wireless sensing system having more than one wireless sensing devices.

FIG. 6D illustrates one embodiment of a wireless sensing system 600D having more than one wireless sensing devices. The wireless sensing system 600D includes a reader 618D and three or more sensing devices 620D. In some cases, the wireless sensing system 600D includes a computing device 610D, where the reader 618D is connected to or integrated with the computing device 610D. The computing device 610D can include one or more processors, microprocessors, computers, servers, and other peripheral devices. The sensing device 620D can use any one or combination of the wireless sensing device configurations described in the present disclosure. In some embodiments, the reader 618D is configured to transmit an activation signal to at least some of the sensing devices 620D to activate the excitation devices (not illustrated) in the sensing devices 620D. In addition, the reader 618D is configured to receive data signals from the sensing devices 620D. In some cases, at least some of the sensing devices 620D are disposed in different locations from each other. In some configurations, the reader 618D is configured to coordinate the transmission of the activation signal to each of the sensing devices 620D in a pattern related to the location of the sensing device 620D, for example, activate excitation devices individually, simultaneously, or other temporal or spatial patterns.

In some embodiments, at least some of sensing devices 620D are disposed proximate to an object, and the computing device 610D is configured to determine the physical property of the object based on the data signals generated by the sensing devices 620D. In some cases, at least one of the sensing devices 620D is configured to transmit a reference data signal corresponding to a reference sensor signal independent from the physical property of the object, and the computing device 610D determines the physical property of the object using the reference data signal.

In some embodiments, some of the sensing devices 620D include only excitation device but no sensor, also referred to as actuation device. In some cases, an actuation device is disposed at a different location from a sensing device that includes a sensor. In such embodiments, the reader 618D is configured to transmit an activation signal 615D to the actuation device to activate the excitation device and receive the data signal 613D from the sensing device.

Figure 7A:
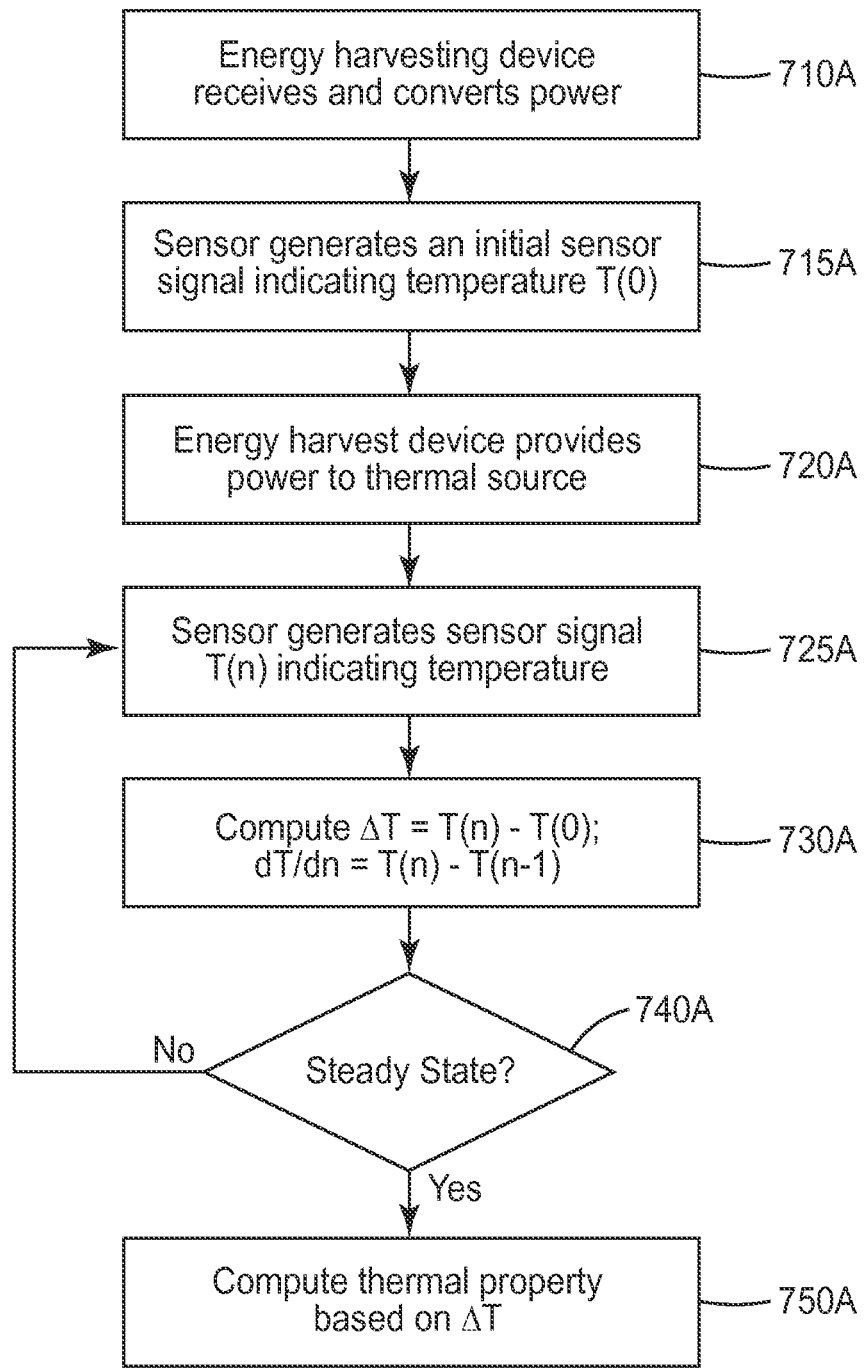
FIG. 7A illustrates an example flowchart for the operation of one embodiment of a wireless sensing device and/or system.

FIG. 7A illustrates an example flowchart for the operation of one embodiment of a wireless sensing device and/or system, for example, the wireless sensing device illustrated in FIG. 1A or the wireless sensing system illustrated in FIG. 6A. First, the energy harvesting device receives and converts power (step 710A). Next, the sensor generates an initial sensor signal indicating temperature $T(0)$ (step 715A). The energy harvesting device provides power to the thermal source (step 720A), which may also occur nearly simultaneously with step 715A in either order. Then, the sensor generates sensor signal indicating temperature $T(n)$ (step 725A). The control circuit in the wireless sensing device or a computing device that receives the sensor signal computes a signal indicating temperature difference $\Delta T=T(n)-T(0)$ and a signal indicating temperature rate of change $dT/dn=T(n)-T(n-1)$ (step 730A). The control circuit or the computing device determines whether a thermal steady state is reached, where $dT/dn$ is less than or equal to a predetermined threshold and/or other conditions. If the steady state is not reached, the sensor continues to generate sensor signal $T(n)$ indicating temperature (step 725A). If the steady state is reached, the control circuit or the computing device computes thermal property based on $\Delta T$ (step 750A), and may deactivate the thermal source.

Figure 7B:
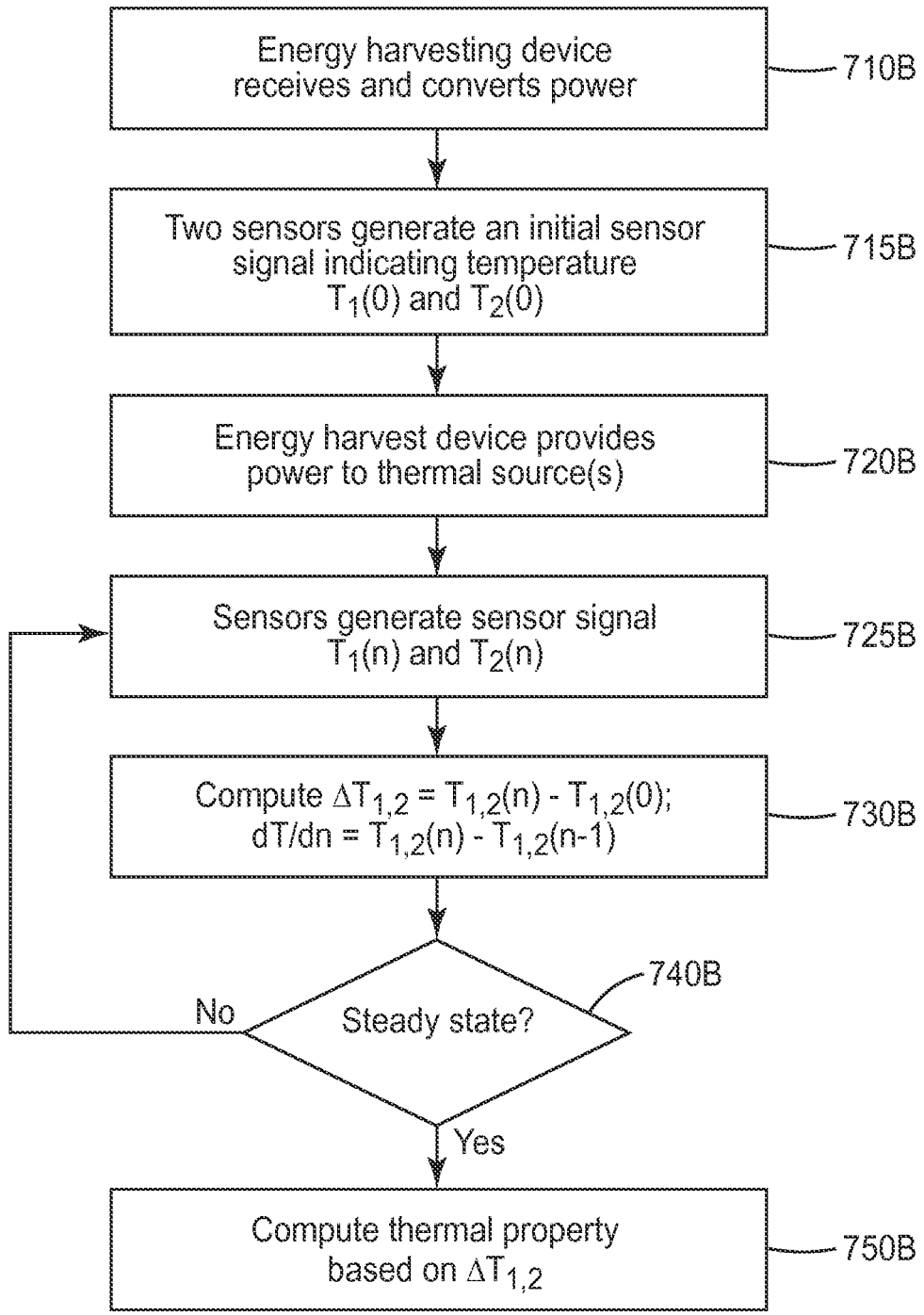
FIG. 7B illustrates an example flowchart for the operation of one embodiment of a wireless sensing device or system having two sensors.

FIG. 7B illustrates an example flowchart for the operation of one embodiment of a wireless sensing device or system having two sensors, for example, the wireless sensing device illustrated in FIG. 1B or the wireless sensing system illustrated in FIG. 6D. In some embodiments, more than two sensors can be included in the wireless sensing device or system to determine thermal property using similar steps. First, the energy harvesting device receives and converts power (step 710B). Next, two sensors generate an initial sensor signals indicating temperature $T_1(0)$ and $T_2(0)$ (step 715B). The energy harvesting device provides power to the thermal source(s) (step 720B), which may also occur nearly simultaneously with step 715B in either order. Then, the sensors generate sensor signals indicating temperatures $T_1(n)$ and $T_2(n)$ indicating temperature (step 725B). The control circuit in the wireless sensing device or a computing device that receives the sensor signals computes signals indicating temperature differences relative to initial temperatures measured by the two sensors respectively ($\Delta T_1=T_1(n)-T_1(0)$, $\Delta T_2=T_2(n)-T_2(0)$) and signals indicating temperature change rates measured by the two sensors respectively ($dT_1/dn=T_1(n)-T_1(n-1)$, $dT_2/dn=T_2(n)-T_2(n-1)$) (step 730B). The control circuit or the computing device determines where a thermal steady state is reached, where $dT_1/dn$ and/or $dT_2/dn$ are less than a predetermined threshold and/or other conditions. If the steady state is not reached, the sensors continue to generate sensor signals $T_{1,2}(n)$ (step 725B). If the steady state is reached, the control circuit or the computing device computes one or more thermal properties based on $\Delta T_{1,2}$ (step 750B), and may deactivate the thermal source.

Figure 9A:
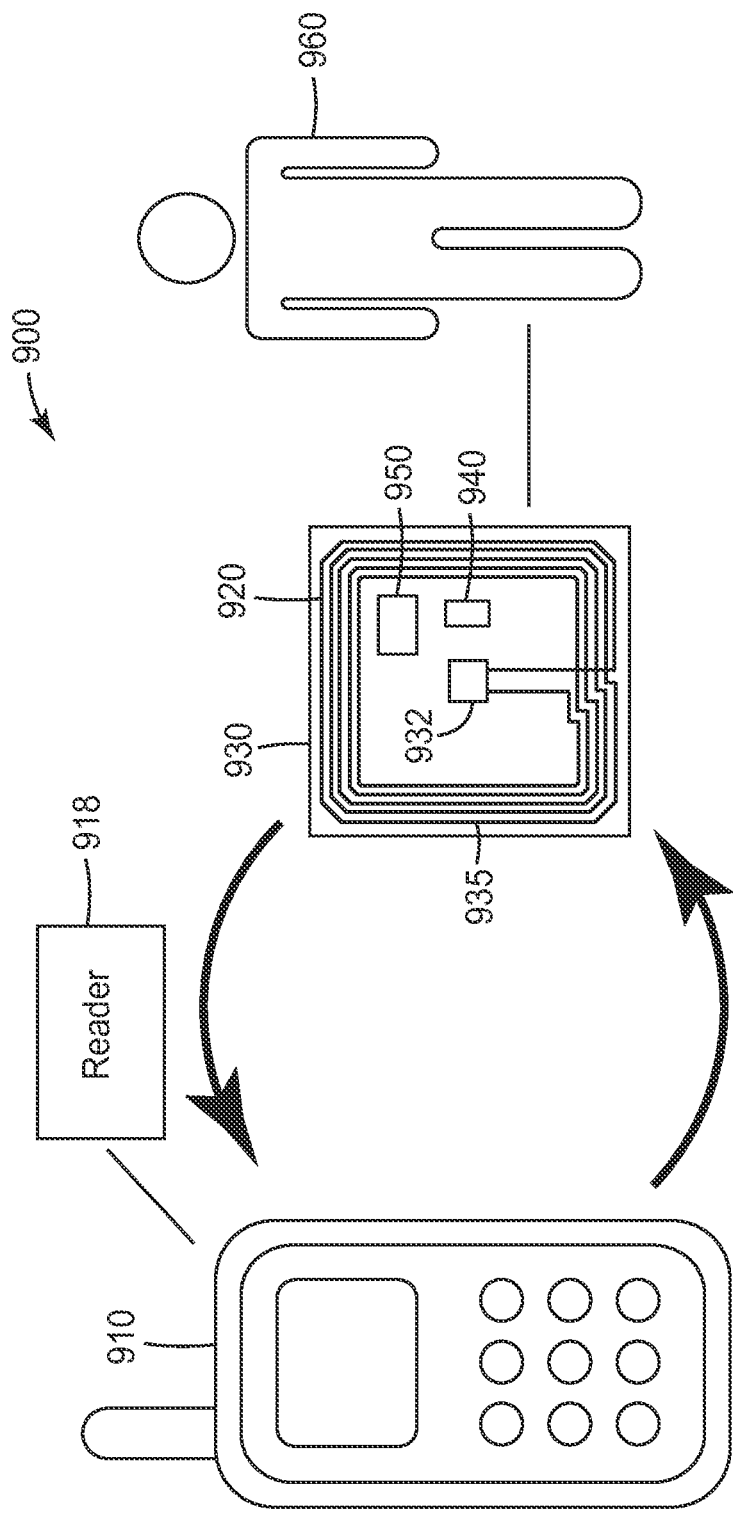
FIG. 9A illustrates one embodiment of hydration sensing system.

FIG. 9A illustrates one embodiment of hydration sensing system 900. The hydration sensing system 900 includes a computing device 910, a reader 918 and one or more wireless sensing devices 920, which can be disposed in thermal contact with the skin of a person 960 or can be used to determine liquid content of a material. In some cases, the reader 918 is connected to or integrated with the computing device 910. The computing device 910 can include one or more processors, microprocessors, computers, servers, and other peripheral devices. The wireless sensing device 920 can use any one or combination of the wireless sensing device configurations described in the present disclosure. In the embodiment illustrated, the wireless sensing device 920 includes a substrate 930, a RF circuit 932, an antenna 935 disposed on the substrate 930 and electronically coupled to the RF circuit 932, a thermal source 940, and a sensor 950 thermally coupled to the thermal source 940 for sensing a temperature of the thermal source 940. In some embodiments, when the thermal source 940 is thermally coupled to a target area, the wireless sensing device 920 wirelessly receives a first power having a first form from a transceiver, the RF circuit 932 transforms the first power to a second power having a second form different from the first form and delivers the second power to the thermal source 940, the sensor 950 senses a time variation of the thermal source temperature, and the RF circuit 932 wirelessly transmits the sensed time variation of the thermal source temperature. The reader 918 is configured to receive the sensed time variation of the thermal source temperature and the computing device 910 is configured to determine a hydration indicator indicative of hydration level based on the sensed time variation of the thermal source temperature. In some embodiments, the wireless sensing device 920 includes a processor to determine a hydration indicator indicative of hydration level based on the sensed time variation of the thermal source temperature.

Figure 9B:
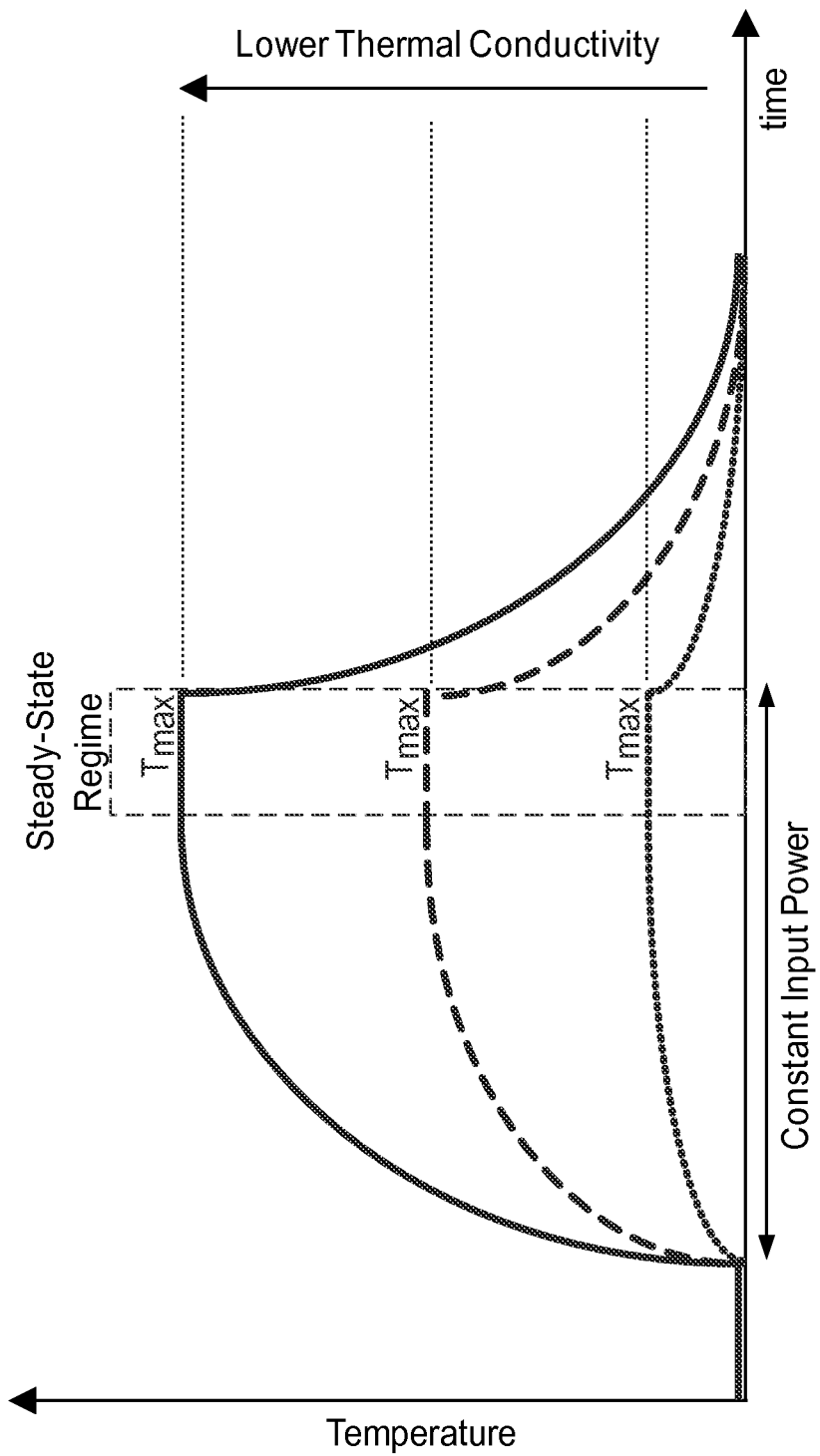
FIG. 9B shows a schematic temperature-time profile of a thermal source before, during, and after a constant input power.

FIG. 9B shows a schematic temperature-time profile of a thermal source before, during, and after a constant input power. The time scale and temperature rise of the profile are a function of the applied power, shape and thermal properties of the thermal source, and thermal properties of the surrounding material in thermal contact with the thermal source. For quantitative thermal measurements, the thermal and geometrical properties of the thermal source are needed. The temperature-time profile can be separated into three distinct regions, as illustrated in FIG. 9B. The first region is the non-steady state heating region where a temperature rise is observed. From this region, the thermal diffusivity of the surrounding material can be determined from the rate of temperature increase. The second region of the profile is the steady state region; the region where a maximum and steady-state temperature is reached. For this region, the thermal conductivity of the surrounding material can be determined. The temperature at steady state varies inversely with the thermal conductivity of the material. The third region is the non-steady state cooling region after removal of the applied power to the thermal source. Similar to first region, the rate of temperature decrease can be used to measure the thermal diffusivity of the surrounding material. FIG. 9B shows a temperature-time profile for a heater, but the embodiments described herein apply to a thermal source as a cooler.

In some cases, the effective thermal properties of a material or an object may be dependent on moisture content. For example, a region of skin like that of a human or other mammal having biological cells and tissues along with a particular fraction of water, where the effective thermal conductivity of the region of skin will vary relative to the ratio of water to tissue in that region. The determination of the moisture (or hydration) level of the skin can be determined through a look-up table or an analytical equation based on the measured value(s) of thermal diffusivity, thermal conductivity, heat capacity, or a combinations thereof, or indices proportional to the value(s). For example, thermal conductivity of the dry human skin can be on the order of 0.2-0.3 W/m-K; thermal conductivity of the normal human skin can be on the order of 0.3-0.4 W/mK; thermal conductivity of the hydrated human skin can be on the order of 0.4-0.55 W/m-K; and thermal conductivity of the human perspiration can be in the range of 0.55-0.7 W/m-K.

For example, an analytical approach, discussed in *Skin Thermal Conductivity A Reliable Index of Skin Blood Flow and Skin* Hydration, A. DITTMAR, Laboratory of Thermoregulation, U.A. 181 C.N.R.S., Lyon, France, Apr. 5, 1989 been reported to measure the moisture content of skin from the thermal conductivity of the skin ($k_{skin}$) through the Equation (6)

$$\% \text{ water content} = \frac{1}{6}(k_{skin} - \%(\text{lipids} + \text{protiens})1.8) \quad (6)$$

Figure 7C:
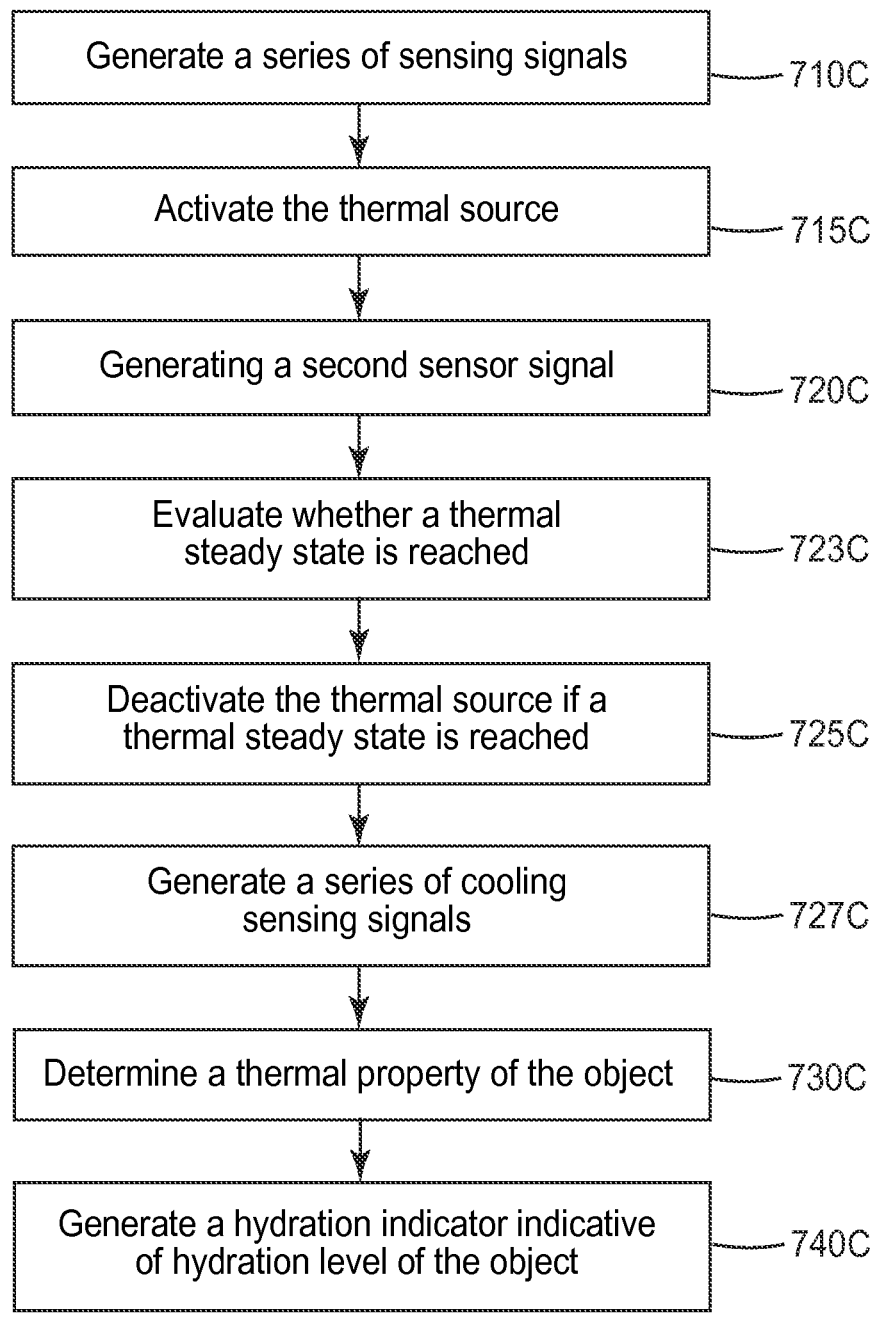
FIG. 7C illustrates an example flowchart to determine a hydration level.

An example flowchart to determine a hydration level using any of the wireless sensing device or any of the wireless sensing system described herein is illustrated in FIG. 7C. Some steps, for example, step 710C, step 727C, are optional steps of the sensing system. First, the wireless sensing device generates a first sensor signal (step 710C), before the thermal source is activated or when thermal source is just activated. Next, the thermal source is activated (step 715C). The wireless sensing device generates a series of sensing signals (step 720C). The wireless sensing device or system determines a thermal property based on at least some of the series of sensing signals (step 730C). The thermal property can include, for example, thermal conductivity, heat capacity, thermal diffusivity, and the like. The wireless sensing device or system further generates a hydration indicator indicative of hydration level of the object based on the determined thermal property and a reference data (740C). The reference data can be an analytical function, a look-up table, a matrix, a constant, or a combination thereof.

In some cases, the wireless sensing device or system evaluates whether a thermal steady state is reached (step 723C), using the series of series signals, for example, the change rate of the sensor signals is smaller than a predetermined threshold. In some cases, the wireless sensing device or system determines a thermal conductivity of the object based on the first sensor signal and the sensor signal generated when or after the thermal steady state is reached, where the hydration indicator is generated based on the thermal conductivity. In some implementations, the thermal source is deactivated after the thermal steady state is reached (step 725C). The sensing device generates a series of cooling sensing signals after the thermal source is deactivated (step 727C). In some cases, the wireless sensing device or system determines a thermal diffusivity of the object based on at least some of the series of cooling sensing signals, where the hydration indicator is generated based on the thermal diffusivity.

Figure 9C:
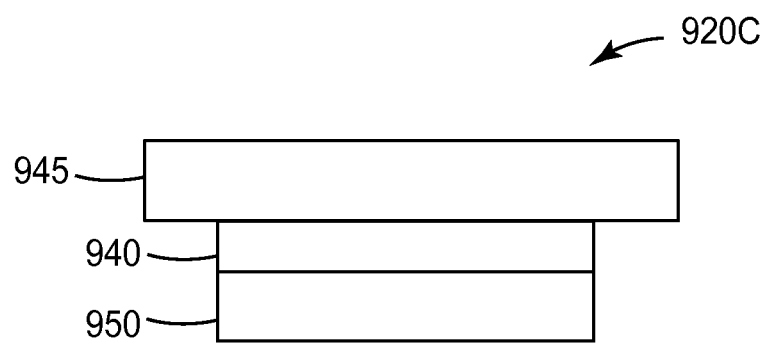
FIG. 9C illustrates a cross-section view of some of the components for one embodiment of a wireless sensing device for measuring a liquid level.
Figure 9D:
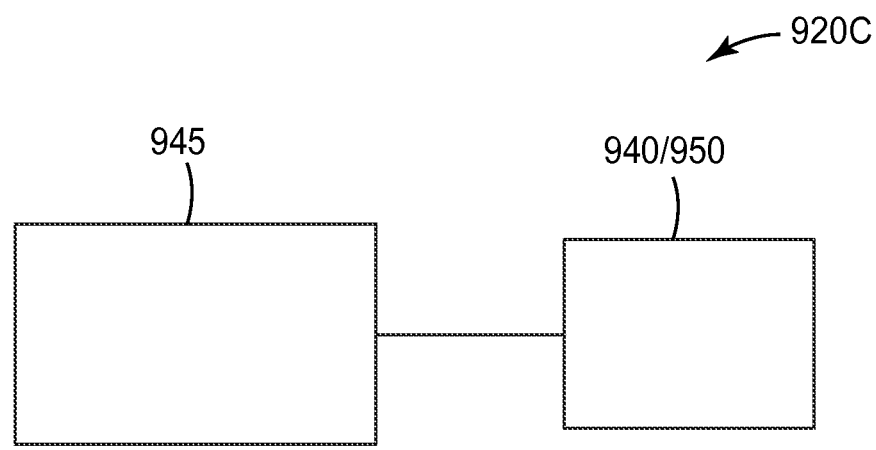
FIG. 9D illustrates an schematic diagram of one embodiment of a wireless sensing device for measuring a liquid level.

In some embodiments, as illustrated in FIGS. 9C and 9D, a wireless sensing device 920C can be designed to measure a liquid level. The wireless sensing device 920C includes an absorption element 945 that can absorb liquid, such as sweat, wound exudate, condensate, perspiration, oil, or the like. In the embodiment as illustrated in FIG. 9C, the absorption element 945 is in thermal contact with the thermal source 940 that is thermally coupled to the sensor 950. FIG. 9D illustrates another example of the wireless sensing device 920C includes the absorption element 945 that is in thermal contact with the thermal source 940 and thermal sensor 950, which can be an integrated component, for example. In some cases, the absorption element 945 and the thermal source 940/thermal sensor 950 are disposed proximate to each other and form thermal contact. In some other cases, the absorption element 945 and the thermal source 940/thermal sensor 950 are in physical contact. In some cases, the thermal source 940/thermal sensor 950 is disposed on or at least partially in the absorption element 945. Absorption element may include absorption material(s), for example, such as porous material, a natural or synthetic sponge, water-absorbing gel, superabsorbent polymer, a form, a gauze, a non-woven patch, or the like. Sponges may be made from cellulose, polyester or other polymers. Superabsorbent polymers may include polyacrylate/polyacrylamide copolymers, polyvinyl alcohol copolymers, for example. The wireless sensing device 920C can include other components, for example, the components in the wireless sensing device 920 illustrated in FIG. 9A.

In one embodiment, the wireless sensing device 920C is an RF sensor, which includes a substrate, an antenna disposed on the substrate, an RF circuit electrically coupled to the antenna, the RF circuit comprising a processor; an absorption element (e.g., 945) comprising absorption material, a thermal source (e.g., 940) electrically coupled to the RF circuit and thermally coupled to the absorption element;

and a sensing element (e.g., 950) thermally coupled to the thermal source for sensing a temperature of the thermal source, such that after the absorption element is used to absorb liquid, the RF sensor wirelessly receives a first power having a first form from a transceiver, the RF circuit transforms the first power to a second power having a second form different from the first form and delivers the second power to the thermal source, the sensing element senses a time variation of the thermal source temperature, and the processor determines an indicator indicating liquid level based on the sensed time variation of the thermal source temperature. A wireless sensing device or system can use a similar flowchart as illustrated in FIG. 7C to gather sensor data and determine an indicator indicating a liquid level.

EXAMPLES

Example 1

Wireless Sensing Device—Assembly and Temperature Rise Rates

Figure 10:
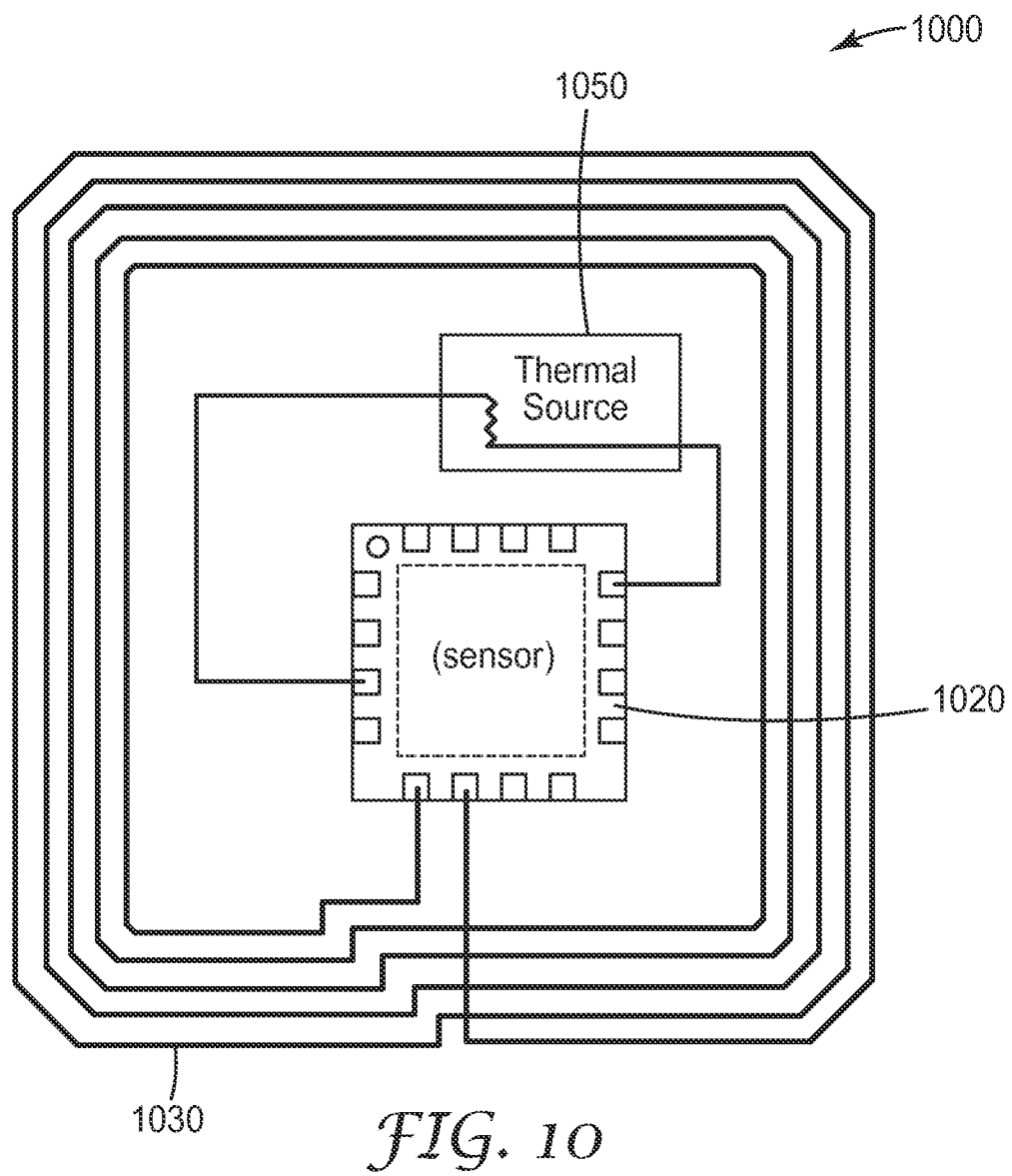
FIG. 10 illustrates a simplified schematic of one example of a wireless sensing device.

As illustrated in FIG. 10, a wireless sensing device 1000 was assembled in the following manner. A 5.0 mm×5.0 mm×0.9 mm AMS SL13A packaged RFID integrated circuit with temperature sensor 1020 obtained from Digikey of Thief River Falls, Minn. was electrically connected to a loop antenna 1030 composed of solid enamel coated 26 AWG copper wire obtained from Digikey of Thief River Falls, Minn. The loop antenna 1030 was created with four circular turns of the solid enamel coated 26 AWG copper wire at a diameter of 90 mm. The AMS SL13A packaged RFID integrated circuit with temperature sensor 1020 was also electrically connected to a 1.0 mm×0.5 mm×0.4 mm 0402-size resistor 1050 of value 850 Ω obtained from Digikey of Thief River Falls, Minn. The loop antenna 1030 was connected to pins 5 and 6 ("ANT1" and "ANT2") and the resistor was connected across terminals 3 ("VEXT") and 12 ("VSS") of the AMS SL13A packaged RFID integrated circuit with temperature sensor 1020.

The value of the surface mount resistor was chosen to limit the thermal source current (I) to a maximum specified value of 4 mA when the voltage (V) reaches a maximum of 3.4 V. This occurred when the wireless sensing device 1000 was located in the maximum magnetic field emitted by a reader and provided 13.6 mW (e.g., P=VI) of thermal source power in the resistor. Typically, a 0402-size resistor component dissipating 13.6 mW in a vacuum or with minimal heat transfer to the surrounding environment would experience an initial temperature rise rate of approximately 22.6° C. per second. Alternatively, if it were in similar environmental conditions and thermally connected to the AMS SL13A packaged RFID integrated circuit with temperature sensor 1020, the initial temperature rise rate would be reduced to about 0.4° C. per second due to the much larger volume of the SL13A package. The temperature rise rates were calculated based on the heat capacity of aluminum oxide and silicon, respectively, by using Equation (6):

$$\frac{\Delta T}{\Delta t} = \frac{P}{(c_p \times \rho \times V)} \quad (6)$$

where $\Delta T$ is temperature in ° C., $\Delta t$ is time in seconds, P is power in joules per second, $c_p$ is specific heat capacity in joules per gram-° C., $\rho$ is mass density in grams per cubic millimeter, and V is the volume in cubic millimeters. Calculation parameters and results are contained in Table 2.

TABLE 2

| Parameter | 0402 Resistor | SL13A Package |
|---|---|---|
| Power (J/s) | 1.36E−2 | 1.36E−2 |
| Specific Heat Capacity (J/g-° C.) | 8.8E−1 | 7.0E−1 |
| Density (g/cm$^3$) | 3.90 | 2.33 |
| Thickness (mm) | 3.5E−1 | 9.0E−1 |
| Area (mm$^2$) | 5.0E−1 | 2.5E1 |
| Volume (mm$^3$) | 1.75E−1 | 2.25E1 |
| Volume (cm$^3$) | 1.75E−4 | 2.25E−2 |
| ΔT/Δt (° C./s) | 2.26E1 | 3.71E−1 |

An intended use of the wireless sensing device 1000 would be to measure the effective local thermal conductance when in contact with a material of interest (e.g., human skin). The induced steady-state temperature rise in such a case would be the product of the input power P in watts and thermal resistance $R_{th}$ in ° C. per watt as represented in Equation (7):

$$\Delta T = P \times R_{th} \quad (7)$$

With 13.6 mW of heating, and given a minimum relative temperature measurement resolution (Minimum ΔT Resolution) of 0.3° C., the device could measure a thermal resistance (Minimum Measureable $R_{th}$) as low as 22° C. per watt and as high a thermal resistance as the wireless sensing device 1000 maximum temperature limit allow; for the AMS SL13A which has a temperature measurement limit of 60° C. in its standard mode, that maximum measureable thermal resistance for 13.6 mW of heating is about 3000° C. per watt corresponding to a 40° C. steady-state excursion above an ambient temperature of 20° C. A smaller temperature resolution or larger input power would reduce the minimum measureable thermal resistance as indicated in Table 3 and Table 4. The transient plane source method described previously herein is an example where the value of thermal resistance $R_{th}$ is the inverse value of effective thermal conductivity of the material scaled by lateral dimension of the heater element and constant factors.

TABLE 3

| Power Input (W) | Minimum ΔT Resolution (° C.) | Minimum Measurable $R_{th}$ (° C./W) |
|---|---|---|
| 1.36E−2 | 3.0E−1 | 2.2E1 |
| 1.36E−2 | 1.0E−1 | 7.4 |
| 1.36E−2 | 5.0E−2 | 3.7 |
| 1.36E−2 | 2.0E−2 | 1.5 |
| 1.36E−2 | 1.0E−2 | 7.4E−1 |
| 1.36E−2 | 5.0E−3 | 3.7E−1 |
| 1.36E−2 | 2.0E−3 | 1.5E−1 |
| 1.36E−2 | 1.0E−3 | 7.0E−2 |

TABLE 4

| Power Input (W) | Minimum ΔT Resolution (° C.) | Minimum Measurable $R_{th}$ (° C./W) |
|---|---|---|
| 1.0 | 1.0E−1 | 1.0E−1 |
| 2.0 | 1.0E−1 | 5.0E−2 |
| 5.0 | 1.0E−1 | 2.0E−2 |
| 1.0E1 | 1.0E−1 | 1.0E−1 |
| 2.0E1 | 1.0E−1 | 5.0E−3 |

TABLE 4-continued

| Power Input (W) | Minimum ΔT Resolution (° C.) | Minimum Measurable $R_{th}$ (° C./W) |
|---|---|---|
| 5.0E1 | 1.0E−1 | 2.0E−3 |
| 1.0E2 | 1.0E−1 | 1.0E−1 |

Example 2

Wireless Sensing Device—Differential

Figure 11:
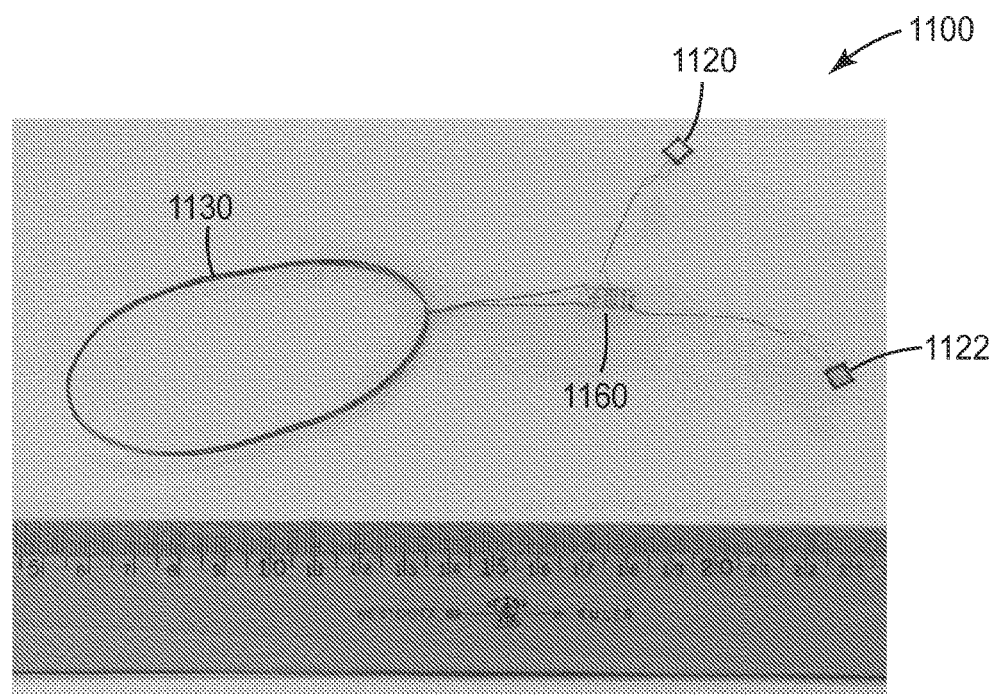
FIG. 11 is a picture of an example of a wireless sensing device with two integrated circuits.

A wireless sensing device with a first and second integrated circuit, each having a unique identification number was electrically connected to a single antenna as represented in FIG. 11. A wireless sensing device 1100 was assembled in the following manner. Two 5.0 mm×5.0 mm×0.9 mm AMS SL13A packaged RFID integrated circuits with temperature sensors 1120, 1122 obtained from Digikey of Thief River Falls, Minn. were electrically connected to a loop antenna 1130 composed of solid enamel coated 26 AWG copper wire obtained from Digikey of Thief River Falls, Minn. through an FR4 interface board 1160 with copper pads and traces configured to allow parallel connection of the antenna 1130 and integrated circuits 1120, 1122. Both of the AMS SL13A packaged RFID integrated circuits with temperature sensors 1120, 1122 were connected to the interface board 1160 with short lengths of solid enamel coated 34 AWG copper wire obtained from Digikey of Thief River Falls, Minn. The loop antenna 1130 was created with four circular turns of the solid enamel coated 26 AWG copper wire at a diameter of 60 mm. The loop antenna 1130 was designed to resonate with 50 pF with an intended inductance of 2.75 μH at 13.56 MHz. Actual loop antenna inductance of the 60 mm diameter circular coil was higher than intended and produced a resonance of about 13.17 MHz, so its inductance was reduced to achieve tag resonance near 13.56 MHz by compressing the circular antenna into an ellipse as illustrated in FIG. 11. The loop antenna 1130 was connected to pins 5 and 6 ("ANT1" and "ANT2") of the AMS SL13A packaged RFID integrated circuits with temperature sensors 1120, 1122 through the interface board 1160. The thermal sources in this example are Joule heating within each integrated circuit 1120, 1122 induced by interaction of each integrated circuit with a reader magnetic field via the antenna.

The wireless sensing device 1100 was tested by a 3M radio frequency identification (RFID) reader Model 810 and reader antenna Model 870 obtained from 3M Company of St. Paul, Minn. connected via a universal serial bus (USB) cable to a laptop personal computer (PC) running test software. The test consisted of operating the reader via the PC to query for the presence of unique security identifiers (SIDs) using the ISO 15693 RFID communication protocol. The software reported the number and quantity of unique SIDs read. The maximum read range was found to be 18 cm for this configuration.

Figure 12:
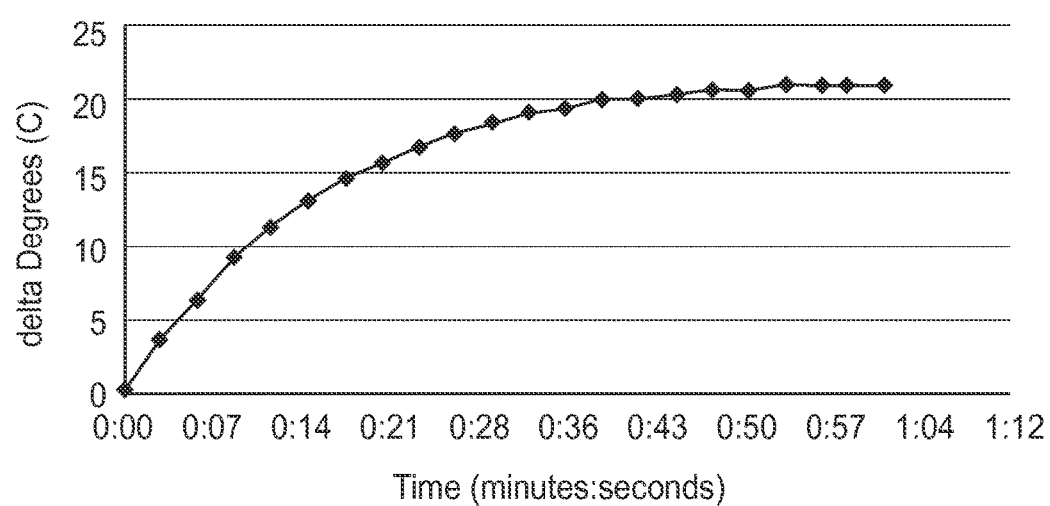
FIG. 12 illustrates an example graph of temperature verse time.

The wireless sensing device 1100 was also tested with a RFID reader AMS AS3911 General Purpose Demo Kit Rev 1.0 and its accompanying PC software obtained as part number AS3911-DK-ST-ND from Digikey of Thief River Falls, Minn., to produce the example temperature versus time data in FIG. 12. The thermal source within each integrated circuit was controlled by modulation of the reader magnetic field by placing the sensing device 1100 in proximity to the reader with the reader magnetic field disabled and the integrated circuits 1120, 1122 primarily suspended in air, and then enabling the reader magnetic field at zero time in FIG. 12 and querying a first temperature from each integrated circuit 1120, 1122. The reader magnetic field remained enabled while data were periodically obtained by addressing one of the integrated circuits with the reader, with the first temperature subtracted to produce the relative temperature shown in FIG. 12. Data gathered as reported by alternately addressing the other integrated circuit were similar.

Example 3

Wireless Sensing Device—Hydration Monitoring
(Single Turn Loop)

As illustrated in FIG. 10, a wireless sensing device 1000 was assembled in the following manner. A 5.0 mm×5.0 mm×0.9 mm AMS SL13A-AQFT packaged RFID integrated circuit with temperature sensor 1020 obtained from Digikey of Thief River Falls, Minn. was electrically connected with 34 AWG copper inductor wire to a 78 mm×84 mm×0.08 mm loop antenna 1030. The loop antenna 1030 was created with a single loop of 3M™ copper tape obtained from 3M™ Company of Saint Paul, Minn. Parallel capacitance totaling 606 pF of 0603 size NPO type ceramic tuning capacitors obtained from Digikey of Thief River Falls, Minn. was connected to the loop antenna. The wireless sensing device 1000 was affixed to a 100 mm×100 mm×3.3 mm layer of foam from a 90612 Tegaderm™ foam adhesive dressing obtained from 3M™ Company of Saint Paul, Minn.

Dry and wet measurements were obtained using an LG Nexus 5 smartphone with custom Android application that provided wireless power, analyzed temperature data points, and calculated time-temperature thresholds as well as indicated status of the Tegaderm™ Foam Adhesive dressing layer. Analysis was performed with the LG Nexus 5 smartphone in a lateral position relative to the foam adhesive dressing at a fixed vertical separation of 15 mm.

Measurements were performed dry and after dispensing controlled amounts of deionized water distributed across the bottom surface of the foam. Each measurement was repeated three times for each condition separated by three minutes to allow the NFC integrated circuit to return to near ambient temperature. Results are contained in Table 5.

TABLE 5

| | Relative Temperature (ΔT) | | | | | | | |
|---|---|---|---|---|---|---|---|---|
| Time | Dry | | | 10 mL Water | | | 20 mL Water | | |
| (s) | Avg. | Max. | Min. | Avg. | Max. | Min. | Avg. | Max. | Min. |
| 0 | 0.0 | 0.0 | 0.0 | 0.0 | 0.0 | 0.0 | 0.0 | 0.0 | 0.0 |
| 2 | 0.6 | 0.7 | 0.3 | 0.6 | 0.7 | 0.3 | 0.3 | 0.3 | 0.3 |
| 4 | 1.6 | 1.7 | 1.3 | 1.0 | 1.3 | 0.7 | 0.6 | 0.7 | 0.3 |
| 6 | 2.0 | 2.4 | 1.7 | 1.3 | 1.3 | 1.3 | 0.8 | 1.0 | 0.7 |
| 8 | 2.7 | 2.7 | 2.7 | 1.8 | 2.1 | 1.7 | 0.9 | 1.0 | 0.7 |
| 10 | 3.2 | 3.4 | 3.1 | 2.0 | 2.4 | 1.7 | 1.1 | 1.3 | 1.0 |
| 20 | 5.2 | 5.4 | 5.1 | 3.1 | 3.4 | 2.7 | 1.3 | 1.3 | 1.3 |

The configuration was designed to be insensitive to changes in local permittivity such as proximity to water. Measured antenna resonance conditions did not change significantly during the test, indicating the mechanism observed is based on changes in heat transfer rather than changes in input electrical power. Measured resonance for each condition is in summarized in Table 6.

TABLE 6

|  | Resonant frequency (MHz) | Quality factor |
|---|---|---|
| Dry | 13.01 | 46 |
| 10 mL water | 13.00 | 46 |
| 20 mL water | 12.92 | 45 |

Example 4

Wireless Sensing Device—Hydration Monitoring
(Four Turn Loop)

As illustrated in FIG. 10, a wireless sensing device 1000 was assembled in the following manner. A 5.0 mm×5.0 mm×0.9 mm AMS SL13A-AQFT packaged RFID integrated circuit with temperature sensor 1020 obtained from Digikey of Thief River Falls, Minn. was electrically connected to a loop antenna 1030 composed of solid enamel coated 34 AWG copper wire obtained from Digikey of Thief River Falls, Minn. The loop antenna 1030 was created with four circular turns of the solid enamel coated 34 AWG copper wire at a diameter of 50 mm. A 24 pF 0603 size NPO type ceramic tuning capacitor obtained from Digikey of Thief River Falls, Minn. was connected to the loop antenna 1030. The wireless sensing device 1000 was affixed to a 100 mm×100 mm×3.3 mm layer of foam from a 90612 Tegaderm™ Foam Adhesive dressing obtained from 3M™ Company of Saint Paul, Minn.

Dry and wet measurements were obtained using an LG Nexus 5 smartphone with custom Android application that provided wireless power, analyzed temperature data points, and calculated time-temperature thresholds as well as indicated status of the Tegaderm™ foam adhesive dressing. Analysis was performed with the LG Nexus 5 smartphone in a lateral position relative to the foam adhesive dressing at a fixed vertical separation of 15 mm.

Measurements were performed dry and after dispensing controlled amounts of deionized water distributed across the bottom surface of the foam. Each measurement was repeated three times for each condition separated by three minutes to allow the NFC integrated circuit to return to near ambient temperature. Results are contained in Table 7.

TABLE 7

| | Relative Temperature (ΔT) | | | | | | | | |
|---|---|---|---|---|---|---|---|---|---|
| Time | Dry | | | 10 mL Water | | | 20 mL Water | | |
| (s) | Avg. | Max. | Min. | Avg. | Max. | Min. | Avg. | Max. | Min. |
| 0 | 0.0 | 0.0 | 0.0 | 0.0 | 0.0 | 0.0 | 0.0 | 0.0 | 0.0 |
| 2 | 0.4 | 0.7 | 0.3 | 1.0 | 1.0 | 1.0 | 0.2 | 0.3 | 0.0 |
| 4 | 1.3 | 1.7 | 1.0 | 1.1 | 1.3 | 1.0 | 0.4 | 0.7 | 0.3 |
| 6 | 2.2 | 2.4 | 2.1 | 1.7 | 1.7 | 1.7 | 0.4 | 0.7 | 0.3 |
| 8 | 2.7 | 3.1 | 2.4 | 2.0 | 2.4 | 1.7 | 0.4 | 1.0 | 0.0 |
| 10 | 3.2 | 3.4 | 3.1 | 2.4 | 2.7 | 2.1 | 0.4 | 0.7 | 0.3 |
| 20 | 5.6 | 5.7 | 5.4 | 3.4 | 3.7 | 3.1 | 0.8 | 1.0 | 0.7 |

Heat transfer effects are confounded by the shifts in resonance that cause less electrical power to be transferred as water infiltrates the foam. Measured resonance are summarized in Table 8.

TABLE 8

|  | Resonant frequency (MHz) | Quality factor |
|---|---|---|
| Dry | 14.42 | 73 |
| 10 mL | 13.57 | 27 |
| 20 mL | 12.46 | 15 |

Example 5

Wireless Sensing Device—Sweat Monitoring

A wireless sensing device 620C, as represented in FIG. 6C, was assembled in the following manner. A STM20-DD9F ultra-low current precision analog temperature sensor 650C obtained from STMicroelectronics of Geneva, Switzerland was thermally connected to a 500 Ω resistive thermal source 640C comprised of two 0402 sized 1000Ω resistors in parallel obtained from Digikey of Thief River Falls, Minn. The temperature sensor 650C and resistive thermal source 640C were positioned on opposite surfaces of an internally fabricated flexible circuit constructed with three 12 μm layers: copper/polyimide/copper. A sensor tip for measurement was affixed with 9836 acrylate adhesive film obtained from 3M™ Company of Saint Paul, Minn. to the bottom layer of foam at the central surface of an assembly of two layers of 25 mm×25 mm MSX-6916B open-cell polyurethane foam obtained from 3M™ Company of Saint Paul, Minn. which has nominal thickness 2.4 mm. The internal surface of the top layer of the two layers of foam was coated with 9836 acrylate adhesive film obtained from 3M™ Company of Saint Paul, Minn. to protect from moisture infiltration. A loop antenna 635C was created with two circular turns of copper traces with thickness 17 μm, trace width 3.4 mm, and outer diameter of 50 mm on opposing surfaces of a printed circuit board. A parallel capacitance of 350 pF comprised of 0603 size NPO type ceramic tuning capacitors obtained from Digikey of Thief River Falls, Minn. was connected to the loop antenna 635C to produce a resonant frequency of 13.66 MHz and quality factor of 50.

A dynamic NFC M24LR16E-RMC6T/2 transponder 632C with serial communication interface and non-volatile memory integrated circuit was electrically connected to the loop antenna and to a STM32L052C8T6 microcontroller, both obtained from STMicroelectronics of Geneva, Switzerland, were used for power and analysis purposes. The temperature sensor and resistive thermal source were each electrically connected to the microcontroller. An NFC CR95HF reader 618C demonstration board obtained from STMicroelectronics, with corresponding M24LRxx Application Software also obtained from STMicroelectronics, was positioned 25 mm above the printed circuit board to gather measurements.

Table 9 represents the experimental conditions for deionized water progressively added to the bottom layer of foam. In each case, to emulate the uniform distribution of fluid, a controlled volume of deionized water was dispensed onto an aluminum plate. The bottom layer of foam was placed onto the water drop and then compressed and released multiple times to distribute the fluid throughout the bottom foam layer. Then, the bottom layer of foam was weighed, reassembled with the top piece of foam for thermal isolation from the ambient, and a wirelessly powered measurement was performed with the NFC reader 618C and the wireless sensing device 620C. A measurement was triggered by the NFC reader 618C via an activation signal 615C in the form of wirelessly writing to a memory location within the wireless transceiver 632C. Temperature and voltage applied to the thermal source resistance were recorded at regular intervals in the wireless sensing device, and uploaded to the NFC reader as data signal 613C. Dataset ID "A6" was measured after the foam was allowed to dry in ambient conditions for one week. The column of Table 9 for "Equivalent minutes at 0.7 mg/cm$^2$/min" is the amount of time in minutes that each respective amount of water would take to accumulate at a uniform flow rate of 0.7 mg of water per square centimeter per minute into a 25×25 mm surface of the bottom foam. The column of Table 9 for "Water % of Foam 1.5 cm$^3$ Volume" is the percentage of the bottom foam layer's volume assuming a water mass density of 1 gram per cubic centimeter.

TABLE 9

| Dataset ID | Measured Bottom Layer Foam Mass (g) | Water Mass (g) | Water Mass per Surface Area (mg/cm$^2$) | Equivalent minutes at 0.7 mg/cm$^2$/min | Water % of Foam 1.5 cm$^3$ Volume |
|---|---|---|---|---|---|
| A1 | 0.21 | — | — | — | — |
| A2 | 0.31 | 0.10 | 15 | 22 | 6% |
| A3 | 0.39 | 0.18 | 29 | 41 | 12% |
| A4 | 0.55 | 0.34 | 54 | 78 | 23% |
| A5 | 0.82 | 0.61 | 98 | 139 | 41% |
| A6 | 0.22 | 0.01 | 2 | 2 | 1% |

Results are shown in Table 10 and are presented as the relative temperature per unit of average thermal power represents the reduction in the temperature rise with increasing fluid concentration due to the increase in thermal conductivity and diffusivity. Relative temperature $\Delta T$ is defined as the change from the initial temperature value: $T-T_I$, where $T_I$ was the initial temperature. Recorded thermal power in these datasets was between 8.2 and 8.8 milliwatts and an average was calculated for each dataset. The values in Table 10 were averaged from the raw data collected at 50 millisecond intervals; averaging windows of one-second width were used, centered on each whole second.

TABLE 10

ΔT per average power (° C./mW)

| t (s) | A1 | A2 | A3 | A4 | A5 | A6 |
|---|---|---|---|---|---|---|
| 0.00 | 0.00 | 0.00 | 0.00 | 0.00 | 0.00 | 0.00 |
| 1.00 | 0.22 | 0.15 | 0.15 | 0.12 | 0.13 | 0.21 |
| 2.00 | 0.38 | 0.27 | 0.25 | 0.21 | 0.19 | 0.37 |
| 3.00 | 0.48 | 0.30 | 0.31 | 0.28 | 0.24 | 0.48 |
| 4.00 | 0.57 | 0.36 | 0.34 | 0.31 | 0.25 | 0.57 |
| 5.00 | 0.67 | 0.41 | 0.35 | 0.33 | 0.29 | 0.69 |
| 6.00 | 0.72 | 0.41 | 0.37 | 0.34 | 0.29 | 0.73 |
| 7.00 | 0.77 | 0.45 | 0.38 | 0.37 | 0.33 | 0.81 |
| 8.00 | 0.80 | 0.49 | 0.41 | 0.36 | 0.33 | 0.85 |
| 9.00 | 0.87 | 0.48 | 0.43 | 0.38 | 0.34 | 0.92 |
| 10.00 | 0.88 | 0.49 | 0.44 | 0.42 | 0.35 | 0.93 |
| 11.00 | 0.91 | 0.48 | 0.46 | 0.40 | 0.35 | 0.96 |
| 12.00 | 0.95 | 0.51 | 0.46 | 0.42 | 0.37 | 1.00 |
| 13.00 | 0.97 | 0.52 | 0.49 | 0.44 | 0.37 | 1.06 |
| 14.00 | 0.98 | 0.52 | 0.48 | 0.46 | 0.37 | 1.03 |
| 15.00 | 0.99 | 0.52 | 0.48 | 0.45 | 0.37 | 1.05 |
| 16.00 | 1.00 | 0.53 | 0.49 | 0.44 | 0.37 | 1.09 |
| 17.00 | 1.03 | 0.55 | 0.51 | 0.44 | 0.35 | 1.12 |
| 18.00 | 1.06 | 0.53 | 0.50 | 0.44 | 0.40 | 1.11 |
| 19.00 | 1.05 | 0.56 | 0.50 | 0.47 | 0.39 | 1.12 |
| 20.00 | 1.07 | 0.58 | 0.52 | 0.48 | 0.40 | 1.14 |
| 21.00 | 1.09 | 0.57 | 0.52 | 0.47 | 0.40 | 1.13 |
| 22.00 | 1.08 | 0.61 | 0.51 | 0.46 | 0.40 | 1.14 |
| 23.00 | 1.09 | 0.57 | 0.52 | 0.47 | 0.41 | 1.15 |
| 24.00 | 1.12 | 0.58 | 0.52 | 0.47 | 0.41 | 1.17 |
| 25.00 | 1.11 | 0.56 | 0.53 | 0.49 | 0.41 | 1.13 |

Table 11 represents a replicate trial of the experimental conditions in Table 9 and results in Table 10, except that instead of control Dataset ID "A6" where the foam was allowed to dry for one week at the conclusion of the experiment, in Table 11 there was control Dataset ID "A8" which was a repeat of the dry state after exposure of the foam to the process emulating the addition of water but without a water drop present on the aluminum plate. Recorded thermal power in the Table 11 datasets was between 7.8 and 8.2 milliwatts. Results are contained in Table 12, with processing as described for Table 10.

TABLE 11

| Dataset ID | Measured Bottom Layer Foam Mass (g) | Water Mass (g) | Water Mass per Surface Area (mg/cm$^2$) | Equivalent minutes at 0.7 mg/cm$^2$/min | Water % of Foam 1.5 cm$^3$ Volume |
|---|---|---|---|---|---|
| A7 | 0.20 | — | — | — | — |
| A8 | 0.20 | 0.00 | 0 | 0 | 0% |
| A9 | 0.27 | 0.07 | 11 | 16 | 5% |
| A10 | 0.35 | 0.15 | 24 | 34 | 10% |
| A11 | 0.51 | 0.31 | 50 | 71 | 21% |
| A12 | 0.81 | 0.61 | 97 | 138 | 40% |

TABLE 12

ΔT per average power (° C./mW)

| t (s) | A7 | A8 | A9 | A10 | A11 | A12 |
|---|---|---|---|---|---|---|
| 0.00 | 0.00 | 0.00 | 0.00 | 0.00 | 0.00 | 0.00 |
| 1.00 | 0.21 | 0.19 | 0.18 | 0.13 | 0.14 | 0.14 |
| 2.00 | 0.38 | 0.34 | 0.27 | 0.23 | 0.19 | 0.20 |
| 3.00 | 0.48 | 0.49 | 0.31 | 0.28 | 0.22 | 0.25 |
| 4.00 | 0.58 | 0.56 | 0.35 | 0.34 | 0.29 | 0.27 |
| 5.00 | 0.67 | 0.64 | 0.41 | 0.36 | 0.34 | 0.30 |
| 6.00 | 0.73 | 0.70 | 0.44 | 0.38 | 0.35 | 0.32 |
| 7.00 | 0.78 | 0.76 | 0.44 | 0.42 | 0.33 | 0.33 |
| 8.00 | 0.83 | 0.78 | 0.48 | 0.40 | 0.37 | 0.36 |
| 9.00 | 0.89 | 0.82 | 0.49 | 0.44 | 0.39 | 0.34 |
| 10.00 | 0.90 | 0.88 | 0.50 | 0.46 | 0.39 | 0.37 |
| 11.00 | 0.96 | 0.90 | 0.54 | 0.47 | 0.40 | 0.37 |
| 12.00 | 0.96 | 0.93 | 0.54 | 0.48 | 0.41 | 0.40 |
| 13.00 | 0.99 | 0.98 | 0.53 | 0.48 | 0.45 | 0.43 |
| 14.00 | 1.00 | 0.93 | 0.56 | 0.50 | 0.46 | 0.40 |
| 15.00 | 1.00 | 0.97 | 0.57 | 0.47 | 0.43 | 0.42 |
| 16.00 | 1.04 | 1.00 | 0.59 | 0.50 | 0.44 | 0.42 |
| 17.00 | 1.06 | 1.04 | 0.57 | 0.49 | 0.44 | 0.42 |
| 18.00 | 1.06 | 1.01 | 0.56 | 0.52 | 0.47 | 0.45 |
| 19.00 | 1.11 | 1.07 | 0.62 | 0.52 | 0.50 | 0.44 |
| 20.00 | 1.09 | 1.06 | 0.56 | 0.51 | 0.50 | 0.45 |
| 21.00 | 1.11 | 1.06 | 0.62 | 0.55 | 0.49 | 0.45 |
| 22.00 | 1.11 | 1.07 | 0.62 | 0.53 | 0.48 | 0.45 |
| 23.00 | 1.12 | 1.12 | 0.61 | 0.53 | 0.49 | 0.46 |
| 24.00 | 1.11 | 1.12 | 0.61 | 0.53 | 0.50 | 0.44 |
| 25.00 | 1.15 | 1.08 | 0.62 | 0.56 | 0.50 | 0.44 |

EXEMPLARY EMBODIMENTS

Embodiment A1. A wireless sensing device in an assembly for measuring thermal property of an object, comprising: a thermal spreader comprising solid or liquid material, the thermal spreader having a first major surface and a second major surface opposite to the first major surface, the thermal spreader configured to be in thermal contact with the object when the wireless sensing device is in use; a control circuit; a wireless transceiver electronically coupled to the control circuit; an energy harvesting device; a thermal source disposed proximate to the second major surface of the thermal spreader, the thermal source electronically coupled to the energy harvesting device and configured to generate a thermal flux to the first major surface of the thermal spreader, wherein the energy harvesting device provides power to the thermal source; and a sensor electronically coupled to the control circuit and in thermal contact with the thermal source, wherein the sensor is configured to generate a sensor signal associated with temperature and provide the sensor signal to the control circuit.

Embodiment A2. The wireless sensing device of Embodiment A1, further comprising: an antenna electronically coupled to the transceiver and the energy harvesting device.

Embodiment A3. The wireless sensing device of Embodiment A2, further comprising: a substrate, wherein the antenna is disposed on the substrate.

Embodiment A4. The wireless sensing device of Embodiment A3, wherein the antenna is configured to receive a first power when a reader interrogates the wireless sensing device and the energy harvesting device is configured to convert the first power to a second power.

Embodiment A5. The wireless sensing device of Embodiment A1-A4, further comprising:

a coupling device configured to maintain thermal contact between the thermal spreader and the object.

Embodiment A6. The wireless sensing device of Embodiment A5, wherein the coupling device comprises at least one of a thermally conductive adhesive layer, elastic coupler, and mechanical coupler.

Embodiment A7. The wireless sensing device of Embodiment A1-A6, wherein the thermal source comprises at least one component of the control circuit.

Embodiment A8. The wireless sensing device of Embodiment A1, wherein the thermal source and the sensor are a same resistive element.

Embodiment A9. The wireless sensing device of any one of Embodiment A1-A8, wherein the control circuit comprises a microprocessor and a memory storing a unique identifier.

Embodiment A10. The wireless sensing device of Embodiment A1-A9, wherein the energy harvesting device comprise at least one of a bridge rectifier, a diode rectifier, a transistor rectifier, a voltage regulator and a current regulator.

Embodiment A11. The wireless sensing device of Embodiment A1-A10, wherein the wireless sensing device regulates power provided the thermal source.

Embodiment A12. The wireless sensing device of Embodiment A11, wherein the wireless sensing device regulates the thermal source based on the sensor signal.

Embodiment A13. The wireless sensing device of Embodiment A12, wherein the wireless sensing device deactivates the thermal source based on the sensor signal.

Embodiment A14. The wireless sensing device of Embodiment A1-A13, wherein the sensor is configured to generate a first sensor signal before the thermal source is activated and a second sensor signal after the thermal source is activated.

Embodiment A15. The wireless sensing device of Embodiment A13, wherein the control circuit is configured to determine a thermal property of the object based on the first and second sensor signals.

Embodiment A16. The wireless sensing device of Embodiment A15, wherein the control circuit provides a generally constant power to the thermal source with a known power magnitude, wherein the control circuit determines a thermal property of the object based on the first sensor signal, the second sensor signal, and the know power magnitude.

Embodiment A17. The wireless sensing device of Embodiment A2, wherein the control circuit comprises an integrated capacitance, wherein the wireless sensing device receives power when a reader interrogates the wireless sensing device, and wherein the control circuit modifies the integrated capacitance based on the sensor signal and/or the received power.

Embodiment A18. A wireless sensing device in an assembly for measuring a thermal property of an object, comprising: an antenna and a transceiver configured to receive a first power wirelessly; an energy harvesting device configured to transform the first power to a second power; a thermal source electronically couple to the energy harvesting device, wherein the energy harvesting device provides the second power to the thermal source; a control circuit comprising a microprocessor; and a sensor electronically coupled to the control circuit and thermally coupled to the thermal source, wherein the sensor is configured to generate a first sensor signal before the thermal source is activated and a second sensor signal after the thermal source is activated, and wherein the control circuit is configured to determine a thermal property of the object based on the first and second sensor signals.

Embodiment A19. The wireless sensing device of Embodiment A18, further comprising: a substrate, and a thermal spreader comprising solid or liquid material, the thermal spreader configured to be in thermal contact with the object, wherein the thermal source and the sensor are disposed in the thermal spreader.

Embodiment A20. The wireless sensing device of Embodiment A18-A19, wherein the control circuit regulates an output of the thermal source.

Embodiment A21. The wireless sensing device of Embodiment A20, wherein the control circuit regulates the thermal source based on the second sensor signal generated by the sensor.

Embodiment A22. The wireless sensing device of Embodiment A18-A21, wherein the thermal source and the sensor are a same resistive element.

Embodiment A23. The wireless sensing device of Embodiment A18-A22, wherein the control circuit comprises a microprocessor and a memory storing a unique identifier.

Embodiment A24. The wireless sensing device of Embodiment A18-A23, wherein the energy harvesting device comprises a bridge rectifier, a diode rectifier, a transistor rectifier, a voltage regulator and a current regulator.

Embodiment B1. A wireless sensing device configured to measure a physical property of an object, comprising: a substrate; an antenna disposed on the substrate; a first control circuit electronically coupled to the antenna, the first control circuit comprising a first memory storing a first unique identifier and a first transceiver; a second control circuit electronically coupled to the antenna, the second control circuit comprising a second memory storing a second unique identifier and a second transceiver; a first excitation device configured to generate a first excitation signal to change a physical property of the object; a first sensor electronically coupled to the first control circuit, wherein the first sensor is configured to generate a first sensor signal associated with the physical property; and a second sensor electronically coupled to the second control circuit, wherein the second sensor is configured to generate a second sensor signal.

Embodiment B2. The wireless sensing device of Embodiment B1, wherein the first excitation device comprises at least one of thermal excitation device, light excitation device, sound excitation device, vibrator, voltage source, current source, and electromagnet.

Embodiment B3. The wireless sensing device of Embodiment B2, wherein the first sensor or the second sensor comprises at least one of thermal sensor, photodiode, microphone, accelerometer, voltage sensor, current sensor, and magnetometer.

Embodiment B4. The wireless sensing device of Embodiment B1-B3, further comprising: a first sensing region, wherein the first excitation device and the first sensor are disposed in the first sensing region.

Embodiment B5. The wireless sensing device of Embodiment B4, further comprising: a second sensing region, wherein the second sensor are disposed in the second sensing region.

Embodiment B6. The wireless sensing device of Embodiment B5, wherein the first sensor and the second sensor are thermal sensors, and wherein the first sensing region and the second region are thermally isolated.

Embodiment B7. The wireless sensing device of Embodiment B1-B6, further comprising:

a second excitation device configured to generate a second excitation signal.

Embodiment B8. The wireless sensing device of Embodiment B1-B7, wherein the antenna is configured to provide power to the wireless sensing device when a reader interrogates.

Embodiment B9. The wireless sensing device of Embodiment B1-B8, further comprising:

an energy harvesting device electronically coupled to the antenna and configured to provide power to the first sensor and the second sensor.

Embodiment B10. The wireless sensing device of Embodiment B9, wherein the energy harvesting device comprises at least one of a bridge rectifier, a diode rectifier, a transistor rectifier, a voltage regulator and a current regulator.

Embodiment B11. The wireless sensing device of Embodiment B1-B10, further comprising:

a processor electronically coupled to the first control circuit and the second control circuit, wherein the processor is configured to determine an indicator indicative of the physical property of the object based on the first sensor signal and the second sensor signal.

Embodiment B12. The wireless sensing device of Embodiment B1-B11, wherein the second sensor signal is associated with the physical property of the object.

Embodiment B13. The wireless sensing device of Embodiment B1-B12, wherein the first control circuit regulates the first excitation device.

Embodiment B14. The wireless sensing device of Embodiment B13, wherein the first control circuit regulates the first excitation device using the first sensor signal.

Embodiment B15. A wireless sensing device configured to measure a thermal property of an object, comprising: a first thermal spreader and a second thermal spreader being thermally insulated from the first thermal spreader; an RF circuit and an antenna electronically coupled to the RF circuit; an energy harvesting device; a first thermal source disposed in the first thermal spreader and electronically coupled to the energy harvesting device; a first sensor thermally coupled to the first thermal source, wherein the first sensor is configured to generate a first sensor signal associated with temperature; a second thermal source disposed in the second thermal spreader and electronically coupled to the energy harvesting device, and a second sensor thermally coupled to the second thermal source, wherein the second sensor is configured to generate a second sensor signal associated with temperature, wherein the energy harvesting device is configured to provide a first power to the first thermal source and a second power to the second thermal source, wherein the first power has a known ratio to the second power.

Embodiment B16. The wireless sensing device of Embodiment B15, wherein the second thermal source is in thermal contact with the object.

Embodiment B17. The wireless sensing device of Embodiment B15-B16, wherein the first thermal source and the first sensor are a same resistive element.

Embodiment B18. The wireless sensing device of Embodiment B15-B17, wherein the RF circuit comprises a microprocessor and a memory storing a unique identifier.

Embodiment B19. The wireless sensing device of Embodiment B15-B18, wherein the energy harvesting device comprises at least one of a bridge rectifier, a diode rectifier, a transistor rectifier, a voltage regulator and a current regulator.

Embodiment B20. The wireless sensing device of Embodiment B18, wherein the RF circuit is configured to determine a thermal property of the object based on the first and second sensor signals.

Embodiment B21. The wireless sensing device of Embodiment B15-B20, wherein the first power is equal to the second power.

Embodiment C1. An RF hydration sensor in an assembly, comprising:

a substrate;

an antenna disposed on the substrate;

an RF circuit electrically coupled to the antenna, the RF circuit comprising a processor;

a thermal source electrically coupled to the RF circuit for changing a thermal condition of a target area; and a sensing element thermally coupled to the thermal source for sensing a temperature of the thermal source, such that when the thermal source is thermally coupled to the target area, the RF hydration sensor wirelessly receives a first power having a first form from a transceiver, the RF circuit transforms the first power to a second power having a second form different from the first form and delivers the second power to the thermal source, the sensing element senses a time variation of the thermal source temperature, and the processor determines a hydration indicator indicating hydration level based on the sensed time variation of the thermal source temperature.

Embodiment C2. The RF hydration sensor of Embodiment C1, further comprising: a memory storing a reference data associated with hydration level, and wherein the processor is configured to determine the hydration indicator using the reference data.

Embodiment C3. The RF hydration sensor of Embodiment C1 or C2, wherein the RF circuit controls a magnitude of the second power.

Embodiment C4. The RF hydration sensor of any one of Embodiment C1 to Embodiment C3, wherein the RF circuit is configured to adjust duration of power supplied to the thermal source.

Embodiment C5. The RF hydration sensor of any one of Embodiment C1 to Embodiment C4, further comprising: a thermal spreader comprising a solid or liquid material, wherein the thermal source is disposed proximate to the thermal spreader.

Embodiment C6. The RF hydration sensor of Embodiment C5, wherein the thermal spreader is adapted to substantially uniformly distribute thermal flux from the thermal source across the target area when the thermal spreader is in thermal contact with the target area.

Embodiment C7. The RF hydration sensor of any one of Embodiment C1 to Embodiment C6, wherein the first form is an AC form and the second form is a DC form.

Embodiment C8. The RF hydration sensor of any one of Embodiment C1 to Embodiment C7, wherein the RF hydration sensor is configured to wirelessly receive an unknown first power having a first form from a transceiver, and wherein the RF circuit transforms the unknown first power to a known second power having a second form different from the first form.

Embodiment C9. The RF hydration sensor of any one of Embodiment C1 to Embodiment C8, wherein the RF circuit is configured to change the magnitude of the second power by changing a resonant frequency of the RF hydration sensor.

Embodiment C10. The RF hydration sensor of any one of Embodiment C1 to Embodiment C9, wherein the processor is configured to determine whether a thermal steady state is reached, and wherein the RF circuit deactivates the thermal source after the thermal steady state based on the sensed time variation of the thermal source temperature.

Embodiment C11. The RF hydration sensor of any one of Embodiment C1 to Embodiment C10, wherein the sensing element senses a cooling time variation of the thermal source temperature after the thermal source is deactivated, and wherein the processor determines a thermal diffusivity of the target area based on the sensed cooling time variation of the thermal source temperature, and wherein the processor determines the hydration indicator using the determined thermal diffusivity of the target area.

Embodiment C12. The RF hydration sensor of any one of Embodiment C1 to Embodiment C11, wherein the RF hydration sensor is adapted to wirelessly communicate with a remote transceiver emitting power at a first radio frequency, wherein the RF circuit is adapted to detune a resonant frequency of the RF hydration sensor away from the first radio frequency to control a magnitude of the first power received by the RF hydration sensor from the remote transceiver.

Embodiment C13. The RF hydration sensor of any one of Embodiment C1 to Embodiment C12, wherein the substrate is flexible.

Embodiment C14. The RF hydration sensor of any one of Embodiment C1 to Embodiment C13, wherein the substrate is stretchable.

Embodiment C15. An RF sensor for measuring a liquid level, comprising:
a substrate;
an antenna disposed on the substrate;
an RF circuit electrically coupled to the antenna, the RF circuit comprising a processor;
an absorption element comprising absorption material,
a thermal source electrically coupled to the RF circuit and thermally coupled to the absorption element; and
a sensing element thermally coupled to the thermal source for sensing a temperature of the thermal source, such that after the absorption element is used to absorb liquid, the RF sensor wirelessly receives a first power having a first form from a transceiver, the RF circuit transforms the first power to a second power having a second form different from the first form and delivers the second power to the thermal source, the sensing element senses a time variation of the thermal source temperature, and the processor determines an indicator indicating liquid level based on the sensed time variation of the thermal source temperature.

Embodiment C16. The RF sensor of Embodiment C15, wherein absorption material comprises at least one of a porous material, a natural or synthetic sponge, water-absorbing gel, and superabsorbent polymer.

Embodiment C17. The RF sensor of Embodiment C15 or 16, wherein the RF circuit controls a magnitude of the second power.

Embodiment C18. The RF sensor of any one of Embodiment C15 to Embodiment C17, wherein the RF circuit is configured to adjust duration of power supplied to the thermal source.

Embodiment C19. The RF sensor of any one of Embodiment C15 to Embodiment C18, wherein the first form is an AC form and the second form is a DC form.

Embodiment C20. A method of determining hydration level using one or more processors and a sensor having a thermal source disposed proximate to an object, comprising:
wirelessly activating the thermal source;
generating a series of sensing signals by the sensor;
determining, by the one or more processors, a thermal property of the object based on at least some of the series of sensing signals; and
generating, by the one or more processors, a hydration indicator indicative of hydration level of the object based on the determined thermal property and a reference data.

Embodiment C21. The method of Embodiment C20, further comprising:
generating a first sensing signal;
evaluating, by the one or more processors, whether a thermal steady state is reached;
wherein the determining step comprises determining a thermal conductivity of the object based on the first sensing signal and at least one of the series of sensing signals generated when the thermal steady state is reached,
and wherein the hydration indicator is generated based on the determined thermal conductivity.

Embodiment C22. The method of Embodiment C20 or 21, further comprising:
evaluating, by the one or more processors, whether a thermal steady state is reached;
deactivating the thermal source after the thermal steady state is reached.

Embodiment C23. The method of any one of Embodiment C20 to Embodiment C22, further comprising:
generating a series of cooling sensing signals after the thermal source is deactivated;
wherein the determining step comprises determining a thermal diffusivity of the object based on at least some of the series of cooling sensing signals,
and wherein the hydration indicator is generated based on the determined thermal diffusivity.

Embodiment C24. The method of any one of Embodiment C20 to Embodiment C23, wherein the reference data comprises at least one of an analytical function, a look-up table, a matrix, and a constant.

Embodiment C25. The method of any one of Embodiment C20 to Embodiment C24, further comprising: generating a calibration signal by the sensor when the sensor is disposed to a reference material with a known thermal property, wherein the determining step comprises determining the thermal property of the object using the calibration signal.

Embodiment C26. An RF hydration sensing system, comprising:
an RF sensor tag, comprising:
a substrate;
an antenna disposed on the substrate;
an RF circuit electrically coupled to the antenna;
a thermal source electrically coupled to the RF circuit for changing a thermal condition of a target area; and
a sensing element thermally coupled to the thermal source for sensing a temperature of the thermal source, such that when the thermal source is thermally coupled to a target area, the RF sensor tag wirelessly receives a first power having a first form from a transceiver, the RF circuit transforms the first power to a second power having a second form and delivers the second power to the thermal source, the sensing element senses a time variation of the thermal source temperature, and the RF sensor tag wirelessly transmits the sensed time variation of the thermal source temperature,
an RF reader configured to wirelessly transmit an interrogation power the RF sensor tag and receive the sensed time variation of the thermal source temperature,
a processor electronically coupled to the RF reader and configured to determine a hydration indicator indicative of hydration level based on the sensed time variation of the thermal source temperature.

Embodiment C27. The RF hydration sensing system of Embodiment C26, further comprising: a memory storing a reference data associated with hydration level, and wherein the processor is configured to determine the hydration indicator using the reference data.

Embodiment C28. The RF hydration sensing system of Embodiment C26 or 27, wherein the RF circuit controls a magnitude of the second power.

Embodiment C29. The RF hydration sensing system of any one of Embodiment C26 to Embodiment C28, wherein the RF circuit is configured to adjust duration of power supplied to the thermal source.

Embodiment C30. The RF hydration sensing system of any one of Embodiment C26 to Embodiment C29, wherein the RF sensor tags further comprises: a thermal spreader comprising a solid or liquid material, wherein the thermal source is disposed proximate to the thermal spreader.

Embodiment C31. The RF hydration sensing system of Embodiment C30, wherein the thermal spreader is adapted to substantially uniformly distribute thermal flux from the thermal source across the target area when the thermal spreader is in thermal contact with the target area.

Embodiment C32. The RF hydration sensing system of any one of Embodiment C26 to Embodiment C31, wherein the first form is an AC form and the second form is a DC form.

Embodiment C33. The RF hydration sensing system of any one of Embodiment C26 to Embodiment C32, wherein the RF sensor tag is configured to wirelessly receive an unknown first power having a first form from a transceiver, and wherein the RF circuit transforms the unknown first power to a known second power having a second form different from the first form.

Embodiment C34. The RF hydration sensing system of any one of Embodiment C26 to Embodiment C33, wherein the RF reader is configured to change the interrogation power based on sensed time variation of the thermal source temperature.

Embodiment C35. The RF hydration sensing system of any one of Embodiment C26 to Embodiment C34, further comprising: a coupling device configured to maintain thermal contact between the RF sensor tag and the target area.

Embodiment C36. The RF hydration sensing system of Embodiment C35, wherein the coupling device comprises at least one of a thermally conductive adhesive layer, an adhesive layer, an elastic coupler, and a mechanical coupler.

The present invention should not be considered limited to the particular examples and embodiments described above, as such embodiments are described in detail to facilitate explanation of various aspects of the invention. Rather the present invention should be understood to cover all aspects of the invention, including various modifications, equivalent processes, and alternative devices falling within the spirit and scope of the invention as defined by the appended claims and their equivalents.

What is claimed is:

1. An RF hydration sensor in an assembly, comprising:
a substrate;
an antenna disposed on the substrate;
an RF circuit electrically coupled to the antenna, the RF circuit comprising a processor;
a thermal source electrically coupled to the RF circuit for changing a thermal condition of a target area; and
a sensing element thermally coupled to the thermal source for sensing a temperature of the thermal source, such that when the thermal source is thermally coupled to the target area, the RF hydration sensor wirelessly receives a first power having a first form from a transceiver, the RF circuit transforms the first power to a second power having a second form different from the first form and delivers the second power to the thermal source, the sensing element senses a time variation of the thermal source temperature, and the processor determines a hydration indicator indicating a hydration level of the target area based on the sensed time variation of the thermal source temperature.

2. The RF hydration sensor of claim 1, further comprising:
a memory storing a reference data associated with the hydration level, and wherein the processor is configured to determine the hydration indicator using the reference data.

3. The RF hydration sensor of claim 1, wherein the RF circuit controls a magnitude of the second power.

4. The RF hydration sensor of claim 1, wherein the RF circuit is configured to adjust a duration of the second power supplied to the thermal source.

5. The RF hydration sensor of claim 1, wherein the RF hydration sensor is configured to wirelessly receive an unknown first power having a first form from a transceiver, and wherein the RF circuit transforms the unknown first power to a known second power having a second form different from the first form.

6. The RF hydration sensor of claim 1, wherein the RF hydration sensor is adapted to wirelessly communicate with a remote transceiver emitting power at a first radio frequency, wherein the RF circuit is adapted to detune a resonant frequency of the RF hydration sensor away from the first radio frequency to control a magnitude of the first power received by the RF hydration sensor from the remote transceiver.

7. The RF hydration sensor of claim 1, further comprising:
a thermal spreader comprising a solid or liquid material, wherein the thermal source is disposed proximate to the thermal spreader.

8. The RF hydration sensor of claim 7, wherein the thermal spreader is adapted to substantially uniformly distribute a thermal flux from the thermal source across the target area when the thermal spreader is in thermal contact with the target area.

9. An RF sensor for measuring a liquid level, comprising:
a substrate;
an antenna disposed on the substrate;
an RF circuit electrically coupled to the antenna, the RF circuit comprising a processor;
an absorption element comprising an absorption material,
a thermal source electrically coupled to the RF circuit and thermally coupled to the absorption element; and
a sensing element thermally coupled to the thermal source for sensing a temperature of the thermal source, such that after the absorption element is used to absorb a liquid, the RF sensor wirelessly receives a first power having a first form from a transceiver, the RF circuit transforms the first power to a second power having a second form different from the first form and delivers the second power to the thermal source, the sensing element senses a time variation of the thermal source temperature, and the processor determines an indicator indicating a liquid level based on the sensed time variation of the thermal source temperature.

10. The RF sensor of claim 9, wherein the absorption material comprises at least one of a porous material, a natural or synthetic sponge, a water-absorbing gel, and a superabsorbent polymer.

11. The RF sensor of claim 9, wherein the RF circuit controls a magnitude of the second power.

* * * * *